(12) United States Patent
Coonrod et al.

(10) Patent No.: US 9,185,861 B2
(45) Date of Patent: Nov. 17, 2015

(54) *BRASSICA* PLANTS YIELDING OILS WITH A LOW ALPHA LINOLENIC ACID CONTENT

(75) Inventors: Daren Kenneth Coonrod, Fort Collins, CO (US); Kevin Brandt, Longmont, CO (US); Honggang Zheng, Fort Collins, CO (US); Zhizheng Chen, Fort Collins, CO (US); Richard Fletcher, Windsor, CO (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 13/429,649

(22) Filed: Mar. 26, 2012

(65) Prior Publication Data

US 2012/0216319 A1 Aug. 23, 2012

Related U.S. Application Data

(63) Continuation of application No. PCT/US2011/037864, filed on May 25, 2011.

(60) Provisional application No. 61/348,121, filed on May 25, 2010.

(51) Int. Cl.
*A01H 5/10* (2006.01)
*C12N 9/00* (2006.01)
*C12N 9/02* (2006.01)
*C12N 15/82* (2006.01)

(52) U.S. Cl.
CPC ............... *A01H 5/10* (2013.01); *C12N 9/0083* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 4,948,811 A | 8/1990 | Spinner et al. | |
| 5,387,758 A * | 2/1995 | Wong et al. | 800/264 |
| 5,434,283 A | 7/1995 | Wong et al. | |
| 5,545,821 A | 8/1996 | Wong et al. | |
| 5,625,130 A | 4/1997 | Grant et al. | |
| 5,644,066 A | 7/1997 | Sakai et al. | |
| 5,668,299 A | 9/1997 | Debonte et al. | |
| 5,750,827 A | 5/1998 | Debonte et al. | |
| 5,767,338 A | 6/1998 | Fan | |
| 5,850,026 A | 12/1998 | Debonte et al. | |
| 5,859,350 A | 1/1999 | DeBonte et al. | |
| 5,863,589 A | 1/1999 | Covington, Jr. et al. | |
| 5,866,762 A | 2/1999 | DeBonte et al. | |
| 5,885,643 A | 3/1999 | Kodali et al. | |
| 5,955,623 A | 9/1999 | Grant et al. | |
| 5,965,755 A | 10/1999 | Sernyk et al. | |
| 6,011,164 A | 1/2000 | Grant et al. | |
| 6,229,072 B1 | 5/2001 | Burns et al. | |
| 6,303,849 B1 | 10/2001 | Potts et al. | |
| 6,323,392 B1 | 11/2001 | Charne | |
| 6,342,658 B1 | 1/2002 | DeBonte et al. | |
| 6,392,127 B1 | 5/2002 | Charne et al. | |
| 6,489,543 B1 | 12/2002 | Sernyk | |
| 6,562,397 B2 | 5/2003 | DeBonte et al. | |
| 6,737,564 B2 | 5/2004 | Yao et al. | |
| 6,787,686 B2 | 9/2004 | Potts et al. | |
| 6,967,243 B2 | 11/2005 | Debonte et al. | |
| 7,081,564 B2 | 7/2006 | Somers et al. | |
| 7,109,392 B1 | 9/2006 | Broglie et al. | |
| 7,566,813 B2 | 7/2009 | Voelker et al. | |
| 7,741,542 B2 | 6/2010 | DeBonte et al. | |
| 7,790,959 B2 | 9/2010 | Kishore et al. | |
| 8,057,835 B2 | 11/2011 | Makadia et al. | |
| 8,088,978 B2 | 1/2012 | Vrinten et al. | |
| 8,304,610 B2 | 11/2012 | Yao et al. | |
| 2001/0037514 A1 | 11/2001 | Kodali et al. | |
| 2003/0131379 A1 * | 7/2003 | Debonte et al. | 800/281 |
| 2003/0221217 A1 | 11/2003 | Yao et al. | |
| 2005/0039233 A1 | 2/2005 | Yao et al. | |
| 2005/0262588 A1 | 11/2005 | Dehesh et al. | |
| 2006/0206963 A1 | 9/2006 | Voelker et al. | |
| 2007/0065565 A1 | 3/2007 | Kincs et al. | |
| 2008/0260933 A1 | 10/2008 | Thompson et al. | |
| 2009/0019601 A1 | 1/2009 | Kovalic | |
| 2010/0143570 A1 | 6/2010 | Ripley et al. | |
| 2012/0246755 A1 * | 9/2012 | Laga et al. | 800/264 |

FOREIGN PATENT DOCUMENTS

| | | | | |
|---|---|---|---|---|
| BE | WO2009/007091 A2 * | 1/2009 | | C12N 15/82 |
| CA | 225398 A | 10/1922 | | |
| CA | 2340611 A1 | 4/1993 | | |
| CA | 2462725 A1 | 4/1993 | | |
| CA | 1337251 | 10/1995 | | |
| CA | 2056988 | 12/1995 | | |
| CA | 2340998 | 9/2002 | | |
| CA | 2382767 A1 | 11/2003 | | |
| CA | 2180386 | 9/2006 | | |
| CN | 101421406 | 4/2009 | | |
| WO | 9203919 | 3/1992 | | |
| WO | 9311245 | 6/1993 | | |
| WO | 9318158 | 9/1993 | | |
| WO | 9424849 | 11/1994 | | |

(Continued)

OTHER PUBLICATIONS

Lysak et al. 2005 Genome Research 15: p. 516-525.*
Ford et al 2006 (Proceedings of the Royal Society Biosciences 273: p. 3111-3115).*
Arondel, V., et al., "Map-Based Cloning of a Gene Controlling Omega-3 Fatty Acid Desaturation in *Arabidopsis*," Science 258:1353-1355 (1992).
Barker, G. C., et al., "Novel Insights into Seed Fatty Acid Synthesis and Modification Pathways from Genetic Diversity and Quantitative Trait Loci Analysis of the *Brassica* C Genome1[OA]" Plant Physiology 144:1827-1842 (2007).
Bonaventure, G., et al., "Disruption of the FATB Gene in *Arabidopsis* Demonstrates an Essential Role of Saturated Fatty Acids in Plant Growth," Plant Cell 15:1020-1033 (2003).
Chenna, R., et al., "Multiple Sequence Alignment with the Clustal Series of Programs," Nucleic Acids Res. 31 (13):3497-3500 (2003).
Eccleston, V. S., et al., "Expression of Lauroyl-Acyl Carrier Protein Thioesterase in *Brassica napus* Seeds Induces Pathways for Both Fatty Acid Oxidation and Biosynthesis and Implies a Set Point for Triacylglycerol Accumulation," Plant Cell 10:613-621 (1998).

(Continued)

*Primary Examiner* — Brent T Page
*Assistant Examiner* — Matthew Keogh

(57) ABSTRACT

*Brassica* plants producing oils with a low alpha-linolenic acid content and methods for producing such plants are described.

6 Claims, 20 Drawing Sheets

(56) References Cited

FOREIGN PATENT DOCUMENTS

| WO | 9627285 | 9/1996 |
|---|---|---|
| WO | 9721340 | 6/1997 |
| WO | 9743907 | 11/1997 |
| WO | 9850569 | 11/1998 |
| WO | 9855633 | 12/1998 |
| WO | 9856239 | 12/1998 |
| WO | 0009721 | 2/2000 |
| WO | 0019832 | 2/2000 |
| WO | 0138502 | 5/2001 |
| WO | 2006034059 | 3/2006 |
| WO | 2006042049 | 4/2006 |
| WO | 2006079567 | 8/2006 |
| WO | 2007016521 A2 | 2/2007 |
| WO | 2007107590 A2 | 9/2007 |
| WO | 2008135296 A2 | 11/2008 |
| WO | 2009007091 A2 | 1/2009 |
| WO | 2011060946 A1 | 5/2011 |
| WO | 2011075716 A1 | 6/2011 |

OTHER PUBLICATIONS

GenBank Deposit AY599884. *Brassica* cDNA, RiceGE: Genome Express Database, Oct. 6, 2010.
Ginalski, K, et al., "Detection of Reliable and Unexpected Protein Fold Predictions Using 3D-Jury," Nucleic Acids Res. 31(13):3291-3292 (2003).
Goren, M. A., et al., "Wheat Germ Cell-Free Translation, Purification, and Assembly of a Functional Human Stearoyl-Coa Desaturase Complex," Protein Expr. Purif. 62(2):171-178 (2008).
Hawrysh, Z. J., "Stability of Canola Oil," Canola and Rapeseed: Production Chemistry, Nutrition and Processing Technology, Van Nostrand, Reinhold, N. Y., Ch. 7, pp. 99-122 (1990).
Jones, A., et al., "Palmitoyl-Acyl Carrier Protein (ACP) Thioesterase and the Evolutionary Origin of Plant Acyl-ACP Thioesterases," Plant Cell 7:359-371 (1995).
Lloyd, A., et al., "Targeted Mutagenesis Using Zinc-Finger Nucleases in *Arabidopsis*," PNAS 102:2232-2237 (2005).
Lysak, M. A., et al., "Chromosome Triplication Found Across the Tribe Brassiceae," Genome Res. 15:516-525 (2005).
Mayer, K. M., et al., "Identification of Amino Acid Residues Involved in Substrate Specificity of Plant Acyl-ACP Thioesterases Using a Bioinformatics-Guided Approach," BMC Plant Biol. 7:1, doi:10.1186/1471-2229-7-1 (2007).
Mayer, K. M., et al., "Lipids and Lipoproteins: A Structural Model of the Plant Acyl-Acyl Carrier Protein Thioesterase FatB Comprises Two Helox/4-Stranded Sheet Domains, the N-Terminal Domain Containing Residues that Affect Specificity and the C-Terminal Domain Containing Catalytic Residues," J. Biol. Chem. 280:3621-3627 (2005).
McCallum, C. M., et al., "Targeting Induced Local Lesions in Genomes (TILLING) for Plant Functional Genomics," Plant Physiology 123:439-442 (2000).
Mounts, T. L., "Odor Considerations in the Use of Frying Oils," J. Amer. Oil Chemists' Soc. 56:659-663 (1979).
Pellan-Delourme, R., et al., "Cytoplasmic Male Sterility in Rapeseed (*Brassica napus* L.): Female Fertility of Restored Rapeseed with "Ogura" and Cybrids Cytoplasms," Genome 30:234-238 (1988).
Riungu, T. C., et al., "Development and Evaluation of *Diplotaxis muralis* (mur) Cytoplasmic Male Sterility System in Summer Rape," Can. J. Plant Sci. 83:261-269 (2003).
Tovkach, A., et al., "A Toolbox and Procedural Notes for Characterizing Novel Zinc Finger Nucleases for Genome Editing in Plant Cells," Plant J. 57:747-757 (2009).
Townsend, J. A., et al., "High Frequency Modification of Plant Genes Using Engineered Zinc Finger Nucleases," Nature 459(7245):442-445 (2009).

United States Patent and Trademark Office, International Search Report and Written Opinion dated May 4, 2011 for PCT/US2010/061226.
United States Patent and Trademark Office, International Search Report and Written Opinion dated Dec. 1, 2011 for PCT/US2011/037864.
United States Patent and Trademark Office, International Search Report and Written Opinion dated Dec. 20, 2011 for PCT/US2011/045235.
Voelker, T., "Plant Acyl-Acp Thioesterases: Chain-Length Determining Enzymes in Plant Fatty Acid Biosynthesis," Genetic Engineering 118:111-133 (1996).
Yadav, N. S., et al., "Cloning of Higher Plant w-3 Fatty Acid Desaturases," Plant Physiol. 103:467-476 (1993).
Frankel Ae et al., "Characterization of diphtheria fusion proteins targeted to the human interleukin-3 receptor", Protein Eng., 2000, vol. 13, N. 8, pp. 575-581.
Przybylski, R., Mag, T., Eskin, N. and McDonald, B. 2005. Canola Oil. Bailey's Industrial Oil and Fat Products. 2:2.
Facciotti et al., "Molecular dissection of the plant acyl-acyl carrier protein thioesterases", Fett/Lipid 100 (1998), Nr. 4-5, p. 167-172.
Hohe et al., "A tool for understanding homologous recombination in plants", Plant Cell Rep. (2003), 21:1135-1142.
C. A. McCartney, et al., 'Genotypic and environmental effects on saturated fatty acid concentration of canola grown in Manitoba, Canadian Journal of Plant Science, 2004, 84(3): 749-756, 10.4141/P03-119.
Guangyun Hou et al., "Environmental efects on fatty acid levels in soybean seed oil", Journal of the American Oil Chemists' Society, vol. 83, Issue 9, pp. 759-763 (2006).
Moreno-Perez et al., "Acyl-ACP thioesterases from macadamia (*Macadamia tetraphylla*) nuts: Cloning, characterization and their impact on oil composition", Plant Physiology and Biochemistry, vol. 49, No. 1, Jan. 1, 2011, pp. 82-87.
Hawkins, D.J. et al., "Characterization of acyl-ACP thioesterases of mangosteen (*Garcinia mangostana*) seed and high levels of stearate production in transgenic canola", The Plant Journal. 1998, vol. 13, No. 6, pp. 743-752.
Loader, N. M. et al., "Isolation and characterization of two Brassica napus embryo acyl-ACP thioesterase cDNA clones", Plant Molecular Biology, vol. 23 (4), pp. 769-778 (1993).
Hellyer et al., "Induction, purification and characterisation of acyl-ACP thioesterase from developing seeds of oil seed rape (*Brassica napus*)", Plant Molecular Biology, vol. 20, pp. 763-780, 1992.
The UniProt Consortium, UniProt: a hub for protein information, FATA2_ARATH, Primary Accession No. Q9SV64 (2012).
Facciotti, M. T. et al., "Improved stearate phenotype in transgenic canola expressing a modified acyl-acyl carrier protein thioesterase", Nature Biotechnology, 1999, vol. 17, pp. 593-597.
Serrano-Vega et al., "Cloning, characterization and structural model of a PatA-type thioesterase from sunflower seeds (*Helianthus annuus* L.)", Planta; An International Journal of Plant Biology, Springer, Berlin, DE, vol. 221, No. 6, Aug. 1, 2005, pp. 868-880.
Michelle E. Beaith et al., "Reduction of saturated fats by mutagenesis and heat selection in *Brassica napus* L", Euphytica, vol. 133, Issue 1-2, pp. 1-9 (2005).
Dimov, Z. and Möllers, C. (2010), Genetic variation for saturated fatty acid content in a collection of European winter oilseed rape material (*Brassica napus*). Plant Breeding, 129: 82-86.
Abdelali Hannoufa et al., "Genetic enhancement of *Brassica napus* seed quality", Transgenic Research, vol. 23, Issue 1, pp. 39-52 (2014).
Pellan-Delourme and Renard, 1987, Proc. 7th Int. Rapeseed Conf., Poznan, Poland, p. 199-203.

\* cited by examiner

```
  1 MVVAMDQRSN VNGDSGARKE EGFDPSEQPP FKIGDIRAAI PKHCWVKSPL RSMSYVARDI
 61 FAVAALAMAA VYFDSWFLWP LYWVAQGTLF WAIFVLGHDC GHGSFSDIPL LNSVVGHILH
121 SFILVPYHGW RISHRTHHQN HGHVENDESW VPLPEKLYKN LPHSTRMLRY TVPLPMLAYP
181 IYLWYRSPGK EGSHFNPYSS LPAPSERKLI ATSTTCWSIM LATLVYLSFL VGPVTVLKVY
241 GVPYIFVMW LDAVTYLHHH GHDEKLPWYR GKEWSYLRGG LTTIDRDYGI FNNIBHDIGT
301 HVIHHLFPQI PHYHLVDATR AAKHVLGRYY REPKTSGAIP IHLVESIVAS IKKDHYVSDT
361 GDIVFYETDP DLYVYASDKS KIN.
```

FIGURE 5

```
                              SEQUENCE LISTING

<160> NUMBER OF SEQ ID NOS: 34

<210> SEQ ID NO 1
<211> LENGTH: 3691
<212> TYPE: DNA
<213> ORGANISM: Brassica napus

<400> SEQUENCE: 1
atggttgttg ctatggacca acgcaccaat gtgaacggag atgccggtgc ccggaaggaa      60
gaagggtttg atccgagcgc acaaccgccg tttaagatcg gggacataag ggctgcgatt     120
cctaagcatt gttgggtgaa aagtcctttg agatctatga gctacgtagc cagagacatt     180
tgtgccgtcg cggctttggc cattgccgcc gtgtattttg atagctggtt cctctgtcct     240
ctctattggg tcgcccaagg aacccttttc tgggccatct tcgtcctcgg ccacgactgg     300
taaagtttct tccattttgc attgcatcga tttattgaat gcacgttcta cgagtattgt     360
ttgtcagtta cttcgtaaaa tgattctttt gatgttcatt ttttgaagat ctaagatttt     420 ttttttttaga ttttcttttt aaatcattgt tccaccacca cctttcatcg gtcgtacgac     480
tcgttacaac accacatctt tattttctat aattactact gcttccgcat tttatggatc     540
tctcaactta taattaaagt ataatatcaa gaatatctat tattttcttt aaacaagaaa     600
gataatattg tttctttgtt attttggtgt atttccaatc tatttcgaga tttagaaatg     660
tgacacgtca ttaccttgtt gaagtgttta aaacaaacat ggaaagttta aataaatagt     720
gcaataaatg atatatatgt atatgatgaa taatgatgtg aaatataatt gaataatggc     780
agtggacatg ggagtttctc agacattcct ctgctgaata gtgtggttgg ccatattctt     840
cattccttca tcctcgttcc ttaccatggt tggtaagtca gcttatcaac cctttttact     900
atattattaa ttattaaact tgcatttgta tacttggtgc aagttggtaa atgtaatctg     960
ataactgaaa atctattcat tgctcgttct atttttttt tggctagaga caattttata    1020
attaaataat gcatgtgaga atatgactat ttatgtgagg tagctttttct tattcctgtc    1080 gaaaagcatc aaatctttag caacgaagga aaaaggaatc aaatttttta ttaaatgcaa    1140
tgggtctatg tcttggtcat tagttttttg catataattt atttatattt ttttcttaac    1200
agcagctaat ttaattataa ttaaatattc attttataaa taatattaga ccaattatta    1260
aaggttagat attttaagaa ttattcatga cttttgtttat tggaactcct tttatctttt    1320 aatctttttct atttctccat ttttaataat gagaaactga cttcaaatct ccaataaaga    1380
tggtcttatg tagtaacagt ataatttttt gtttggtaaa tgtaacatca tcttcaaata    1440
tctttgaaaa tagacttaca tgcattattt tgctgcgaca ttattgtcac ttattcctgg    1500
caataaatta gtttattact gaactttttt ttggtcaatt tattactagt aactttaaac    1560
ttaaaagagt gagattgttt gatcaaaaaa aataaaaata gagtgagata gttagaatct    1620
gccatgaaag caacactata tagacaattt aatttttatg aaaacacatt taataatttg    1680
aggctgcagg agaataagcc atcggacaca ccaccagaac catggccatg ttgaaaacga    1740
cgagtcttgg gttccagtaa catttccctc tttaataatt tctattttc tgtcaaaata    1800 attagttttt cgaaatttga ggccagaacg accacttgtc aaatttgatt tttagctgta    1860
gtaaaaacag tttgctagtg tcacagttaa ccggtaattg attcttttta acgatttata    1920
```

-continued

```
gaagtaacat ttttgtaaaa taaaatatac attatggtat gtgacaacgg accacgctta    1980
tttgtattgg tgaatctttt aattactccc tccaatttat tttagttgca gatttagatt    2040
tatgcacata gattaataaa aatattttgc acattttcaa aataaaaaca ccattactta    2100
tacaactaac catatttcaa ccaataaaaa taaattagaa atatattttt ataaattttg    2160
tattgaaatt ataaaataat acttatttta aaacgaaatt aatttacaac gacaattaaa    2220
ctgaaacgga aagaaattat taatacttaa ttaaagagtt tttagaaaaa ttgaaagaca    2280
tgtttatgcg aaactcatgt gaaagtcttt gaaataatag attttggtat aaatatttca    2340
aattttctta aaataataat tatatattaa tataatttgt gataaaatct cgtcaaaaac    2400
tcactaatgc aaatgctttt attttgaatt tcttactcct ctaaatgcat ttacttttat    2460
actaatatta ttttctttct ctaatttggc gtttcgtaat agtttgtctg tattttgaaa    2520
actaacaaaa aataataaaa acaaaagctt ataaacacat agcatgcaat gaatatgtac    2580
gaatatatat accaatacat atctaagtac tatttttcca agtacttaat cttgattact    2640
aaaattcatt ttaattgttc ctttcagtta ccagaaaggt tatacaagaa tttacccac    2700 agtactcgga tgctcagata cactgtccct ctgcccatgc tcgcttaccc gatctatctg    2760 gtattttta attcctaaaa tttactacaa gtcattttag actgtgtttt aaaacaatat    2820 aattatttt gtttggtttt actgcagtgg tacagaagtc ctggaaaaga agggtcacat    2880
tttaacccat acagtggttt atttgctcca agcgagagaa agcttattgc aacttcgact    2940
acttgctggt ccataatgtt ggcaattctt atctgtcttt ccttcctcgt tggtccagtc    3000
acagttctca agtatacgg tgttccttac attgtaagtt tcttagtata tcataaggg    3060 tatatattta ttattcaata tatatactat atgatttgtt tttgtcatat attttgaaa    3120 tattcagatc tttgtgatgt ggttggacgc tgtcacttac ttgcatcacc atggtcatga    3180
tgagaagttg ccttggtaca gaggcaaggt aattaaatta actattacaa gtatttaca    3240 aaaaactaat gattagtata tttgattaat cttaattctt gatgtttgt gattaataat    3300 aggaatggag ttacttacgt ggaggattaa caactattga tagagattac ggattttca    3360 acaacattca tcacgacatt ggaactcacg tgatccatca tcttttccca caaatccctc    3420
actatcactt ggtcgatgct gtgagtcatc tcactctctg gctactttca tcaaaaccat    3480
ttgattaaag ggtgattaat tactaatgta gtgattttaa caaatggaat gtgacagaca    3540
aaagcagcta acatgtgtt gggaagatac tacagagaac caaagacgtc aggagcaata    3600
ccgatccact tggtggagag tttggtagca agtattaaga aagatcatta cgtcagtgac    3660
actggtgaca ttgtcttcta cgagactgat c                                   3691
```

<210> SEQ ID NO 2
<211> LENGTH: 3691
<212> TYPE: DNA
<213> ORGANISM: Brassica napus

<400> SEQUENCE: 2

```
atggttgttg ctatggacca acgcaccaat gtgaacggag atgccggtgc ccggaaggaa      60
gaagggtttg atccgagcgc acaaccgccg tttaagatcg gggacataag ggctgcgatt     120
cctaagcatt gttgggtgaa aagtcctttg agatctatga gctacgtagc cagagacatt     180
tgtgccgtcg cggctttggc cattgccgcc gtgtattttg atagctggtt cctctgtcct     240
ctctattggg tcgcccaagg aacccttttc tgggccatct tcgtcctcgg ccacgactgg     300
```

```
taaagtttct tccatttttgc attgcatcga tttattgaat gcacgttcta cgagtattgt    360
ttgtcagtta cttcgtaaaa tgattctttt gatgttcatt ttttgaagat ctaagatttt    420
tttttttaga ttttcttttt aaatcattgt tccaccacca cctttcatcg gtcgtacgac    480
tcgttacaac accacatctt tattttctat aattactact gcttccgcat tttatggatc    540
tctcaactta taattaaagt ataatatcaa gaatatctat tattttctt aaacaagaaa     600 gataatattg tttctttgtt attttggtgt atttccaatc tatttcgaga tttagaaatg    660
tgacacgtca ttaccttgtt gaagtgttta aaacaaacat ggaaagttta aataaatagt    720
gcaataaatg atatatatgt atatgatgaa taatgatgtg aaatataatt gaataatggc    780
agtggacatg ggagtttctc agacattcct ctgctgaata gtgtggttgg ccatattctt    840
cattccttca tcctcgttcc ttaccatggt tggtaagtca gcttatcaac cctttttact    900
atattattaa ttattaaact tgcatttgta tacttggtgc aagttggtaa atgtaatctg    960
ataactgaaa atctattcat tgctcgttct atttttttt tggctagaga caattttata     1020
attaaataat gcatgtgaga atatgactat ttatgtgagg tagcttttct tattcctgtc    1080
gaaaagcatc aaatctttag caacgaagga aaaggaatc aaattttta ttaaatgcaa      1140 tgggtctatg tcttggtcat tagttttttg catataattt atttatattt ttttcttaac    1200
agcagctaat ttaattataa ttaaatattc attttataaa taatattaga ccaattatta    1260
aaggttagat attttaagaa ttattcatga ctttgtttat tggaactcct tttatctttt    1320
aatcttttct atttctccat ttttaataat gagaaactga cttcaaatct ccaataaaga    1380
tggtcttatg tagtaacagt ataatttttt gtttggtaaa tgtaacatca tcttcaaata    1440
tctttgaaaa tagacttaca tgcattattt tgctgcgaca ttattgtcac ttattcctgg    1500
caataaatta gtttattact gaacttttttt ttggtcaatt tattactagt aactttaaac    1560
ttaaaagagt gagattgttt gatcaaaaaa aataaaata gagtgagata gttagaatct     1620
gccatgaaag caacactata tagacaattt aattttatg aaaacacatt taataattg      1680 aggctgcagg agaataagcc atcggacaca ccaccagaac catggccatg ttgaaaacga    1740
cgagtcttgg gttccggtaa catttccctc tttaataatt tctattttc tgtcaaaata     1800 attagttttt cgaaatttga ggccagaacg accacttgtc aaatttgatt tttagctgta    1860
gtaaaaacag tttgctagtg tcacagttaa ccggtaattg attctttta acgatttata    1920 gaagtaacat ttttgtaaaa taaaatatac attatggtat gtgacaacgg accacgctta    1980
tttgtattgg tgaatctttt aattactccc tccaatttat tttagttgca gatttagatt    2040
tatgcacata gattaataaa aatatttgc acattttcaa aataaaaaca ccattactta     2100
tacaactaac catatttcaa ccaataaaaa taaattagaa aatattattt ataaattttg    2160
tattgaaatt ataaaataat acttatttta aaacgaaatt aatttacaac gacaattaaa    2220
ctgaaacgga aagaaattat taatacttaa ttaaagagtt tttagaaaaa ttgaaagaca    2280
tgtttatgcg aaactcatgt gaaagtcttt gaaataatag attttggtat aaatatttca    2340
aattttctta aaataataat tatatattaa tataatttgt gataaaatct cgtcaaaaac    2400
tcactaatgc aaatgctttt attttgaatt tcttactcct ctaaatgcat ttactttat     2460 actaatatta ttttctttct ctaatttggc gtttcgtaat agtttgtctg tattttgaaa    2520
actaacaaaa aataataaaa acaaaagctt ataaacacat agcatgcaat gaatatgtac    2580
gaatatatat accaatacat atctaagtac tattttccca agtacttaat cttgattact    2640
aaaattcatt ttaattgttc ctttcagtta ccagaaaggt tatacaagaa tttaccccac    2700
```

-continued

```
agtactcgga tgctcagata cactgtccct ctgcccatgc tcgcttaccc gatctatctg   2760 gtattttta attcctaaaa tttactacaa gtcatttag actgtgtttt aaaacaatat     2820
aattattttt gtttggtttt actgcagtgg tacagaagtc ctggaaaaga agggtcacat   2880
tttaacccat acagtggttt atttgctcca agcgagagaa agcttattgc aacttcgact   2940
acttgctggt ccataatgtt ggcaattctt atctgtcttt ccttcctcgt tggtccagtc   3000
acagttctca agtatacgg tgttccttac attgtaagtt tcttagtata tcataaaggg    3060
tatatattta ttattcaata tatatactat atgatttgtt tttgtcatat attttgaaa    3120 tattcagatc tttgtgatgt ggttggacgc tgtcacttac ttgcatcacc atggtcatga   3180
tgagaagttg ccttggtaca gaggcaaggt aattaaatta actattacaa gtattttaca   3240
aaaaactaat gattagtata tttgattaat cttaattctt gatgttttgt gattaataat   3300
aggaatggag ttacttacgt ggaggattaa caactattga tagagattac ggaattttca   3360
acaacattca tcacgacatt ggaactcacg tgatccatca tcttttccca caaatccctc   3420
actatcactt ggtcgatgct gtgagtcatc tcactctctg gctactttca tcaaaaccat   3480
ttgattaaag ggtgattaat tactaatgta gtgattttaa caaatggaat gtgacagaca   3540
aaagcagcta acatgtgtt gggaagatac tacagagaac caaagacgtc aggagcaata    3600
ccgatccact tggtggagag tttggtagca agtattaaga aagatcatta cgtcagtgac   3660
actggtgaca ttgtcttcta cgagactgat c                                  3691
```

<210> SEQ ID NO 3
<211> LENGTH: 3829
<212> TYPE: DNA
<213> ORGANISM: Brassica rapa

<400> SEQUENCE: 3

```
gaacccttc ttcaccacat tccacttccc acactctctt ttttttgaa ttatagagag      60 agaatcctcc tccaaatctc tctctctccc aggatggttg ttgctatgga ccaacgcacc   120
aatgtgaacg gagatgccgg tgcccggaag gaagaagggt ttgatccgag cgcacaaccg   180
ccgtttaaga tcgggacat aagggctgcg attcctaagc attgttggt gaaaagtcct    240 ttgagatcta tgagctacgt agccagagac atttgtgccg tcgcggcttt ggccattgcc   300
gccgtgtatt ttgatagctg gttcctctgt cctctctatt gggtcgccca aggaacccct   360
ttctgggcca tcttcgtcct cggccacgac tggtaaagtt tcttccattt tgcattgcat   420
cgatttattg aatgcacgtt ctacgagtat tgtttgtcag ttacttcgta aaatgattct   480
tttgatgttc atttttgaa gatctaagat tttttttttt agatttctt tttaaatcat     540 tgttccacca ccacctttca tcggtcgtac gactcgttac aacaccacat ctttttttc    600 tataattact actgcttccg cattttatgg atctctcaac ttataattaa agtataatat   660
caagaatatc tattattttt cttaaacaag aaagataata ttgtttcttt gttattttgg   720
tgtatttcca atctatttcg agatttagaa atgtgacacg tcattacctt gttgaagtgt   780
ttaaaacaaa catggaaagt ttaaataaat agtgcaataa atgatatata tgtatatgat   840
gaataatgat gtgaaatata attgaataat ggcagtggac atgggagttt ctcagacatt   900
cctctgctga atagtgtggt tggccatatt cttcattcct tcatcctcgt tccttaccat    960
ggttggtaag tcagcttatt aaccctttt actatattat taattattaa acttgcattt    1020
gtatacttgg tgcaagttgg taaatgtaat ctgataactg aaaatctatt cattgctcgt   1080
```

```
tcttttttt  tttggctaga  gacaatttta  taattaaata  atgcatgtga  gaatatgact  1140
atttatgtga  ggtagctttt  cttattcctg  tcgaaaagca  tcaaatcttt  agcaacgaag  1200
gaaaaaggaa  tcaaattttt  tattaaatgc  aatgggtcta  tgtcttggtc  attagttttt  1260
tgcatataat  ttatttatat  tttttctga   acagcagcta  atttaattat  aattaaatat  1320
tcattttata  aataatatta  gaccaattat  taaaggttag  atattttaag  aattattcat  1380
gactttgttt  attggaactc  cttttatctt  ttaatcttt   ctatttctcc  attttttaata 1440 atgagaaact  gacttcaaat  ctccaataaa  gatggtctta  tgtagtaaca  gtataatttt  1500
ttgtttggta  aatgtaacat  catcttcaaa  tatctttgaa  aatagactta  catgcattat  1560
tttgctgcga  cattattgtc  acttattcct  ggcaataaat  tagtttatta  ctgaaaactt  1620 tttttttggtc aatttattac  tagtaacttt  aaacttaaaa  gagtgagatt  gtttgatcaa  1680
aaaaaataaa  aatagagtga  gatagttaga  atctgccatg  aaagcaacac  tatatagaca  1740 attttaatttt tatgaaaaca cattaaataa  tttgaggctg  caggagaata  agccatcgga  1800
cacaccacca  gaaccatggc  catgttgaaa  acgacgagtc  ttgggttccg  gtaacatttc  1860
cctctttaat  aatttctatt  tttctgtcaa  aataattagt  ttttcgaaat  ttgaggccag  1920
aacgaccact  tgtcaaattt  gattttttagc tgtagtaaaa  acagtttgct  agtgtcacag  1980
ttaaccggta  attgattctt  tttaacgatt  tatagaagta  acattttgt   aaaataaaat  2040 atacattatg  gtatgtgaca  acggaccacg  cttatttgta  ttggtgaatc  ttttaattac  2100
tccctccgat  ttattttagt  tgcagattta  gatttatgca  catagattaa  taaaaatatt  2160
ttgcacattt  tcaaaataaa  aacacaatta  cttatacaac  taaccatatt  tcaaccaata  2220
aaaataaatt  agaaaatatt  atttataaat  tttgtattga  aattataaaa  taatacttat  2280
tttaaaacga  aattaattta  caacgacaat  taaactgaaa  cggaaagaaa  ttattaatac  2340
ttaattaaag  agttttaga   aaaattgaaa  gacatgttta  tgcgaaactc  atgtgaaagt  2400
ctttgaaata  atagattttg  gtataaatat  ttcaaatttt  cttaaaataa  taattatata  2460
ttaatataat  ttgtgataaa  atctcgtcaa  aaactcacta  atgcaaatgc  ttttatttttg 2520 aatttcttac  tcctctaaat  gcatttactt  ttatactaat  attattttct  ttctctaatt  2580
tggcatttcg  taatagtttg  tctgtatttt  gaaaactaac  aaaaaataat  aaaaacaaaa  2640
gcttataaac  acatagcatg  caatgaatat  gtacgaatat  ataccaat    acatatctaa  2700 gtactatttt  tccaagtact  taatcttgat  tactaaaatt  cattttaatt  gttcctttca  2760
gttaccagaa  aggttataca  agaatttacc  ccacagtact  cggatgctca  gatacactgt  2820
ccctctgccc  atgctcgctt  acccgatcta  tctggtattt  tttaattcct  aaaatttact  2880
acaagtcatt  ttagactgtg  ttttaaaaca  atataattat  ttttgtttgg  ttttactgca  2940
gtggtacaga  agtcctggaa  aagaagggtc  acattttaac  ccatacagtg  gtttatttgc  3000
tccaagcgag  agaaagctta  ttgcaacttc  gactacttgc  tggtccataa  tgttggcaat  3060
tcttatctgt  cttccttcc   tcgttggtcc  agtcacagtt  ctcaaagtat  acggcgttcc  3120
ttacattgta  agtttcttag  tatatcataa  agggtatata  tttattattc  aatatatata  3180
ctatatgatt  tgtttttgtc  atatattttt  gaaatattca  gatctttgtg  atgtggttgg  3240
acgctgtcac  ttacttgcat  caccatggtc  atgatgagaa  gttgccttgg  tacagaggca  3300
aggtaattaa  attaactatt  acaagtattt  tacaaaaaac  taatgattag  tatatttgat  3360
taatcttaat  tcttgatgtt  ttgtgattaa  taataggaat  ggagttactt  acgtggagga  3420
ttaacaacta  ttgatagaga  ttacggaatt  ttcaacaaca  ttcatcacga  cattggaact  3480
```

-continued

```
cacgtgatcc atcatctttt cccacaaatc cctcactatc acttggtcga tgctgtgagt    3540
catctcactc tctggctact ttcatcaaaa ccatttgatt aaagggtgat taattactaa    3600
tgtagtgatt ttaacaaatg gaatgtgaca gacaaaagca gctaaacatg tgttgggaag    3660
atactacaga gaaccaaaga cgtcaggagc aataccgatc cacttggtgg agagtttggt    3720
agcaagtatt aagaaagatc attacgtcag tgacactggt gacattgtct tctacgagac    3780
tgatccagat ctctacgttt atgcttctgt caaatcgaaa atcaattaa              3829
```

<210> SEQ ID NO 4
<211> LENGTH: 46
<212> TYPE: DNA
<213> ORGANISM: Artificial Sequence
<220> FEATURE:
<223> OTHER INFORMATION: exon 3, intron 3 border of gene encoding a
      fatty acid desaturase

<400> SEQUENCE: 4

```
atgttgaaaa cgacgagtct tgggttccgg taatccccct ctcata              46
```

<210> SEQ ID NO 5
<211> LENGTH: 46
<212> TYPE: DNA
<213> ORGANISM: Artificial Sequence
<220> FEATURE:
<223> OTHER INFORMATION: exon 3, intron 3 border of gene encoding a
      fatty acid desaturase

<400> SEQUENCE: 5

```
atgttgaaaa cgacgagtct tgggttccgg taatccccct ctcatg              46
```

<210> SEQ ID NO 6
<211> LENGTH: 50
<212> TYPE: DNA
<213> ORGANISM: Artificial Sequence
<220> FEATURE:
<223> OTHER INFORMATION: exon 3, intron 3 border of gene encoding a
      fatty acid desaturase

<400> SEQUENCE: 6

```
atgttgaaaa cgacgagtct tgggttccgg taatctttcc ctctctcata          50
```

<210> SEQ ID NO 7
<211> LENGTH: 50
<212> TYPE: DNA
<213> ORGANISM: Artificial Sequence
<220> FEATURE:
<223> OTHER INFORMATION: exon 3, intron 3 border of gene encoding a
      fatty acid desaturase

<400> SEQUENCE: 7

```
atgttgaaaa cgacgagtct tgggttccgg taacatttcc ctctttaata          50
```

<210> SEQ ID NO 8
<211> LENGTH: 50
<212> TYPE: DNA
<213> ORGANISM: Artificial Sequence
<220> FEATURE:
<223> OTHER INFORMATION: exon 3, intron 3 border of gene encoding a
      fatty acid desaturase

<400> SEQUENCE: 8

```
atgttgaaaa cgacgagtct tgggttccag taacatttcc ctctttaata          50
```

<210> SEQ ID NO 9
<211> LENGTH: 497
<212> TYPE: DNA
<213> ORGANISM: Brassica napus

<400> SEQUENCE: 9

```
gaccagcgta gcaatgcgaa cggagacgaa aggtttgatc cgagcgcaca accaccgttc      60
aagatcggag atataagggc ggccattcct aagcattgtt gagtaaagag tcctttgaga     120
tccatgagct atgtcgccag agacattttc gccgtcgtgg ctcttgccgt cgccgccgtg     180
tattttgata gctggttctt ttggcctctt tattgggccg cccaaggaac cctgttctgg     240
gctatcttcg tactcggcca cgactggtaa tttaattttt ctttcaactt cttaattttg     300
atatgtttat atgtttttt tcgttttttg cattgtcttt gatttcttga ccgcacgttc      360
gatatgagat tttcactgac ttcaagattt gattctcttc aggtttactt ttttcaaatt     420
taattattat tcacccaatt tggcctattt taaaagcaaa aggggatcta agattttaa      480
ttcttttgtt ttttttt                                                    497
```

<210> SEQ ID NO 10
<211> LENGTH: 349
<212> TYPE: DNA
<213> ORGANISM: Brassica napus

<400> SEQUENCE: 10

```
cgtagcaatg tgaacggaga ttccaaggac gaaaggtttg atccgagcgc acaaccaccg      60
tttaagatcg gagatataag ggctgcgatt cctaagcatt gttgggtcaa gagtcctttg     120
agatccatga gctacgtcgc gagagacatt ttctccgtcg tggctctggc cgtcgccgcc     180
gtgtattttg atagctggtt cttctagcct ctttattggg ccgcccaagg aaccccttttc    240
tgggccatct tcgtactcgg ccacgactgg taatttaatt ttcaatttat tttttcttca    300
acttcttaat tttgatatgt ttatatgttt ttttcgtttg catcggtgt                 349
```

<210> SEQ ID NO 11
<211> LENGTH: 36
<212> TYPE: PRT
<213> ORGANISM: Artificial Sequence
<220> FEATURE:
<223> OTHER INFORMATION: portion of fatty acyl-acyl-ACP thioesterase A2
      protein

<400> SEQUENCE: 11

Leu Glu Asp Pro Ala Gln Tyr Ser Met Leu Glu Leu Lys Pro Arg Arg
 1               5                  10                  15

Ala Asp Leu Asp Met Asn Gln His Val Asn Asn Val Thr Tyr Ile Gly
             20                  25                  30

Trp Val Leu Glu
         35

<210> SEQ ID NO 12
<211> LENGTH: 367
<212> TYPE: PRT
<213> ORGANISM: Arabidopsis thaliana

<400> SEQUENCE: 12

Met Leu Lys Leu Ser Cys Asn Val Thr Asp His Ile His Asn Leu Phe
 1               5                  10                  15

Ser Asn Ser Arg Arg Ile Phe Val Pro Val His Arg Gln Thr Arg Pro
             20                  25                  30

```
Ile Ser Cys Phe Gln Leu Lys Lys Glu Pro Leu Arg Ala Ile Leu Ser
        35                  40                  45

Ala Asp His Gly Asn Ser Ser Val Arg Val Ala Asp Thr Val Ser Gly
 50                  55                  60

Thr Ser Pro Ala Asp Arg Leu Arg Phe Gly Arg Leu Met Glu Asp Gly
65                  70                  75                  80

Phe Ser Tyr Lys Glu Lys Phe Ile Val Arg Ser Tyr Glu Val Gly Ile
                85                  90                  95

Asn Lys Thr Ala Thr Ile Glu Thr Ile Ala Asn Leu Leu Gln Glu Val
                100                 105                 110

Ala Cys Asn His Val Gln Asn Val Gly Phe Ser Thr Asp Gly Phe Ala
            115                 120                 125

Thr Thr Leu Thr Met Arg Lys Leu His Leu Ile Trp Val Thr Ala Arg
        130                 135                 140

Met His Ile Glu Ile Tyr Lys Tyr Pro Ala Trp Ser Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Cys Ala Thr Gly Glu Val Ile Gly Arg Ala Thr
            180                 185                 190

Ser Lys Trp Val Met Met Asn Gln Asp Thr Arg Arg Leu Gln Arg Val
        195                 200                 205

Thr Asp Glu Val Arg Asp Glu Tyr Leu Val Phe Cys Pro Pro Glu Pro
210                 215                 220

Arg Leu Ala Phe Pro Glu Glu Asn Asn Ser Ser Leu Lys Lys Ile Pro
225                 230                 235                 240

Lys Leu Glu Asp Pro Ala Gln Tyr Ser Met Leu Gly Leu Lys Pro Arg
                245                 250                 255

Arg Ala Asp Leu Asp Met Asn Gln His Val Asn Asn Val Thr Tyr Ile
            260                 265                 270

Gly Trp Val Leu Glu Ser Ile Pro Gln Glu Ile Ile Asp Thr His Glu
        275                 280                 285

Leu Lys Val Ile Thr Leu Asp Tyr Arg Arg Glu Cys Gln Gln Asp Asp
    290                 295                 300

Ile Val Asp Ser Leu Thr Thr Ser Glu Thr Pro Asn Glu Val Val Ser
305                 310                 315                 320

Lys Leu Thr Gly Thr Asn Gly Ser Thr Thr Ser Lys Arg Glu His
                325                 330                 335

Asn Glu Ser His Phe Leu His Ile Leu Arg Leu Ser Asn Gly Gln
            340                 345                 350

Glu Ile Asn Arg Gly Arg Thr Gln Trp Arg Lys Lys Ser Ser Arg
        355                 360                 365

<210> SEQ ID NO 13
<211> LENGTH: 223
<212> TYPE: PRT
<213> ORGANISM: Brassica napus

<400> SEQUENCE: 13

Gly Phe Ser Thr Asp Gly Phe Ala Thr Thr Leu Thr Met Arg Lys Leu
 1               5                  10                  15

His Leu Ile Trp Val Thr Ala Arg Met His Ile Glu Ile Tyr Lys Tyr
                20                  25                  30

Pro Ala Trp Ser Asp Val Val Glu Ile Glu Thr Trp Cys Gln Ser Glu
                35                  40                  45
```

```
Gly Arg Ile Gly Thr Arg Arg Asp Trp Ile Leu Arg Asp Ser Ala Thr
 50                  55                  60

Asn Glu Val Ile Gly Arg Ala Thr Ser Lys Trp Val Met Met Asn Gln
 65                  70                  75                  80

Asp Thr Arg Arg Leu Gln Arg Val Thr Asp Glu Val Arg Asp Glu Tyr
                 85                  90                  95

Leu Val Phe Cys Pro Arg Glu Pro Arg Leu Ala Phe Pro Glu Glu Asn
                100                 105                 110

Asn Ser Ser Leu Lys Lys Ile Pro Lys Leu Glu Asp Pro Ala Gln Tyr
                115                 120                 125

Ser Met Leu Glu Leu Lys Pro Arg Arg Ala Asp Leu Asp Met Asn Gln
130                 135                 140

His Val Asn Asn Val Thr Tyr Ile Gly Trp Val Leu Glu Ser Ile Pro
145                 150                 155                 160

Gln Glu Ile Ile Asp Thr His Glu Leu Gln Val Ile Thr Leu Asp Tyr
                165                 170                 175

Arg Arg Glu Cys Gln Gln Asp Asp Ile Val Asp Ser Leu Thr Thr Ser
                180                 185                 190

Glu Ile Pro Asp Asp Pro Ile Ser Lys Leu Thr Gly Thr Asn Gly Ser
                195                 200                 205

Ala Thr Ser Ser Ile Gln Gly His Asn Glu Ser Gln Phe Leu His
210                 215                 220

<210> SEQ ID NO 14
<211> LENGTH: 1164
<212> TYPE: DNA
<213> ORGANISM: Brassica napus

<400> SEQUENCE: 14
aagtgtggat tctcgacgga tggatttgcc acaacactca ccatgaggaa attgcatctc      60
atatgggtca ctgcaagaat gcacattgag atctacaagt acccagcttg gtattttctt     120
ttcttaggct tctttgacta gttgacactt tagaggtcgg agtttgtaaa cctcagagct     180
ttttattact tggttaacag gagtgatgtt gttgagatag agacatggtg ccagagtgaa     240
ggaaggattg gaacgagacg tgattggatt ctaagggact ctgctacaaa tgaagttatt     300
gggcgtgcta caaggtttgc caaaaacaga tttgttacta ctattcataa attcattttt     360
ttatctgcct tcaatcaata taataatgca aatcactgac attagtcgca caacagtaac     420
tcccatatac gttgcttatt tagttataaa gacttatgca tattctggaa cctgagcttg     480
tttttgtttg acaaatgtta catgggtctt acagcaagtg ggtgatgatg aaccaagaca     540
caaggcggct tcaaagagtt acagatgaag ttcgggacga gtacttggtt ttctgtcctc     600
gagaacccag gtgaagaaga atcatcatgc ttcccttata attgctagtt aaacagttaa     660
tatttaagca tgtggatctc aacctgttgt cctctgtatt tctcgtagac tagcgtttcc     720
agaagagaac aatagcagct taagaaaat cccaaaacta aagatccag ctcagtattc       780
tatgctagag cttaagcttc ggcgagctga tctggacatg aaccagcacg tgaataacgt     840
cacctacatt ggatgggtgc ttgaggtgag taccttaata aagcctacaa aacgtctatc     900
atttttaatca tacatatgag ctaactaact attaaatttg agtttggttc cctggtaatg    960
gcagagcata cctcaagaaa tcattgatac gcatgagctt caagttataa ctctagatta    1020
cagaagagaa tgccagcaag atgacattgt agattcactc accacctctg aaatccctga    1080
cgacccgatc tcaaagctta ccgggaccaa cggatctgcc acgtcaagca tacaaggaca    1140
```

-continued caatgagagc cagttcttgc atat                                          1164

<210> SEQ ID NO 15
<211> LENGTH: 1163
<212> TYPE: DNA
<213> ORGANISM: Brassica napus

<400> SEQUENCE: 15
aagtgtggat tctcgacgga tggatttgcc acaacactca ccatgaggaa attgcatctc     60
atatgggtca ctgcaagaat gcacattgag atctacaagt acccagcttg gtatttctt    120
ttcttaggct tctttgacta gttgacactt tagaggtcgg agtttgtaaa cctcagagct    180
ttttattact tggttaacag gagtgatgtt gttgagatag agacatggtg ccagagtgaa    240
ggaaggattg gaacgagacg tgattggatt ctaaggact  ctgctacaaa tgaagttatt    300
gggcgtgcta caaggtttgc caaaaacaga tttgttacta ctattcataa attcattttt    360
ttatctgcct tcaatcaata taataatgca aatcactgac attagtcgca caacagtaac    420
tcccatatac gttgcttatt tagttataaa gacttatgca tattctggaa cctgagcttg    480
tttttgtttg acaaatgtta catgggtctt acagcaagtg ggtgatgatg aaccaagaca    540
caaggcggct tcaaagagtt acagatgaag ttcgggacga gtacttggtt ttctgtcctc    600
gagaacccag gtgaagaaga gtcatcatgc ttcccttata attgctagtt aaacagttaa    660
tatttaagca tgtggatctc aacctgttgt tctctgtatt tctcgtagac tagcgtttcc    720
agaagagaac aatagcagct taagaaaaat cccaaaacta aagatccag  ctcagtattc    780
tatgctagag cttaagcttc ggcgagctga tctggacatg aaccagcacg tgaataacgt    840
cacctacatt ggatgggtgc ttgaggtgag taccttaata aagcctacaa aacgtctatc    900
attttaatca tacatatgag ctaactaact attaaatttg agtttggttc cctggtaatg    960
gcagagcata cctcaagaaa tcattgatac gcatgagctt caagttataa ctctagatta   1020
cagaagagaa tgccagcaag atgacattgt agattcactc accacctctg aaatccctga   1080
cgacccgatc tcaaagctta ccgggaccaa cggatctgcc acgtcaagca tacaaggaca   1140
caatgagagc cagttcttgc ata                                           1163

<210> SEQ ID NO 16
<211> LENGTH: 1557
<212> TYPE: DNA
<213> ORGANISM: Brassica Napus

<400> SEQUENCE: 16
atggtggcta cttgcgctac gtcgtcgttt tttcatgttc catcttcttc ctcgcttgat     60
actaatggga aggggaacag agttgggtct actaattttg ctggacttaa ctcaacgcca    120
agctctggga ggatgaaggt taagccaaac gctcaggctc cacccaagat caacgggaag    180
aaagctaact tgcctggctc tgtagagata tcaaagtctg acaacgagac ttcgcaaccc    240
gcacacgcac cgaggacgtt tatcaaccag ctacctgact ggagcatgct tcttgctgcc    300
ataacaacta ttttcttagc ggcggagaaa cagtggatga tgcttgactg gaaacctagg    360
cgttctgata tgattatgga tcctttcggt ttagggagaa tcgttcagga tggtcttgtg    420
ttccgtcaga attttttccat taggtcttat gagataggtg ctgatcgctc tgcgtctata    480
gaaactgtca tgaatcattt acaggtactg ctttgattgt ggttacactc acatgttgtc    540
ccaatagata tatgctcatg acaagctctt atgctaatga caggaaacgg cgcttaatca    600

| | |
|---|---|
| tgtgaagtct gccggactgc tggaaaatgg gtttgggtcc actcctgaga tgtttaagaa | 660 |
| gaatttgata tgggtcgttg ctcgtatgca ggttgtcgtt gataaatatc ctacttggta | 720 |
| agccattgtt agtcttagca cttgacttaa aatcattttg catattacag tgtgcgtaga | 780 |
| tcatttgctt attcaaatat ctgactcaca ggggagatgt tgtggaagtg gatacttggg | 840 |
| ttagtcagtc tggaaagaat ggtatgcgtc gtgattggct agttcgggat tgcaatactg | 900 |
| gagaaattgt aacgcgagca tcaaggtcag agttcttata ttttggttta ctccagctat | 960 |
| tatcgttttg ctctctgttt gtattgtttc ctctgccatt agtttgataa ttgagtcttt | 1020 |
| atagttgtat atgtatggca attttcttct ttttgcagtt tgtgggtgat gatgaataaa | 1080 |
| ctcacaagga gattgtcaaa gattcctgaa gaggttcgag gggaaataga gccttatttt | 1140 |
| gtgaactctg atcctgtcat tgccgaagac agcagaaagt taacaaaact tgatgacaag | 1200 |
| actgctgact atgttcgttc tggtctcact gtaagtacct tacctttcga caagcctgtc | 1260 |
| aaaactcttg aggttctaat ggtttggtaa tgaactttt tttggcagcc gaggtggagt | 1320 |
| gacttggatg ttaaccagca tgttaacaat gtaaagtaca ttgggtggat actgagagt | 1380 |
| gctccagcag ggatgctgga gagtcagaag ctgaaaagca tgactctgga gtatcgcagg | 1440 |
| gagtgcggga gagacagtgt gcttcagtct ctcaccgcag tctctggatg tgatgtcggt | 1500 |
| aacctcggga cagccgggga agtggagtgt cagcatttgc ttcgactcca ggatgga | 1557 |

<210> SEQ ID NO 17
<211> LENGTH: 1563
<212> TYPE: DNA
<213> ORGANISM: Brassica Napus

<400> SEQUENCE: 17

| | |
|---|---|
| atggtggcca cctcagctac atcctcattc ttccctctcc catctttccc cctcgacccc | 60 |
| accgcaaaaa ccaacaaagt caccacctcc accaacttct ccggcctctc ccccactcca | 120 |
| aactcctccg gcaggatgaa ggttaaacca acgctcagg ccccacccaa gatcaacggc | 180 |
| aagagagtcg gtctcccttc tggctcggtg aagcctgata acgagacgtc ctcacagcat | 240 |
| cccgcagcac cgaggacgtt catcaaccag ctgcctgact ggagcatgct tcttgctgca | 300 |
| ataacaaccg tcttcttggc ggctgagaag cagtggatga tgcttgactg gaaaccgagg | 360 |
| cgctctgacg tgattatgga tccgtttggg ttagggagga tcgttcagga tgggcttgtg | 420 |
| ttccgtcaga atttctctat tcggtcttat gagataggtg ctgatcgctc tgcgtctata | 480 |
| gaaacggtta tgaatcattt acaggtactg attatgatta tgattatgat tgtagttgct | 540 |
| tgttgttact ggacaaagtt aatatgtatt gctgttatgg ttatgatagg aaacggcact | 600 |
| caaccatgtt aagactgctg gactgcttgg agatgggttt ggttctactc ctgagatggt | 660 |
| taagaagaac ttgatttggg ttgttactcg tatgcaggtt gtcgttgata aatatcctac | 720 |
| ttggtaagct attctcaagc aaccctgaga atcactgctt cctttgtcat ttgcttattc | 780 |
| aaatatctgt ctcacagggg agatgttgtg gaagtagata catgggtgag ccagtctgga | 840 |
| aagaacggta tgcgtcgtga ttggctagtt cgagatggca atactggaga aattttaaca | 900 |
| agagcatcaa ggttagattt ttattatcg gttaggtatc tgaaaatttg agttactaat | 960 |
| gcaaaatatt attttttgcag tgtgtgggtg atgatgaata aactgacaag aagattatca | 1020 |
| aagattcctg aagaggttcg aggggagata gagccttact tgttaattc agacccagtc | 1080 |
| cttgctgagg acagcagaaa gttaactaaa cttgatgaca agactgctga ctatgttcgt | 1140 |
| tctggtctca ctgtaagtat gcatactttc tctatgtttc atcaaagcct gtaaacttct | 1200 |

```
gagattctta cagttttat ttggtaattt aaacttttgc agccgcgttg gagtgacttg    1260
gatgttaacc agcacgttaa caatgtgaag tacatcgggt ggatactgga gagtgcacct    1320
gtggggatga tggagagtca gaagctgaaa agcatgactc tggagtatcg cagggagtgc    1380
gggagggaca gtgtgcttca gtccctcacc gcggtttcgg gctgcgatgt tggtagtctt    1440
gggacagctg gtgaagtgga atgtcagcac ctgctccgtc tccaggatgg agctgaagtg    1500
gtgagaggaa gaacagagtg gagttccaaa acatcaacaa caacttggga cattacaccg    1560
tga                                                                 1563
```

<210> SEQ ID NO 18
<211> LENGTH: 1572
<212> TYPE: DNA
<213> ORGANISM: Brassica Napus

<400> SEQUENCE: 18

```
atggtggcca cctcagctac atcctcattc ttccctctcc catcttcccc cctcgacccc      60
accgcaaaaa ccaacaaagt caccacctcc accaacttct ccggcctcac acccacgccg     120
aactccgcca ggatgaaggt taaaccaaac gctcaggccc cacccaagat caacggcaag     180
agagtcggcc tccctggctc ggtggagatc ttgaagcctg atagcgagac ttcgcaacca     240
gcaccgagga cgttcatcaa ccagctgcct gactggagca tgctcctcgc cgccatcacg     300
accgtcttct tggcggctga gaagcagtgg atgatgctcg actggaaacc gaggcgttct     360
gacgtgatta tggatccgtt tgggttaggg aggatcgttc aggatgggct tgtgttccgt     420 cagaatttt ctattcggtc ttatgagata ggtgctgatc gctctgcgtc tatagaaacg     480
gttatgaatc atttacaggt actgattatg attatgattg tagtcgcttg ttgttactgg     540
acaaacttaa atatgtattg ctcttatggt tgtgatagga aacggcactc aaccatgtta     600
agactgctgg gctgcttgga gatgggtttg gttctactcc tgagatggtt aagaagaact     660
tgatatgggt tgttactcgt atgcaggttg tcgttgataa atatcctact tggtaagcta     720
ttctcaaaca actctgagaa tcactgcttc ctttgtgagt catttgctta ttcaaatatc     780
tgcctcatag gggagatgtt gtggaagtag atacatgggt gagccagtct ggaaagaacg     840
gtatgcgtcg tgattggctt gttcgggatg gcaatactgg agagatttta acaagagcat     900
caaggttaga ttttattttt tggtttactt gggttagata tctgataatt gagttataat     960
catctccgtg ttgtgtaaac tattctttt gcagtgtgtg ggtgatgatg aataaactga    1020
caagaagatt atcaaagatt cctgaagagg ttcgaggga gatagagcct tacttttgtta    1080 actcagaccc agtccttgcc gaggacagca gaaagttaac aaaacttgat gacaaaactg    1140
ctgtctatgt tcgttctggt ctcactgtaa gtacaaatac ttcactctat gtttcaacaa    1200
agcctgtaaa ttttttgagtc tcttacaggt ttggtaatga cttttttgca gccgcgttgg    1260
agtgacttgg atgttaacca gcacgttaac aatgtgaagt acatcgggtg gatactggag    1320
agtgctccag tggggatgat ggagagtcag aagctgaaaa gcatgactct ggagtatcgc    1380
agggagtgtg ggagagacag tgtgctccag tccctcaccg cggtttcggg ctgcgatatc    1440
ggtagcctcg gacagccgg tgaagtgaa tgtcagcatc tgctcagact ccaggatgga    1500
gccgaagtgg tgagaggaag aacagagtgg agttccaaaa catcaacaac aacttgggac    1560
atcacaccgt ga                                                        1572
```

<210> SEQ ID NO 19

<211> LENGTH: 1664
<212> TYPE: DNA
<213> ORGANISM: Brassica Napus

<400> SEQUENCE: 19

| | | | | |
|---|---|---|---|---|
| atggtggcta | cttccgctac | gtcgtcgttt | tttcatgttc | catcttcctc | ctctcttgat | 60 |
| actaatggga | aggggaacag | agttgcgtcc | acgaacttcg | ctggacttaa | ctcaacgcca | 120 |
| agctctggga | ggatgaaggt | taaaccaaac | gctcaggctc | cacccaagat | caacgggaag | 180 |
| aaagctaact | tgcctggttc | tgcagagata | tcaaagtctg | acaacgagac | ttcgcaaccc | 240 |
| gcacccgcac | cgaggacgtt | tatcaaccag | ctgcctgact | ggagcatgct | tctcgctgcc | 300 |
| ataacaacta | ttttcttagc | ggctgagaaa | cagtggatga | tgcttgactg | gaaacccagg | 360 |
| cgttctgata | tgataatgga | tcctttcggt | ttagggagaa | tcgttcagga | tggtcttgtg | 420 |
| tttcgtcaga | atttctccat | taggtcttat | gagataggtg | ctgatcgctc | tgcgtctata | 480 |
| gaaactgtta | tgaatcattt | acaggtaggt | actactttga | ttgttatcac | acttgtcact | 540 |
| ggacacccaa | tagatatata | tgctcatgac | aagctcttat | gctaatgaca | ggaaacggcc | 600 |
| ctaaaccatg | tgaagtctgc | cggactgctg | aaaatgggt | ttggttctac | tcccgagatg | 660 |
| tttaagaaga | acttgatatg | ggtcgttgct | cgtatgcagg | ttgtcgttga | taaatatcct | 720 |
| acttggtaag | ccattgtcag | tcttaccact | taacttaaaa | tcattatgca | tattacagtt | 780 |
| tgcatagatc | attacttatt | caaatatctg | actaacaggg | gagatgttgt | ggaagtggat | 840 |
| acatgggtta | gtcagtccgg | aaagaatggt | atgcgtcgtg | attggctggt | tcgggattgc | 900 |
| aatactggag | aaattgtaac | gcgagcatca | aggtcagagt | tcttatgttt | tggtttactg | 960 |
| actccagcta | ttatcatttt | gctctctgtt | tgtattgttt | gctctgccat | aatatgata | 1020 |
| atagagactt | tatagttgta | tatgtatggc | aattttcttc | ttttttgcagt | ttgtgggtga | 1080 |
| tgatgaataa | actgacaagg | agattgtcaa | agattcctga | agaggttcgt | ggggaaatag | 1140 |
| agccttattt | tgtgaactct | gatcctgtca | ttgccaagaa | cagcagaaag | ttaacaaaac | 1200 |
| tggatgacaa | gactgctgac | tatgttcgtt | cgggtctcac | tgtaagtacc | ctacctttca | 1260 |
| acaagccttt | aaaactcttg | aggttctaat | ggtttggtaa | taaacttttt | tttcagccga | 1320 |
| gttggagtga | cttagatgtt | aaccagcatg | ttaacaatgt | aaagtacatt | gggtggatac | 1380 |
| tggagagtgc | tccagcaggg | atgctggaga | gtcagaagct | gaaaagcatg | actctggagt | 1440 |
| atcgcaggga | gtgcgggaga | gacagtgtgc | ttcagtctct | caccgcggtc | tctggatgtg | 1500 |
| atgtcggtaa | cctcgggaca | gccgggggaag | tggagtgtca | gcatttgctt | cgtctccagg | 1560 |
| atggagctga | agtggtgaga | ggaagaacag | ctgaagtggt | gagaggaaga | acagagtgga | 1620 |
| gttccaagat | agaagcaaca | acttgggaca | ctgctacatc | gtaa | 1664 |

<210> SEQ ID NO 20
<211> LENGTH: 1714
<212> TYPE: DNA
<213> ORGANISM: Brassica Napus

<400> SEQUENCE: 20

| | | | | |
|---|---|---|---|---|
| atggtggcca | cctctgctac | atcctcattc | ttccctctcc | catcttcctc | tctcgacccc | 60 |
| aatggcaaaa | ccaacaaagc | cacctccacc | aacttctccg | gactcaaccc | cacaccaaac | 120 |
| tcttccggca | ggttaaaggt | caaaccaaac | gctcaggctc | catccaagat | caacggcaag | 180 |
| aaagtctcct | tgccaggctc | agtacacatc | gtaaagacta | taataaccca | cgatctctcg | 240 |
| caacaaaacg | cacccagaac | gttcatcaac | cagctacctg | actggagcat | gcttctcgcc | 300 |

-continued

```
gccatcacaa cggtcttctt agcagctgag aagcagtgga tgatgcttga tactaaaccg    360
agacgctccg acatgattat ggatccgttt gggttaggga gaatcgttca ggatgggctt    420
gtgtaccgtc agaatttcga tatcaggtct tatgaaatag gtgctgatcg ctctgcatct    480
atagaaactg tcatgaatca cttacaggta tattacaatc acactcgttt gatactatag    540
cttgacccgc actgatgttg gttttatat ttttataaat tgtttagtga catatagata    600
taggttattt agatatttct aggttcctac gaacctaccc ggactcaaac cctgtccgta    660
aaattgagtt taattttaaa ccaaaaaaat ccgatacccg aaaaaaccga tctgtatcta    720
actcttgtcc tcatgacagg aaacggctct caaccatgtg aagtctgcag gactgctggg    780
agatgggttt ggttctacac ctgagatggt taagaagaac ttgatatggg ttgttactcg    840
tatgcaggtt gtagttgata atatcctac ttggtaagct ctcttgccac ttaaccttaa    900
acaatatgca tgaatcattt gcttattcaa atgtctgttt caccagggga gatgttgttg    960
aagtagatac atgggtcagt aagtctggga agaatggtat gctcgtgat tggctagttc    1020 gtgattgcaa tactggagaa atcttaacac gcgcatcaag gttagcttta ttttgttttt    1080
gtttactcca gctattatct gattattgag ttataaccat ctctatgtta caaaacagtg    1140
tgtgggtgat gatgaataaa ctgacaagga gattatcaaa gcttcctgaa gaggttcgag    1200
gggaaataga gccttacttt gtgaactctg acccaatcct tgccgaggac agcagaaagt    1260
taacaaagct agatgacaag actgctgact atgttcgctc tggtctcacc gtaagtataa    1320
atattcaact ctttatcttt tagcgtgtaa aactcttgag agattcttat gagtttggtg    1380
atgaactttt gcagccgaga tggagtgact tggatgttaa ccagcatgtt aacaacgtga    1440
agtacattgg ttggatactc gagagtgctc cagtagagat gatggagaag cataagctga    1500
aaagcatgac tctggagtat aggagggaat gcgggagaga cagtgtgctt cagtctctca    1560
ccgcggtttc gggatgcgat gttggtagcc tcgggacagc tggtgaagtg gaatgtcagc    1620
atttgcttcg acaccaggat ggagctgaag tggtgaaggg acgaacagtg tggagttcga    1680
aaacaccatc aacaacttgg gacactacat cgta                                1714
```

<210> SEQ ID NO 21
<211> LENGTH: 1891
<212> TYPE: DNA
<213> ORGANISM: Brassica Napus

<400> SEQUENCE: 21

```
atggtggcca cctctgctac atcctcattc ttccctctcc catcttcctc tctcgaccct     60
aatggcaaaa ccaacaaact cacctccacc aacttctctg gactcaaccc cataccaaac    120
tcttccggca ggttaaaggt caaaccaaac gcccaagctc catccaagat caacggcaat    180
aatgtctcct tgccaggctc agtacacatc gtaaagactg ataataacca cgatctctcg    240
caacaacacg cacccagaac gttcatcaac cagctacctg actggagcat gcttctcgcc    300
gccatcacaa cggtcttctt agctgctgag aaacagtgga tgatgcttga ctcgaaaccg    360
aggcgttctg atatgattat ggatccgttc gggttaggga ggatcgttca ggatgggctt    420
gtgtaccgtc agaacttcga tatcaggtct tatgaaatag gtgctgatcg ctctgcgtct    480
atagaaacag tcatgaacca cttacaggta tattacaatc acactcgatt gatactagag    540
cttgacatgt tggttttat cttttttataa attgttagt gacattttca aacatataga    600
tataggttat ttagatattt ctaggttcct acaaacctac ccagactcaa accccgtccg    660
```

-continued

```
gaaatttata atattaatac cgaacagagt tttattttaa accaaaaaat cagttgaccc      720
gcacgggatg ttggttttta tctattttat acattgttta aggacatttt taaacatata      780
aatataggtt atttagatat ttctaggttc ctacgaacct acccggaaat ttataatacc      840
cgaacatagt ttaattttta aaccaaaaaa tccaataccc gaaaaaacca atctgtgata      900
tgcatgatct aactcttgtc ctcgtgacag gaaacggctc tcaaccatgt gaagtctgct      960
ggactgctgg gagatgggtt tggttctacc cctgagatgg ttaagaagaa cttgatatgg     1020
gtcgttactc gtatgcaggt tgtcgttgat aaatatccta cttggtaagc cctcttagca     1080
cttaacctta aaacaatatg catgaatcat ttgcttattc aaatgtctgc ttccaccaggg    1140 gagatgttgt tgaagtagat acatgggtta gtaagtctgg aagartggt atgcgtcgtg      1200 attggcttgt tcgggattgt aatactggag aaattttaac aagagcatca aggttagctt     1260 cttttttgttt actccagcta ttatctgatt attgagttat aaccatctct gtgttgcaaa    1320
acagtgtgtg ggtgatgatg aataaagtga caaggagatt atcaaagctt cctgaagagg    1380
ttcgagggga aatagagcct tactttgtga actctgaccc tatccttgcc gaggacagca     1440
gaaagttaac aaaactagat gagaagactg ctgactatgt tcgctctggt ctcaccgtaa    1500
gtataaatat ttgtttttat ctttcagcaa gtgagattct gatgggtttg gtgattatct     1560 aactttttgca gccgagatgg agtgacttgg atgttaacca gcatgttaac aacgtgaagt   1620
acattggttg gatactcgag agtgctccag tggagatgat ggagaagcat aagctgaaaa    1680
gcatgactct ggagtatagg agggaatgcg ggagagacag tgtgcttcag tctctcaccg    1740
cggtttcggg ttgcgatgtt ggtagcctcg ggacagctgg tgaagtggaa tgtcagcatt    1800
tgcttcgact ccaggatgga gctgaagtgg tgaagggacg aacagtgtgg agttccaaaa   1860
caccatcaac aacttgggac actacatcgt a                                   1891
```

<210> SEQ ID NO 22
<211> LENGTH: 1557
<212> TYPE: DNA
<213> ORGANISM: Brassica Napus

<400> SEQUENCE: 22

```
atggtggcta cttgcgctac gtcgtcgttt tttcatgttc catcttcttc ctcgcttgat      60
actaatggga aggggaacag agttgggtct actaattttg ctggacttaa ctcaacgcca      120
agctctggga ggatgaaggt taagccaaac gcttaggctc cacccaagat caacgggaag      180
aaagctaact tgcctggctc tgtagagata tcaaagtctg acaacgagac ttcgcaaccc      240
gcacacgcac cgaggacgtt tatcaaccag ctacctgact ggagcatgct tcttgctgcc      300
ataacaacta ttttcttagc ggcggagaaa cagtggatga tgcttgactg gaaacctagg     360
cgttctgata tgattatgga tcctttcggt ttagggagaa tcgttcagga tggtcttgtg     420
ttccgtcaga atttttccat taggtcttat gagataggtg ctgatcgctc tgcgtctata     480
gaaactgtca tgaatcattt acaggtactg ctttgattgt ggttacactc acatgttgtc    540
ccaatagata tatgctcatg acaagctctt atgctaatga caggaaacgg cgcttaatca     600
tgtgaagtct gccggactgc tggaaaatgg gtttgggtcc actcctgaga tgtttaagaa     660
gaatttgata tgggtcgttg ctcgtatgca ggttgtcgtt gataaatatc ctacttggta    720
agccattgtt agtcttagca cttgacttaa aatcattttg catattacag gtgcgtaga    780 tcatttgctt attcaaatat ctgactcaca ggggagatgt tgtggaagtg gatacttggg    840
ttagtcagtc tggaaagaat ggtatgcgtc gtgattggct agttcgggat tgcaatactg    900
```

| | |
|---|---|
| gagaaattgt aacgcgagca tcaaggtcag agttcttata ttttggttta ctccagctat | 960 |
| tatcgttttg ctctctgttt gtattgtttc ctctgccatt agtttgataa ttgagtcttt | 1020 |
| atagttgtat atgtatggca attttcttct ttttgcagtt tgtgggtgat gatgaataaa | 1080 |
| ctcacaagga gattgtcaaa gattcctgaa gaggttcgag gggaaataga gccttatttt | 1140 |
| gtgaactctg atcctgtcat tgccgaagac agcagaaagt taacaaaact tgatgacaag | 1200 |
| actgctgact atgttcgttc tggtctcact gtaagtacct tacctttcga caagcctgtc | 1260 |
| aaaactcttg aggttctaat ggtttggtaa tgaactttt tttggcagcc gaggtggagt | 1320 |
| gacttggatg ttaaccagca tgttaacaat gtaaagtaca ttgggtggat actggagagt | 1380 |
| gctccagcag ggatgctgga gagtcagaag ctgaaaagca tgactctgga gtatcgcagg | 1440 |
| gagtgcggga gagacagtgt gcttcagtct ctcaccgcag tctctggatg tgatgtcggt | 1500 |
| aacctcggga cagccgggga agtggagtgt cagcatttgc ttcgactcca ggatgga | 1557 |

<210> SEQ ID NO 23
<211> LENGTH: 1572
<212> TYPE: DNA
<213> ORGANISM: Brassica Napus

<400> SEQUENCE: 23

| | |
|---|---|
| atggtggcca cctcagctac atcctcattc ttccctctcc catcttcccc cctcgacccc | 60 |
| accgcaaaaa ccaacaaagt caccacctcc accaacttct ccggcctcac acccacgccg | 120 |
| aactccgcca ggatgaaggt taaaccaaac gctcaggccc cacccaagat caacggcaag | 180 |
| agagtcggcc tccctggctc ggtggagatc ttgaagcctg atagcgagac ttcgcaacca | 240 |
| gcaccgagga cgttcatcaa ccagctgcct gactggagca tgctcctcgc cgccatcacg | 300 |
| accgtcttct tggcggctga gaagcagtgg atgatgctcg actggaaacc gaggcgttct | 360 |
| gacgtgatta tggatccgtt tgggttaggg aggatcgttc aggatgggct tgtgttccgt | 420 |
| cagaattttt ctattcggtc ttatgagata ggtgctgatc gctctgcgtc tatagaaacg | 480 |
| gttatgaatc atttacaggt actgattatg attatgattg tagtcgcttg ttgttactgg | 540 |
| acaaacttaa atatgtattg ctcttatggt tgtgatagga acggcactc aaccatgtta | 600 |
| agactgctgg gctgcttgga gatgggtttg gttctactcc tgagatggtt aagaagaact | 660 |
| tgatatgggt tgttactcgt atgtaggttg tcgttgataa atatcctact tggtaagcta | 720 |
| ttctcaaaca actctgagaa tcactgcttc cttgtgagt catttgctta ttcaaatatc | 780 |
| tgcctcatag gggagatgtt gtggaagtag atacatgggt gagccagtct ggaaagaacg | 840 |
| gtatgcgtcg tgattggctt gttcgggatg gcaatactgg agagatttta acaagagcat | 900 |
| caaggttaga tttatttttt tggtttactt gggttagata tctgataatt gagttataat | 960 |
| catctccgtg ttgtgtaaac tattcttttt gcagtgtgtg ggtgatgatg aataaactga | 1020 |
| caagaagatt atcaaagatt cctgaagagg ttcgaggga gatagagcct tactttgtta | 1080 |
| actcagaccc agtccttgcc gaggacagca gaaagttaac aaaacttgat gacaaaactg | 1140 |
| ctgtctatgt tcgttctggt ctcactgtaa gtacaaatac ttcactctat gtttcaacaa | 1200 |
| agcctgtaaa ttttgagtc tcttacaggt ttggtaatga cttttttgca gccgcgttgg | 1260 |
| agtgacttgg atgttaacca gcacgttaac aatgtgaagt acatcgggtg gatactggag | 1320 |
| agtgctccag tggggatgat ggagagtcag aagctgaaaa gcatgactct ggagtatcgc | 1380 |
| agggagtgtg ggagagacag tgtgctccag tccctcaccg cggtttcggg ctgcgatatc | 1440 |

```
ggtagcctcg ggacagccgg tgaagtggaa tgtcagcatc tgctcagact ccaggatgga    1500
gccgaagtgg tgagaggaag aacagagtgg agttccaaaa catcaacaac aacttgggac    1560
atcacaccgt ga                                                        1572

<210> SEQ ID NO 24
<211> LENGTH: 1500
<212> TYPE: DNA
<213> ORGANISM: Brassica Napus

<400> SEQUENCE: 24
atggtggcca cctcagctac atcctcattc ttccctctcc catcttcccc cctcgacccc     60
accgcaaaaa ccaacaaagt caccacctcc accaacttct ccggcctcac acccacgccg    120
aactccgcca ggatgaaggt taaaccaaac gctcaggccc acccaagat caacggcaag     180 agagtcggcc tccctggctc ggtggagatc ttgaagcctg atagcgagac ttcgcaacca    240
gcaccgagga cgttcatcaa ccagctgcct gactgaagca tgctcctcgc cgccatcacg    300
accgtcttct tggcggctga gaagcagtgg atgatgctcg actggaaacc gaggcgttct    360
gacgtgatta tggatccgtt tgggttaggg aggatcgttc aggatgggct tgtgttccgt    420
cagaattttt ctattcggtc ttatgagata ggtgctgatc gctctgcgtc tatagaaacg    480
gttatgaatc atttacaggt actgattatg attatgattg tagtcgcttg ttgttactgg    540
acaaacttaa atatgtattg ctcttatggt tgtgatagga acggcactc aaccatgtta     600 agactgctgg gctgcttgga gatgggtttg gttctactcc tgagatggtt aagaagaact    660
tgatatgggt tgttactcgt atgcaggttg tcgttgataa atatcctact tggtaagcta    720
ttctcaaaca actctgagaa tcactgcttc ctttgtgagt catttgctta ttcaaatatc    780
tgcctcatag gggagatgtt gtggaagtag atacatgggt gagccagtct ggaaagaacg    840
gtatgcgtcg tgattggctt gttcgggatg gcaatactgg agagatttta caagagcat    900 caaggttaga ttttatttt tggtttactt gggttagata tctgataatt gagttataat    960
catctccgtg ttgtgtaaac tattctttt gcagtgtgtg ggtgatgatg aataaactga   1020
caagaagatt atcaaagatt cctgaagagg ttcgaggga gatagagcct tactttgtta    1080
actcagaccc agtccttgcc gaggacagca gaaagttaac aaaacttgat gacaaaactg    1140
ctgtctatgt tcgttctggt ctcactgtaa gtacaaatac ttcactctat gtttcaacaa    1200
agcctgtaaa ttttttgagtc tcttacaggt ttggtaatga acttttttgca gccgcgttgg    1260 agtgacttgg atgttaacca gcacgttaac aatgtgaagt acatcgggtg gatactggag    1320
agtgctccag tggggatgat ggagagtcag aagctgaaaa gcatgactct ggagtatcgc    1380
agggagtgtg ggagagacag tgtgctccag tccctcaccg cggtttcggg ctgcgatatc    1440
ggtagcctcg ggacagccgg tgaagtggaa tgtcagcatc tgctcagact ccaggatgga    1500

<210> SEQ ID NO 25
<211> LENGTH: 1664
<212> TYPE: DNA
<213> ORGANISM: Brassica Napus

<400> SEQUENCE: 25
atggtggcta cttccgctac gtcgtcgttt tttcatgttc catcttcctc ctctcttgat     60
actaatggga aggggaacag agttgcgtcc acgaacttcg ctggacttaa ctcaacgcca    120
agctctggga ggatgaaggt taaaccaaac gctcaggctc acccaagat caacgggaag     180 aaagctaact tgcctggttc tgcagagata tcaaagtctg acaacgagac ttcgcaaccc    240
```

```
gcacccgcac cgaggacgtt tatcaaccag ctgcctgact ggagcatgct tctcgctgcc      300
ataacaacta ttttcttagc ggctgagaaa cagtgaatga tgcttgactg gaaacccagg      360
cgttctgata tgataatgga tcctttcggt ttagggagaa tcgttcagga tggtcttgtg      420
tttcgtcaga atttctccat taggtcttat gagataggtg ctgatcgctc tgcgtctata      480
gaaactgtta tgaatcattt acaggtaggt actactttga ttgttatcac acttgtcact      540
ggacacccaa tagatatata tgctcatgac aagctcttat gctaatgaca ggaaacggcc      600
ctaaaccatg tgaagtctgc cggactgctg aaaatgggt ttggttctac tcccgagatg       660
tttaagaaga acttgatatg ggtcgttgct cgtatgcagg ttgtcgttga taaatatcct      720
acttggtaag ccattgtcag tcttaccact aacttaaaa tcattatgca tattacagtt       780
tgcatagatc attacttatt caaatatctg actaacaggg gagatgttgt ggaagtggat      840
acatgggtta gtcagtccgg aaagaatggt atgcgtcgtg attggctggt cgggattgc       900 aatactggag aaattgtaac gcgagcatca aggtcgagt tcttatgttt tggtttactg       960
actccagcta ttatcatttt gctctctgtt tgtattgttt gctctgccat taatatgata     1020
atagagactt tatagttgta tatgtatggc aattttcttc ttttgcagt ttgtgggtga      1080 tgatgaataa actgacaagg agattgtcaa agattcctga agaggttcgt ggggaaatag     1140
agccttattt tgtgaactct gatcctgtca ttgccgaaga cagcagaaag ttaacaaaac     1200
tggatgacaa gactgctgac tatgttcgtt cgggtctcac tgtaagtacc ctacctttca     1260
acaagccttt aaaactcttg aggttctaat ggtttggtaa taaactttttt tttcagccga    1320 gttggagtga cttagatgtt aaccagcatg ttaacaatgt aaagtacatt gggtggatac     1380
tggagagtgc tccagcaggg atgctggaga gtcagaagct gaaaagcatg actctggagt     1440
atcgcaggga gtgcgggaga gacagtgtgc ttcagtctct caccgcggtc tctggatgtg     1500
atgtcggtaa cctcgggaca gccgggaag tggagtgtca gcatttgctt cgtctccagg      1560
atggagctga agtggtgaga ggaagaacag ctgaagtggt gagaggaaga acagagtgga     1620
gttccaagat agaagcaaca acttgggaca ctgctacatc gtaa                      1664
```

```
<210> SEQ ID NO 26
<211> LENGTH: 5
<212> TYPE: PRT
<213> ORGANISM: Artificial Sequence
<220> FEATURE:
<223> OTHER INFORMATION: amino acid motif

<400> SEQUENCE: 26

His Glu Cys Gly His
 1               5

<210> SEQ ID NO 27
<211> LENGTH: 6
<212> TYPE: PRT
<213> ORGANISM: Artificial Sequence
<220> FEATURE:
<223> OTHER INFORMATION: amino acid motif

<400> SEQUENCE: 27

Lys Tyr Leu Asn Asn Pro
 1               5

<210> SEQ ID NO 28
<211> LENGTH: 10
<212> TYPE: PRT
```

<213> ORGANISM: Artificial Sequence
<220> FEATURE:
<223> OTHER INFORMATION: amino acid motif

<400> SEQUENCE: 28

Asp Arg Asp Tyr Gly Ile Leu Asn Lys Val
1               5                   10

<210> SEQ ID NO 29
<211> LENGTH: 369
<212> TYPE: PRT
<213> ORGANISM: Brassica napus

<400> SEQUENCE: 29

Met Val Val Ala Met Asp Gln Arg Thr Asn Val Asn Gly Asp Ala Gly
1               5                   10                  15

Ala Arg Lys Glu Glu Gly Phe Asp Pro Ser Ala Gln Pro Pro Phe Lys
                20                  25                  30

Ile Gly Asp Ile Arg Ala Ala Ile Pro Lys His Cys Trp Val Lys Ser
            35                  40                  45

Pro Leu Arg Ser Met Ser Tyr Val Ala Arg Asp Ile Cys Ala Val Ala
    50                  55                  60

Ala Leu Ala Ile Ala Ala Val Tyr Phe Asp Ser Trp Phe Leu Cys Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
                100                 105                 110

Ser Val Val Gly His Ile Leu His Ser Phe Ile Leu Val Pro Tyr His
            115                 120                 125

Gly Trp Arg Ile Ser His Arg Thr His His Gln Asn His Gly His Val
    130                 135                 140

Glu Asn Asp Glu Ser Trp Val Pro Leu Pro Glu Arg Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Gly Leu Phe Ala Pro Ser Glu Arg Lys
    195                 200                 205

Leu Ile Ala Thr Ser Thr Thr Cys Trp Ser Ile Met Leu Ala Ile Leu
210                 215                 220

Ile Cys Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
            245                 250                 255

Leu His His His Gly His Asp Glu Lys Leu Pro Trp Tyr Arg Gly Lys
    260                 265                 270

Glu Trp Ser Tyr Leu Arg Gly Gly Leu Thr Thr Ile Asp Arg Asp Tyr
    275                 280                 285

Gly Ile Phe Asn Asn Ile His His Asp Ile Gly Thr His Val Ile His
290                 295                 300

His Leu Phe Pro Gln Ile Pro His Tyr His Leu Val Asp Ala Thr Lys
305                 310                 315                 320

Ala Ala Lys His Val Leu Gly Arg Tyr Tyr Arg Glu Pro Lys Thr Ser
                325                 330                 335

-continued

Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
            355                 360                 365

Asp

<210> SEQ ID NO 30
<211> LENGTH: 383
<212> TYPE: PRT
<213> ORGANISM: Brassica rapa

<400> SEQUENCE: 30

Met Val Val Ala Met Asp Gln Arg Thr Asn Val Asn Gly Asp Ala Gly
 1               5                  10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Cys Ala Val Ala
    50                  55                  60

Ala Leu Ala Ile Ala Ala Val Tyr Phe Asp Ser Trp Phe Leu Cys Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Arg Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Gly Leu Phe Ala Pro Ser Glu Arg Lys
        195                 200                 205

Leu Ile Ala Thr Ser Thr Thr Cys Trp Ser Ile Met Leu Ala Ile Leu
    210                 215                 220

Ile Cys Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Lys
305                 310                 315                 320

Ala Ala Lys His Val Leu Gly Arg Tyr Tyr Arg Glu Pro Lys Thr Ser
                325                 330                 335

```
Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
                355                 360                 365

Asp Pro Asp Leu Tyr Val Tyr Ala Ser Val Lys Ser Lys Ile Asn
                370                 375                 380

<210> SEQ ID NO 31
<211> LENGTH: 386
<212> TYPE: PRT
<213> ORGANISM: Arabidopsis thaliana

<400> SEQUENCE: 31

Met Val Val Ala Met Asp Gln Arg Thr Asn Val Asn Gly Asp Pro Gly
  1               5                  10                  15

Ala Gly Asp Arg Lys Lys Glu Glu Arg Phe Asp Pro Ser Ala Gln Pro
                 20                  25                  30

Pro Phe Lys Ile Gly Asp Ile Arg Ala Ala Ile Pro Lys His Cys Trp
             35                  40                  45

Val Lys Ser Pro Leu Arg Ser Met Ser Tyr Val Val Arg Asp Ile Ile
 50                  55                  60

Ala Val Ala Ala Leu Ala Ile Ala Ala Val Tyr Val Asp Ser Trp Phe
 65                  70                  75                  80

Leu Trp Pro Leu Tyr Trp Ala Ala Gln Gly Thr Leu Phe Trp Ala Ile
                 85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
            115                 120                 125

Pro Tyr His Gly Trp Arg Ile Ser His Arg Thr His Gln Asn His
            130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
                180                 185                 190

Lys Glu Gly Ser His Phe Asn Pro Tyr Ser Ser Leu Phe Ala Pro Ser
            195                 200                 205

Glu Arg Lys Leu Ile Ala Thr Ser Thr Thr Cys Trp Ser Ile Met Phe
210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255

Val Thr Tyr Leu His His Gly His Asp Glu Lys Leu Pro Trp Tyr
                260                 265                 270

Arg Gly Lys Glu Trp Ser Tyr Leu Arg Gly Gly Leu Thr Thr Ile Asp
            275                 280                 285

Arg Asp Tyr Gly Ile Phe Asn Asn Ile His His Asp Ile Gly Thr His
            290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
```

```
                   325                 330                 335
Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
            355                 360                 365

Tyr Glu Thr Asp Pro Asp Leu Tyr Val Tyr Ala Ser Asp Lys Ser Lys
            370                 375                 380

Ile Asn
385

<210> SEQ ID NO 32
<211> LENGTH: 4676
<212> TYPE: DNA
<213> ORGANISM: Brassica napus

<400> SEQUENCE: 32
aaacgtaaac aatttatacg accacagttc gaaaataaaa acaatttata cgaccagaaa      60
tggcaaaatg ttgttcttag catttttttt ttaactttac ttttgcgtaa aacacatttc     120
tccaatttgg tttcattgcg ttgaacgacg taacaaagta atacacctaa ccctttttt      180
tggaacatta tacccaac ccattgtaca aaagttacag ctaaattacc ctttttattc      240
ttttgataaa taaaaaaata aattattaat cattaaaaaa taatttggag tattttctca    300
atgtccatat atacatcttc tcccttata taagccaacc tcacacaccc aaaaaatcca    360
tcaaaccttt cttcaccaca tttcactgaa aggccacaca tctagagaga gaaacttcgt     420
ccaaatctct ctctccagca atggttgttg ctatggacca cgcagcaat gttaacggag     480
attccggtgc ccggaaggaa gagggtttg atccaagcga acaaccacg tttaagatcg     540
gagatatcag ggcggcgatt cctaagcatt gttgtttgag gtttaattct tttgaggtta    600
ccttttcatg ttcaattatt aaaaaaataa aataaaatat aggatctaag attttttct     660
tcatcagttc aagcatcatc actcatcagt cgtaagactc gtaacaaaat atcttctttt    720
ctataattaa tattatttcc gcatttaatg gatctacgtt ttgatgttct caaattttgt    780
ttctcttttct ctagatcccc ggaacttttta attataatta tagtatagta taatatcaag    840
aaaatatact gtttattttt tttggcaaca aatatattac tcttgtttct ttgacaagaa     900
aaaaatatat tgttttttt cttcttttg tgttccaatc tattttcgag atttagacaa     960
gtgacacgtc ataccggga tttgttacct tgttaaagag tttgggttaa acaaatgta    1020
gaaagttaa ataaaattgt gcaataaatg ataaatacgt tttatgtta aacaatgatg    1080
tgaaataaa attgaataat ggcagtggac atgggagttt ttcagacatt cctctgctga    1140
acagtgtggt tggtcacatt cttcattcat tcatcctcgt tccttaccat ggttggtaag   1200
tcatttatta actatttcca tgtaaactat tagtacttgt tttcgtattt cttacatttt   1260
cgtttgtcat tcttcttggg tgcatgctag caaactgtaa tcagtattaa ctgggaacta    1320
ccaactgttt tttttttgct agagtagcaa ttttataatt aaataagaat cctattaaac   1380
aatgcatgtg acaatatgag gttgcttttc tgttcaaaac aaatctttag aagccaatga    1440
aaaagaatcc aaaactttt tttaaatgat atgcgcctat ctattggtcc tgactcctga    1500
gttttcttac tttcttaagt ataattagat tttgatttt ttttataggt tttcactatt    1560
gttatttgtt tacatcagct tcagatatct tcgaaaaaga tttacatgca tcaatttcat   1620
gaggatttat agttttcctt ttacttattt ccgacacaat gtttagtagt aaaaagcatt   1680
aaatgttttt ttgctcaaaa aaaaaagaat gggattgtta gagcactcta ttgttagttg   1740
```

```
ttcaataaat ataccaacta aaaaaacaaa ataaatataa aatgagtgag attgttaaat    1800
cattatagag acaatttcat tttcacaaaa ataaataaat acataacttt ttataattgg    1860
ggtttgcagg agaataagcc atcggacaca ccaccagaac catggccatg ttgaaaacga    1920
cgagtcttgg gttccggtaa tctttcctac tctcgtagtt tctcttgtct tttatttat    1980
tgtttgtttt tcggaattta ttcttatgtc tatgttctta ggattctata tgtttatttt    2040
attagtttat gttttcagtc tgaggtcaga ccgaccactt gtcagatctg ttttctagct    2100
gtagtaaaaa acaatttgca agtgtaatag ttcagcataa ttgatcttgt tagagcattt    2160
ccaaaacaaa ctttataatt ttaaatatac agttttttgt tctctaaaaa agaatttaaa    2220
aattttaaag tttgagggac gaaacttcaa atttgaactt tcactactca acttcaaatt    2280
tgaaatttca tctttttat ttacattttg atcattataa ttaattatac attacattta    2340
tgattcttaa gtattttctc atttattgtt ttaattctta aatttttat acatcataaa    2400
tatttccaat ttgttttat aaattcaaat tttacacaaa aaagtaataa aaattttaaa    2460
taagatttat aatatttaa aactataatt aggcaaaaaa aatattacaa aaaaatgtaa    2520
taaaaacttt aaaataagat atatcaagac ataattatta gaaattttaa atattataac    2580
aatattaata atctggtaaa tttgctccaa aacctcaaaa atttctaaat tattgtccaa    2640
acaaatttgt ttaaccgaat atggagcatt acaaaaataa ttttatggaa tagtgtggta    2700
ttttgcttgt agttaatatt taattatgta tttctattta taattttata tatttaatgt    2760
aagatttttt taattaatat tactgtaata tttttatata tgtactagtt atttataaaa    2820
gttttataga tttgtattag ttataacaaa ataaggatc attgtgtaaa atacaaataa    2880
ttttgaaatt acgtttaaag ttttggttat gaaaaaata ctttgaaact ttaaatttag    2940
agttttgcaa actttaaaat gttagataga tagtttttt ggagatgcat ttagtggtta    3000
tggtagtaac tcagaaaatg aaaaatctat acttttatac tccctccgtt ttttaatata    3060
agtcgtttta cagttataca cgtagattaa gaaaaccatt aatttcttat attttctaga    3120
caaaaacatc attaattatt tacctaacca caattcaacc aatataaaaa tagaagatat    3180
attaccattg gtcatacaac attaattatt aataaatttt acatagaaaa ccgaaaacga    3240
catataattt ggaacaaaaa aatttctcta aaacgactta tattaaaaaa cggagggagt    3300
agtacctaac tttaacgatg gaccactat attcgagtcc ttagcataaa atgattctcc    3360
tcgaaatccg tttactttct tcattatttt ttccttttca gttttggcgt tttcgtaata    3420
cttttgtctt caatcttgaa agctattagt ataaaaactt ataaacacat cacatgcaat    3480
gaattaatac gaatacataa ccagaatgac aaattttcaa tgaatattta ataccagtaa    3540
gtactactcc gtaatagtaa tagtaatagt catattaatt ttttttttgt catcaaacaa    3600
acagtaatag taatattaat tataattatg tatttcagtt gccagaaaag ttgtacaaga    3660
acttgcccca tagtactcgg atgctcagat acactgttcc tctgcccatg ctcgcttacc    3720
cgatctatct ggtaaaaaaa aatacaattt caatttttt cttaaaatta caaatggttt    3780
tatattttga gttttaagcc aatatataaa ttaattttga ttggatttta actacagtgg    3840
tacagaagtc ctggaaaaga agggtcacat tttaaccat acagtagttt atttgctcca    3900
agcgagagga agcttattgc aacttcaaca acttgctggt ccataatgtt ggccactctt    3960
gtttatctat cgttcctcgt tggtccagtc acagttctca aagtctatgg tgttccttac    4020
attgtaagtt tcacatatta ttacaagaga tttatatatt attaataata aatttgtttt    4080
```

| | |
|---|---|
| ttgacataaa gttttggaaa attttcagat ctttgtaatg tggttggacg ctgtcacgta | 4140 |
| cttgcatcat catggtcacg atgagaagtt gccttggtac agaggcaagg taaataaatc | 4200 |
| aattttaaa aagaaatgta cagaaagcaa taatggttag tattgattaa tcttaatttt | 4260 |
| tgatgttttg catacaataa taggaatgga gttatttacg tggaggatta acaactattg | 4320 |
| atagagatta cggaatcttc aacaacatcc atcacgacat tggaactcac gtgatccatc | 4380 |
| atcttttccc acaaatccct cactatcact tggtcgatgc ggtgagtgat ctagcttttct | 4440 |
| ctctctctag tttcatttga ttaaatggtg attaattact aatttaatta atgaattgtg | 4500 |
| gacagacgag agcagctaaa catgtgttag gaagatacta cagagagccg aagacgtcag | 4560 |
| gagcaatacc gattcacttg gtggagagtt tggtcgcaag tattaaaaaa gatcattacg | 4620 |
| tcagtgacac tggtgatatt gtcttctacg agacagatcc agatctctac gtttat | 4676 |

<210> SEQ ID NO 33
<211> LENGTH: 4935
<212> TYPE: DNA
<213> ORGANISM: Brassica napus

<400> SEQUENCE: 33

| | |
|---|---|
| aaacgtaaac aatttatacg accacagttc gaaaataaaa acaatttata cgaccagaaa | 60 |
| tggcaaaatg ttgttcttag cattttttttt ttaactttac ttttgcgtaa aacacatttc | 120 |
| tccaatttgg tttcattgcg ttgaacgacg taacaaagta atacacctaa cccttttttt | 180 |
| tggaacatta tacacccaac ccattgtaca aaagttacag ctaaattacc cttttttattc | 240 |
| ttttgataaa taaaaaaata aattattaat cattaaaaaa taatttggag tattttctca | 300 |
| atgtccatat atacatcttc tcccttata taagccaacc tcacacaccc aaaaaatcca | 360 |
| tcaaaccttt cttcaccaca tttcactgaa aggccacaca tctagagaga gaaacttcgt | 420 |
| ccaaatctct ctctccagca atggttgttg ctatggacca gcgcagcaat gttaacggag | 480 |
| attccggtgc ccggaaggaa gaagggtttg atccaagcga acaaccaccg tttaagatcg | 540 |
| gagatatcag ggcggcgatt cctaagcatt gttgggtgaa gagtcctttg agatctatga | 600 |
| gctacgtcgc cagagacatt ttcgccgtcg cggctctggc catggccgcc gtgtattttg | 660 |
| atagctggtt cctctggcca ctctactggg ttgcccaagg aaccctttc tgggccatct | 720 |
| tcgttcttgg ccacgactgg taaattaaat tttctgtttt aattatttg actcttttg | 780 |
| ttcaatttat taatttcttg aatgcacgtt cgatgagtat cgtcgtcact gacttcaaga | 840 |
| tttaattctt tgaggttac cttttcatgt tcaattatta aaaaaataaa ataaatata | 900 |
| ggatctaaga ttttttttctt catcagttca agcatcatca ctcatcagtc gtaagactcg | 960 |
| taacaaaata tcttcttttc tataattaat attatttccg catttaatgg atctacgttt | 1020 |
| tgatgttctc aaattttgtt tctctttctc tagatccccg gaacttttaa ttataattat | 1080 |
| agtatagtat aatatcaaga aaatatactg tttattttttt ttggcaacaa atatattact | 1140 |
| cttgtttctt tgacaagaaa aaaatatatt gtttttttttc ttcttttgt gttccaatct | 1200 |
| attttcgaga tttagacaag tgacacgtca tataccggat tgttaccctt gttaaagagt | 1260 |
| ttgggttaaa acaaatgtag aaaagttaaa ataaattgtg caataaatga taaatacgtt | 1320 |
| tttatgttaa acaatgatgt gaaaataaaa ttgaataatg gcagtggaca tgggagtttt | 1380 |
| tcagacattc ctctgctgaa cagtgtggtt ggtcacattc ttcattcatt catcctcgtt | 1440 |
| ccttaccatg gttggtaagt catttattaa ctatttccat gtaaactatt agtacttgtt | 1500 |
| ttcgtatttc ttacattttc gtttgtcatt cttcttgggt gcatgctagc aaactgtaat | 1560 |

```
cagtattaac tgggaactac caactgtttt tttttttgcta gagtagcaat tttataatta    1620
aataagaatc ctattaaaca atgcatgtga caatatgagg ttgcttttct gttcaaaaca    1680
aatctttaga agccaatgaa aaagaatcca aaactttttt ttaaatgata tgcgcctatc    1740
tattggtcct gactcctgag tttttcttact ttcttaagta taattagatt ttgatttttt   1800
tttataggtt ttcactattg ttatttgttt acatcagctt cagatatctt cgaaaaagat    1860
ttacatgcat caatttcatg aggatttata gttttttcttt tacttatttc cgacacaatg    1920
tttagtagta aaaagcatta aatgttttttt tgctcaaaaa aaaagaatg ggattgttag     1980 agcactctat tgttagttgt tcaataaata taccaactaa aaaaacaaaa taaatataaa     2040
atgagtgaga ttgttaaatc attatagaga caatttcatt ttcacaaaaa taaataaata    2100
cataactttt tataattggg gtttgcagga gaataagcca tcggacacac caccagaacc    2160
atggccatgt tgaaaacgac gagtcttggg ttccggtaat ctttcctact ctcgtagttt    2220
ctcttgtctt ttattttattt gtttgttttt cggaatttat tcttatgtct atgttcttag   2280
gattctatat gtttattttta ttagtttatg ttttcagtct gaggtcagac cgaccacttg    2340
tcagatctgt tttctagctg tagtaaaaaa caatttgcaa gtgtaatagt tcagcataat    2400
tgatcttgtt agagcatttc caaaacaaac tttataattt taaatataca gttttttgtt    2460
ctctaaaaaa gaatttaaaa attttaaagt ttgagggacg aaacttcaaa tttgaacttt    2520
cactactcaa cttcaaattt gaaatttcat cttttttatt tacattttga tcattataat    2580
taattataca ttcatttat gattcttaag tatttttctca tttattgttt taattccttaa   2640 attttttata catcataaat atttccaatt tgttttttata aattcaaatt ttacacaaaa   2700
aagtaataaa aattttaaat aagatttata atatttaaaa actataatta ggcaaaaaaa    2760
atattacaaa aaaatgtaat aaaaacttta aaataagata tatcaagaca taattattag    2820 aaatttttaaa tattataaca atattaataa tctggtaaat ttgctccaaa acctcaaaaa    2880
tttctaaatt attgtccaaa caaatttgtt taaccgaata tggagcatta caaaaataat    2940
tttatggaat agtgtggtat tttgcttgta gttaatatttt aattatgtat ttctatttat   3000
aattttatat atttaatgta agattttttt aattaatatt actgtaatat ttttatatat    3060
gtactagtta tttataaaag ttttatagat ttgtattagt tataacaaaa ataaggatca    3120
ttgtgtaaaa tacaaataat tttgaaatta cgtttaaagt tttggttatg aaaaaaatac    3180
tttgaaactt taaatttaga gttttgcaaa cttttaaaatg ttagatagat agtttttttg   3240
gagatgcatt tagtggttat ggtagtaact cagaaaatga aaaatctata cttttatact    3300
ccctccgttt tttaatataa gtcgttttac agttatacac gtagattaag aaaaccatta    3360
atttcttata ttttctagac aaaaacatca ttaattattt acctaaccac aattcaacca    3420
atataaaaat agaagatata ttaccattgg tcatacaaca ttaattatta ataaattta    3480 catagaaaac cgaaacgac atataatttg gaacaaaaaa atttctctaa aacgacttat    3540
attaaaaaac ggagggagta gtacctaact ttaacgatgg accacttata ttcgagtcct    3600
tagcataaaa tgattctcct cgaaatccgt ttactttctt cattattttt tccttttcag    3660
ttttggcgtt ttcgtaatac ttttgtcttc aatcttgaaa gctattagta taaaaactta    3720
taaacacatc acatgcaatg aattaatacg aatacataac cagaatgaca aattttcaat    3780
gaatatttaa taccagtaag tactactccg taatagtaat agtaatagtc atattaattt    3840 ttttttttgtc atcaaacaaa cagtaatagt aatattaatt ataattatgt atttcagttg    3900
```

```
ccagaaaagt tgtacaagaa cttgccccat agtactcgga tgctcagata cactgttcct    3960
ctgcccatgc tcgcttaccc gatctatctg gtaaaaaaaa atacaatttc aatttttttc    4020
ttaaaattac aaatggtttt atattttgag ttttaagcca atatataaat taattttgat    4080
tggattttaa ctacagtggt acagaagtcc tggaaaagaa gggtcacatt ttaacccata    4140
cagtagttta tttgctccaa gcgagaggaa gcttattgca acttcaacaa cttgctggtc    4200
cataatgttg gccactcttg tttatctatc gttcctcgtt ggtccagtca cagttctcaa    4260
agtctatggt gttccttaca ttgtaagttt cacatattat tacaagagat ttatatatta    4320
ttaataataa atttgttttt tgacataaag ttttggaaaa ttttcagatc tttgtaatgt    4380
ggttggacgc tgtcacgtac ttgcatcatc atggtcacga tgagaagttg ccttggtaca    4440
gaggcaaggt aaataaatca attttaaaa agaaatgtac agaaagcaat aatggttagt    4500
attgattaat cttaattttt gatgttttgc atacaataat aggaatggag ttatttacgt    4560
ggaggattaa caactattga tagagattac ggaatcttca acaacatcca tcacgacatt    4620
ggaactcacg tgatccatca tcttttccca caaatccctc actatcactt ggtcgatgcg    4680
gtgagtgatc tagcttttctc tctctctagt ttcatttgat taaatggtga ttaattacta    4740
atttaattaa tgaattgtgg acagacgaga gcagctaaac atgtgttagg aagatactac    4800
agagagccga agacgtcagg agcaataccg attcacttgg tggagagttt ggtcgcaagt    4860
attaaaaaag atcattacgt cagtgacact ggtgatattg tcttctacga gacagatcca    4920
gatctctacg tttat                                                     4935
```

```
<210> SEQ ID NO 34
<211> LENGTH: 383
<212> TYPE: PRT
<213> ORGANISM: Brassica napus

<400> SEQUENCE: 34

Met Val Val Ala Met Asp Gln Arg Ser Asn Val Asn Gly Asp Ser Gly
  1               5                  10                  15

Ala Arg Lys Glu Glu Gly Phe Asp Pro Ser Glu Gln Pro Pro Phe Lys
             20                  25                  30

Ile Gly Asp Ile Arg Ala Ala Ile Pro Lys His Cys Trp Val Lys Ser
         35                  40                  45

Pro Leu Arg Ser Met Ser Tyr Val Ala Arg Asp Ile Phe Ala Val Ala
     50                  55                  60

Ala Leu Ala Met Ala Ala Val Tyr Phe Asp Ser Trp Phe Leu Trp Pro
 65                  70                  75                  80

Leu Tyr Trp Val Ala Gln Gly Thr Leu Phe Trp Ala Ile Phe Val Leu
                 85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190
```

```
Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
        210                 215                 220

Val Tyr Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
                260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
        290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
                355                 360                 365

Asp Pro Asp Leu Tyr Val Tyr Ala Ser Asp Lys Ser Lys Ile Asn
        370                 375                 380
```

BRASSICA PLANTS YIELDING OILS WITH A LOW ALPHA LINOLENIC ACID CONTENT

CROSS REFERENCE TO RELATED APPLICATIONS

This application is a continuation of International Patent Application No. PCT/US2011/037864, filed May 25, 2011, which claims priority under 35 U.S.C. §119(e) to U.S. Provisional Application Ser. No. 61/348,121, filed May 25, 2010.

TECHNICAL FIELD

This invention relates to *Brassica* plants, and more particularly, *Brassica* plants having a modified allele at a fatty acid desaturase 3D locus and/or a fatty acid desaturase 3E locus and yielding an oil with a low alpha linolenic acid content in combination with a typical, mid, or high oleic acid content.

BACKGROUND

Canola oil contains a relatively high (8%-10%) alpha-linolenic acid (ALA) content. This trienoic fatty acid is unstable and easily oxidized during cooking, which in turn creates off-flavors of the oil. It also develops off odors and rancid flavors during storage (Hawrysh, 1990, Stability of canola oil, Chapter 7, pp. 99-122 In: F. Shahidi, ed. Canola and Rapeseed: Production, Chemistry, Nutrition, and Processing Technology, Van Nostrand Reinhold, N.Y.). Reducing the ALA content level by hydrogenation increases oxidative stability of the oil. However, hydrogenation results in the production of trans fatty acids, which increases the risk for coronary heart disease when consumed. Although an oil's oxidative stability is not determined solely by fatty acid profile, a decrease in the ALA content of canola oils generally improves the stability of the oils.

SUMMARY

This document is based on the discovery of a modified fad3D allele and a modified fad3E allele, and use of such alleles in *Brassica* plants to control ALA content. As described herein, *Brassica* plants containing such a modified fad3D allele and modified fad3E allele can produce oils with a low ALA content (i.e. 1.5% or less ALA). Such *Brassica* plants also can include other modified fatty acid desaturase alleles (e.g., fad2 or fad3), fatty acyl-acyl carrier protein thioesterase A2 (fatA2), and/or fatty acyl-acyl carrier protein thioesterase B (fatB) alleles to tailor the oleic acid and total saturated fatty acid content to the desired end use of the oil. *Brassica* plants described herein are particularly useful for producing canola oils for certain food applications as the plants are not genetically modified.

In one aspect, this document features a *Brassica* plant (e.g., *Brassica napus, Brassica juncea*, or *Brassica rapa* plant), progeny, and seeds of the plant that include a modified allele at a fatty acid desaturase 3D (fad3D) locus and/or a fatty acid desaturase 3E (fad3E) locus, wherein the modified allele results in the production of a FAD3D and/or FAD3E polypeptide having reduced desaturase activity relative to a corresponding wild-type polypeptide. The fad3E modified allele can include a nucleic acid encoding a truncated FAD3E polypeptide, a nucleic acid encoding a FAD3E polypeptide having a non-conservative substitution of a residue affecting substrate specificity, or a nucleic acid encoding a FAD3E polypeptide having a non-conservative substitution of a residue affecting catalytic activity. In some embodiments, the fad3E modified allele includes a mutation in a splice donor site. A modified fad3E allele can include a nucleotide sequence having at least 95% sequence identity to the nucleotide sequence set forth in SEQ ID NO:1. The fad3D modified allele can include a nucleic acid encoding a truncated FAD3D polypeptide, a nucleic acid having a deletion of an exon or a portion thereof (e.g., a deletion within exon 1 of the nucleic acid). In some embodiments, the fad3D modified allele includes a nucleotide sequence having at least 95% sequence identity to the nucleic acid sequence set forth in SEQ ID NO:32. A plant can include fad3E and fad3D modified alleles. The fad3E and fad3D modified alleles can be mutant alleles. A plant can be an $F_1$ hybrid.

Any of the plants described herein further can include a modified allele at a fad3A locus and/or a modified allele at a fad3B locus. The fad3A and/or fad3B modified alleles can be mutant alleles. For example, a fad3A modified allele can be selected from the group consisting of a) a nucleic acid encoding a FAD3A polypeptide having a cysteine substituted for arginine at position 275 and b) a nucleic acid encoding a truncated FAD3A polypeptide. A fad3B modified allele can be selected from the group consisting of a) a nucleic acid having a mutation in an exon-intron splice site recognition sequence and b) a nucleic acid encoding a truncated FAD3B polypeptide. Such plants can produce seeds yielding an oil having an ALA content of 0.6 to 1.5%.

Plants described herein can produce seeds yielding an oil having a stearic acid content of 2.5 to 6%.

Any of the plants described herein further can include a modified allele at a delta-12 fatty acid desaturase (fad2) locus. The fad2 modified allele can include a nucleic acid encoding a FAD2 polypeptide having a lysine substituted for glutamic acid in a His-Glu-Cys-Gly-His motif (SEQ ID NO:26). The fad2 modified allele comprising a nucleic acid encoding a FAD2 polypeptide having a glutamic acid substituted for glycine in the DRDYGILNKV motif (SEQ ID NO:28) or a histidine substituted for leucine in a KYLNNP motif (SEQ ID NO:27).

Any of the plants described herein further can include a modified allele at two different fad2 loci. One fad2 modified allele can include a nucleic acid encoding a FAD2 polypeptide having a lysine substituted for glutamic acid in a His-Glu-Cys-Gly-His motif (SEQ ID NO:26). One fad2 modified allele can include a nucleic acid encoding a FAD2 polypeptide having a glutamic acid substituted for glycine in the DRDYGILNKV motif (SEQ ID NO:28) or a histidine substituted for leucine in a KYLNNP motif (SEQ ID NO:27).

Any of the plants described herein further can include a modified allele at a fatty acyl-acyl-ACP thioesterase A2 (fatA2) locus and/or a fatty acyl-acyl-ACP thioesterase B (fatB) locus. The fatA2 and/or fatB modified alleles can be mutant alleles. A fatA2 modified allele results in the production of a FATA2 polypeptide having reduced thioesterase activity relative to a corresponding wild-type FATA2 polypeptide. The fatA2 modified allele can include a nucleic acid encoding a FATA2 polypeptide having a mutation in a region (SEQ ID NO:11) corresponding to amino acids 242 to 277 of the FATA2 polypeptide. The FATA2 polypeptide can include a substitution of a leucine residue for proline at position 255. A fatB modified allele results in the production of a FATB polypeptide having reduced thioesterase activity relative to a corresponding wild-type FATB polypeptide. A plant can include modified alleles at four different fatB loci. At least one of the fatB modified alleles can include a nucleic acid encoding a truncated FATB polypeptide. For example, a truncated FATB polypeptide can include a nucleotide sequence selected from the group consisting of: SEQ ID NO:22 SEQ ID NO:23, SEQ ID NO:24, and SEQ ID NO:25.

In another aspect, this document features a method of producing an oil. The method includes crushing seeds produced from at least one *Brassica* plant described herein; and extracting oil from the crushed seeds, wherein the oil has, after refining, bleaching, and deodorizing, an ALA content of 0.6 to 1.5%. The oil further can have a stearic acid content of 2.5 to 6.0%.

This document also features a method for making a *Brassica* progeny plant. The method includes crossing one or more first *Brassica* parent plants comprising a modified allele at a fad3E locus and/or a fad3D locus and one or more second *Brassica* parent plants comprising a modified allele at a different fad3 locus, wherein each modified allele results in the production of a FAD3 polypeptide having reduced desaturase activity relative to a corresponding wild-type FAD3 polypeptide; and selecting, for one to five generations, for progeny plants having a modified allele at the fad3E locus and/or fad3D locus, and the modified allele at the different fad3 locus, thereby obtaining the *Brassica* plant.

In another aspect, this document features a method for making a *Brassica* plant. The method includes obtaining one or more first *Brassica* parent plants comprising a modified allele at a fad3E locus and/or modified allele at a fad3D locus, wherein the fad3E or fad3D modified allele results in the production of a FAD3E or FAD3D polypeptide having reduced desaturase activity relative to a corresponding wild-type FAD3 polypeptide; obtaining one or more second *Brassica* parent plants comprising a modified allele at a fad2 locus, the fad2 modified allele comprising a nucleic acid encoding a FAD2 polypeptide having a lysine substituted for glycine in a His-Glu-Cys-Gly-His motif (SEQ ID NO:26); crossing the one or more first *Brassica* parent plants and the one or more second *Brassica* parent plants; and selecting, for one to five generations, for progeny plants having the modified allele at the fad3E locus and/or fad3D locus, and the modified allele at the fad2 locus thereby obtaining the *Brassica* plant. The first *Brassica* parent plant can include a modified allele at three different fad3 loci (e.g., fad3D, fad3A and fad3B).

In another aspect, this document features a method for making a *Brassica* plant. The method includes obtaining one or more first *Brassica* parent plants comprising a modified allele at a fad3E locus and/or fad3D locus, wherein the fad3E or said fad3D modified allele results in the production of a FAD3E or FAD3D polypeptide having reduced desaturase activity relative to a corresponding wild-type FAD3 polypeptide; obtaining one or more second *Brassica* parent plants comprising a modified allele at a fatA2 locus, the fatA2 modified allele comprising a nucleic acid encoding a FATA2 polypeptide having a mutation in a region (SEQ ID NO:11) corresponding to amino acids 242 to 277 of the FADA2 polypeptide; crossing the one or more first *Brassica* parent plants and the one or more second *Brassica* parent plants; and selecting, for one to five generations, for progeny plants having the modified allele at the fad3E locus and/or the fad3D locus, and the modified allele at the fatA2 locus thereby obtaining the *Brassica* plant. The first *Brassica* parent plant further can include a modified allele at a fad2 locus, a modified allele at a fad3A locus, and a modified allele at a fad3B locus, wherein the fad2 modified allele comprising a nucleic acid encoding a FAD2 polypeptide having a lysine substituted for glutamic acid in a His-Glu-Cys-Gly-His motif (SEQ ID N:26), the fad3A modified allele comprising a nucleic acid encoding a FAD3A polypeptide having a cysteine substituted for arginine at position 275, and the fad3B modified allele comprising a fad3B nucleic acid sequence having a mutation in an exon-intron splice site recognition sequence.

This document also features a method for making a *Brassica* plant. The method includes obtaining one or more first *Brassica* parent plants comprising a modified allele at a fad3E locus or a fad3D locus, wherein the fad3E or fad3D modified allele results in the production of a FAD3E or FAD3D polypeptide having reduced desaturase activity relative to a corresponding wild-type FAD3 polypeptide; obtaining one or more second *Brassica* parent plants comprising at least one modified allele at a fatB locus, wherein the fatB modified allele results in the production of a FATB polypeptide having reduced thioesterase activity relative to a corresponding wild-type FATB polypeptide; crossing the one or more first *Brassica* parent plants and the one or more second *Brassica* parent plants; and selecting, for one to five generations, for progeny plants having the modified allele at the fad3E locus and/or fad3D locus, and the at least one modified fatB allele at the fatB locus, thereby obtaining the *Brassica* plant. The one or more second *Brassica* plants can include modified alleles at four different fatB loci. At least one of the fatB modified alleles can include a nucleic acid encoding a truncated FATB polypeptide.

In another aspect, this document features seeds of a *Brassica* plant comprising a modified allele at a fad3E locus and/or a modified allele at a fad3D locus. The fad3E modified allele can include a nucleic acid having a mutation in a splice donor site. The fad3D modified allele can include a nucleic acid having a deletion of a portion of exon 1. The seeds can yield an oil having an ALA content of 0.6% to 1.5%. The seeds can be $F_2$ seeds. The *Brassica* plant further can include modified alleles at fad3A and/or fad3B loci. The *Brassica* plant further can include a modified allele at a fad2 locus. The *Brassica* plant further can include a modified allele at a fatB locus. The *Brassica* plant further can include a modified allele at a fatA2 locus. The *Brassica* plant further can include modified alleles at fad3A, fad3B, fad2, fatB, and fatA2 loci.

In yet another aspect, this document features a plant cell of a plant described herein, wherein the plant cell includes one or more of the modified alleles.

This document also features an isolated nucleic acid that includes a nucleic acid sequence selected from the group consisting of i) the nucleic acid sequence set forth in SEQ ID NO:1; ii) the nucleic acid sequence set forth in SEQ ID NO:32; iii) the complement of the nucleic acid sequence set forth in i) or ii); and iv) a nucleic acid fragment of i), ii), or iii) that is at least 50 nucleotides in length and distinguishes a mutant fad3D or fad3E allele from a wild-type fad3D or fad3E allele.

In another aspect, this document features a method of making a plant line. The method includes providing a population of plants; identifying one or more plants in the population containing a modified allele at a fad3E locus and/or a fad3D locus, wherein the modified allele results in the production of a FAD3E or FAD3D polypeptide having reduced desaturase activity relative to a corresponding wild-type FAD3 polypeptide; crossing one or more of the identified plants with itself or a different plant to produce seed; crossing at least one progeny plant grown from the seed with itself or a different plant; and repeating the crossing steps for an additional 0-5 generations to make the plant line, wherein the modified allele at the fad3E locus and/or the fad3D locus is present in the plant line.

This document also features *Brassica napus* seed designated 1904 and represented by American Type Culture Collection (ATCC) Accession No. PTA-11273, as well as progeny of the seed designated 1904 and represented by ATCC Accession No. PTA-11273.

This document also features *Brassica napus* seed designated 2558 and represented by American Type Culture Collection (ATCC) Accession No. PTA-11274, as well as progeny of the seed designated 2558 and represented by ATCC Accession No. PTA-11274.

Unless otherwise defined, all technical and scientific terms used herein have the same meaning as commonly understood by one of ordinary skill in the art to which this invention belongs. All numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4 is an alignment of the BnFad3D sequences from 1904 (SEQ ID NO:32) and IMC201 and 95CB504 (SEQ ID NO:33) showing a DNA deletion in the 1904 BnFad3D starting at position 575 in this alignment, which includes a portion of exon 1 and intron 1. The start codon (ATG) is at position 441.

FIG. 5 is the amino acid sequence of the FAD3D polypeptide (SEQ ID NO:34). In line 1904, the FAD3D polypeptide is truncated after amino acid 64.

Like reference symbols in the various drawings indicate like elements.

DETAILED DESCRIPTION

Figure 1:
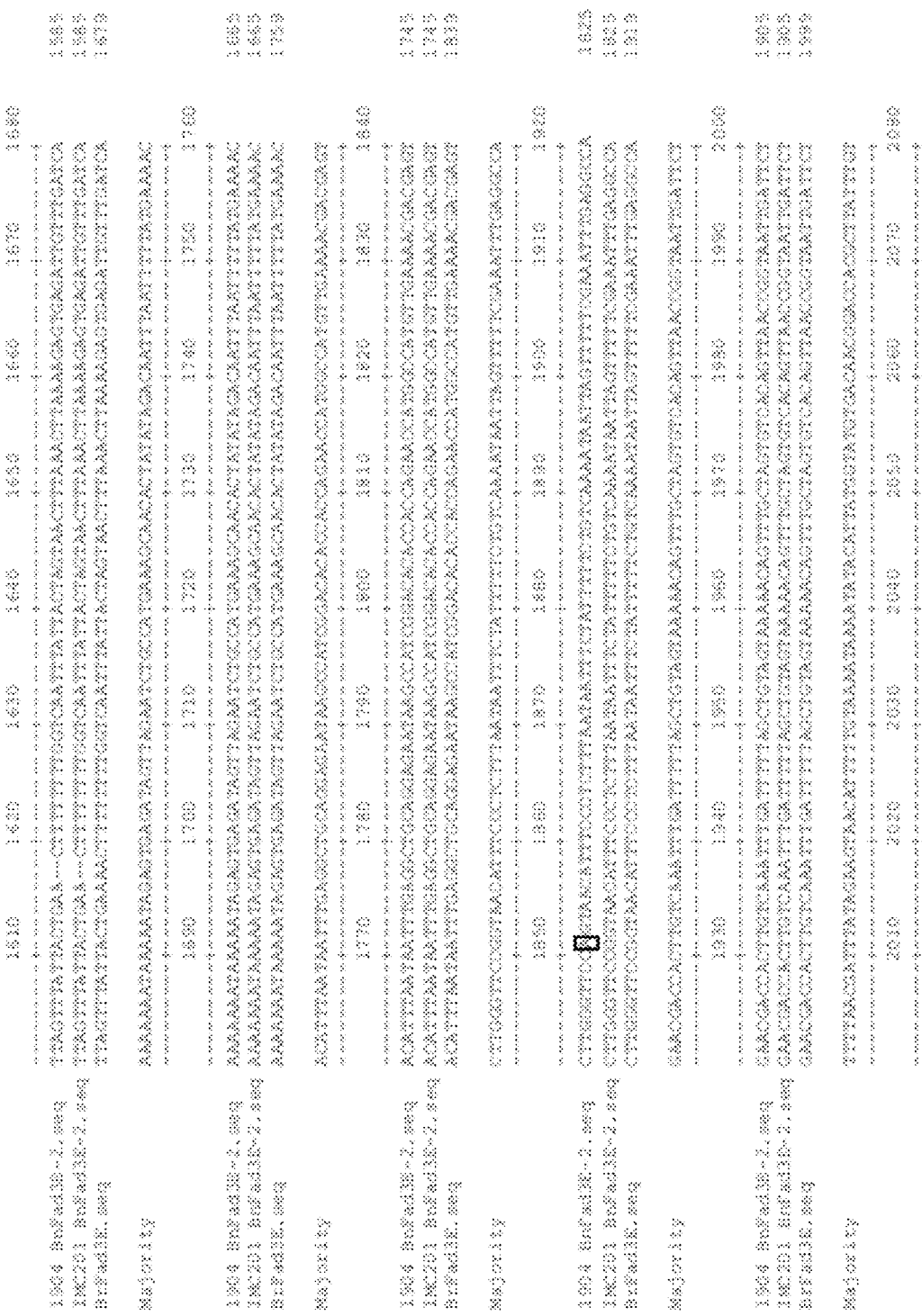
FIG. 1 is an alignment of the BnFad3E sequences from 1904, IMC201, and BrFad3E (SEQ ID NOs:1, 2, and 3, respectively). The BnFad3E-2 SNP that correlates with the low ALA (C18:3) content in the 1904 mutant line is highlighted with a black box at position 1851 of this alignment. At the position 1756 in SEQ ID NO:1 (1904 BnFad3E-2.seq), a single nucleotide mutation (G to A) is shown, which is located in a splice donor site (see FIG. 2). The start codon (ATG) is underlined at position 94 of this sequence alignment and the stop codon in BrFad3E (TAA) is at position 3828.
Figure 1:

In general, this document provides *Brassica* plants, including *B. napus, B. juncea*, and *B. rapa* species of *Brassica*, that yield seeds producing oils having a low ALA content (i.e., 1.6% or less). Canola oil produced from seeds having a low ALA content tends to exhibit increased stability (e.g., oxidative stability and/or flavor stability) and a useful nutritional profile, and can be used for many food applications including as a frying oil.

In some embodiments, plants described herein yield seeds producing oils having a low ALA content in combination with low total saturated fatty acids (i.e., 6% or less) or very low total saturated fatty acids (i.e., having 3.6% or less). As used herein, total saturated fatty acid content refers to the total of myristic acid (C14:0), palmitic acid (C16:0), stearic acid (C18:0), arachidic acid (C20:0), behenic acid (C22:0), and lignoceric acid (C24:0). For example, *Brassica* plants described herein can produce oils having a low ALA content and a total saturated fatty acid content of 2.5 to 6.0%, 3 to 5%, 3 to 4.5%, 3.25 to 3.75%, 3.0 to 3.5%, 3.4 to 3.7%, 3.6 to 5%, 4 to 5.5%, 4 to 5%, or 4.25 to 5.25%. Oils having a low ALA content and a low or very low total saturated fatty acid content have improved oxidative stability and nutritional quality and can help consumers reduce their intake of saturated fatty acids.

In some embodiments, *Brassica* plants yield seed oils having a low ALA content in combination with a typical (60%-70%), mid (70.1%-80%), or high (>80%) oleic acid content. In some embodiments, the total saturated fatty acid content of such seed oils can be less than 6%. As such, *Brassica* plants can produce seed oils having a fatty acid content tailored to the desired end use of the oil (e.g., frying or food applications). For example, *Brassica* plants can be produced that yield seeds having a low ALA content (e.g., 1.5% or less), an oleic acid content of 60 to 70%, and a linoleic acid content of 17 to 24%. Canola oils having such a fatty acid profile are particularly useful for frying applications due to the polyunsaturated fatty acid content, which is low enough to have improved oxidative stability for frying yet high enough to impart the desired fried flavor to the food being fried, and are an improvement over commodity type canola oils. The fatty acid content of commodity type canola oils may be on the order of is 6 to 8% total saturated fatty acids, 55 to 65% oleic acid, 20 to 30% linoleic acid, and 7 to 10% α-linolenic acid. See, e.g., *Bailey's Industrial Oil and Fat Products*, Section 2.2, "Canola Oil" on pages 61-121 of Volume 2 (6th Edition, 2005).

In some embodiments, *Brassica* plants can be produced that yield seeds having a low ALA content, mid-oleic acid content (e.g., 70.1 to 80% oleic acid) and a low total saturated fatty acid content (e.g., <6.0%). Canola oils having such a fatty acid profile have an oxidative stability that is higher than oils with higher ALA and lower oleic acid contents or commodity type canola oils, and are useful for coating applications (e.g., spray-coatings), formulating food products, or other applications where shelf-life stability is desired. In addition, *Brassica* plants can be produced that yield seeds having a low ALA content, high oleic acid content (e.g., 80.1 to 90% oleic acid) and a low total saturated fatty acid content (<6.0%). Canola oils having a low ALA, high oleic acid, and low total saturated fatty acid content are particularly useful for food applications requiring high oxidative stability and a reduced saturated fatty acid content.

Brassica Plants

Brassica plants described herein can have reduced levels of ALA (e.g., 8.0% or less) in the seed oil as a result of reduced activity of fatty acid desaturase (FAD) 3E (also known as delta-15 desaturase). Brassica plants described herein also can have reduced levels of ALA (e.g., 3.0% or less, 2.8% or less, 2.6% or less) in the seed oil as a result of reduced activity of FAD3D. FAD3 proteins are involved in the enzymatic conversion of linoleic acid to α-linolenic acid. Sequences of higher plant Fad3 genes are disclosed in Yadav et al., Plant Physiol., 103:467-476 (1993), WO 93/11245, and Arondel et al., Science, 258:1353-1355 (1992). It is understood that throughout the disclosure, reference to "plant" or "plants" includes progeny, i.e., descendants of a particular plant or plant line, as well as cells or tissues from the plant. Progeny of an instant plant include seeds formed on $F_1$, $F_2$, $F_3$, $F_4$ and subsequent generation plants, or seeds formed on $BC_1$, $BC_2$, $BC_3$, and subsequent generation plants. Seeds produced by a plant can be grown and then selfed (or outcrossed and selfed, or doubled through dihaploid) to obtain seeds homozygous for a modified allele. The term "allele" or "alleles" refers to one or more alternative forms of a gene at a particular locus. As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production, and includes hybrid varieties and open-pollinated varieties.

Reduced activity, including absence of detectable desaturase activity, of FAD3E and/or FAD3D can be achieved by modifying an endogenous fad3E or fad3D allele. An endogenous fad3E or fad3D allele can be modified by, for example, mutagenesis or by using homologous recombination to replace an endogenous plant gene with a variant containing one or more mutations (e.g., produced using site-directed mutagenesis). See, e.g., Townsend et al., Nature 459:442-445 (2009); Tovkach et al., Plant J., 57:747-757 (2009); and Lloyd et al., Proc. Natl. Acad. Sci. USA, 102:2232-2237 (2005). Similarly, for other genes discussed herein, the endogenous allele can be modified by mutagenesis or by using homologous recombination to replace an endogenous gene with a variant. Modified alleles obtained through mutagenesis are encompassed by the term "mutant alleles" as that term is used herein.

Reduced desaturase activity, including absence of detectable activity, can be inferred from the decreased level of linolenic acid (product) and in some cases, increased level of linoleic acid (the substrate) in the plant compared with a corresponding control plant. Reduced activity also can be assessed by in vitro translation of the desaturase and assaying for desaturase activity. See, for example, Goren and Fox, Protein Expr Purif. 62(2): 171-178 (2008).

Genetic mutations can be introduced within a population of seeds or regenerable plant tissue using one or more mutagenic agents. Suitable mutagenic agents include, for example, ethyl methane sulfonate (EMS), methyl N-nitrosoguanidine (MNNG), ethidium bromide, diepoxybutane, ionizing radiation, x-rays, UV rays and other mutagens known in the art. In some embodiments, a combination of mutagens, such as EMS and MNNG, can be used to induce mutagenesis. The treated population, or a subsequent generation of that population, can be screened for reduced desaturase activity that results from the mutation, e.g., by determining the fatty acid profile of the population and comparing it to that of a corresponding non-mutagenized population. Mutations can be in any portion of a gene, including coding sequence, exon sequence, intron sequence, and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product. In some embodiments, the mutation is a deletion of an exon or a portion thereof, resulting in the production of a truncated polypeptide from either lack of or incorrect RNA splicing. In some embodiments, the mutation is a nonsense mutation, which results in the introduction of a stop codon (TGA, TAA, or TAG) and production of a truncated polypeptide. The gene product of an allele having a stop codon mutation typically lacks detectable desaturase activity. In some embodiments, the mutation is a splice site mutation which alters or abolishes the correct splicing of the pre-mRNA sequence, resulting in a protein of different amino acid sequence than the wild type. For example, one or more exons may be skipped during RNA splicing, resulting in a protein lacking the amino acids encoded by the skipped exons. Alternatively, the reading frame may be altered by incorrect splicing, one or more introns may be retained, alternate splice donors or acceptors may be generated, or splicing may be initiated at an alternate position, or alternative polyadenylation signals may be generated. In some embodiments, more than one mutation or more than one type of mutation is introduced. PCR can be used to amplify modified alleles in genomic DNA from the plant or plant tissue, and the resulting amplification product can be isolated and sequenced to characterize the polypeptide encoded by the modified allele. In some embodiments, RT-PCR can be used to detect particular RNA transcripts.

Insertions, deletions, or substitutions of amino acids in a protein sequence may, for example, disrupt the conformation of essential alpha-helical or beta-pleated sheet regions of the resulting gene product. Amino acid insertions, deletions, or substitutions also can disrupt binding, alter substrate specificity, or disrupt catalytic sites important for gene product activity. It is known in the art that the insertion or deletion of a larger number of contiguous amino acids is more likely to render the gene product non-functional, compared to a smaller number of inserted or deleted amino acids. Non-conservative amino acid substitutions may replace an amino acid of one class with an amino acid of a different class. Non-conservative substitutions may make a substantial change in the charge or hydrophobicity of the gene product. Non-conservative amino acid substitutions may also make a substantial change in the bulk of the residue side chain, e.g., substituting an alanine residue for an isoleucine residue.

Examples of non-conservative substitutions include the substitution of a basic amino acid for a non-polar amino acid, or a polar amino acid for an acidic amino acid. Because there are only 20 amino acids encoded in a gene, substitutions that result in reduced activity may be determined by routine experimentation, incorporating amino acids of a different class in the region of the gene product targeted for mutation.

In some embodiments, a plant described herein contains a modified allele at a fad3E locus. For example, a fad3E locus can include a nucleotide sequence having at least 90% (e.g., at least 91, 92, 93, 94, 95, 96, 97, 98, or 99%) sequence identity to the nucleotide sequence set forth in SEQ ID NO:1. The nucleotide sequence set forth in SEQ ID NO:1 is a representative nucleotide sequence of the fad3E gene from B. napus line 1904, which contains a single nucleotide mutation (G to A) in a splice donor site. As used herein, the term "sequence identity" refers to the degree of similarity between any given nucleic acid sequence and a target nucleic acid sequence. The degree of similarity is represented as percent sequence identity. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. Percent sequence identity can be determined using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (i) a 500-base nucleic acid target sequence is compared to a subject nucleic acid sequence, (ii) the Bl2seq program presents 200 bases from the target sequence aligned with a region of the subject sequence where the first and last bases of that 200-base region are matches, and (iii) the number of matches over those 200 aligned bases is 180, then the 500-base nucleic acid target sequence contains a length of 200 and a sequence identity over that length of 90% (i.e., 180, 200×100=90).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

In some embodiments, a plant described herein contains a modified allele at a fad3D locus. For example, a fad3D locus can include a nucleotide sequence having at least 90% (e.g., at least 91, 92, 93, 94, 95, 96, 97, 98, or 99%) sequence identity to the nucleotide sequence set forth in SEQ ID NO:32. The nucleotide sequence set forth in SEQ ID NO:32 is a representative nucleotide sequence of the fad3D gene from *B. napus* line 1904, which contains a deletion of 164 nucleotides from exon 1. In *B. napus* line IMC201 and 95CB504, exon 1 starts at position 441 and ends at position 739. See, e.g., FIG. 4.

In some embodiments, a *Brassica* plant contains a modified fad3E allele and a modified fad3D allele. A modified fad3E and a modified fad3D allele may be combined in a plant by making a genetic cross between modified lines. For example, a plant having a modified allele at a fad3E locus can be crossed or mated with a second plant having a modified allele at a fad3D locus. Seeds produced from the cross are planted and the resulting plants are selfed in order to obtain progeny seeds. These progeny seeds can be screened in order to identify those seeds carrying both modified alleles. In some embodiments, progeny are selected over multiple generations (e.g., 2 to 5 generations) to obtain plants having modified fad3E and fad3D alleles. In some embodiments, a line having both fad3E and fad3D modified alleles is used to introgress an individual modified allele into a different line or to introgress both modified alleles into a different line.

In some embodiments, a *Brassica* plant contains a modified fad3E allele or a modified fad3D allele, and optionally one or more modified alleles at fad3 (e.g. fad3A and/or fad3B), fatA2, fatB, and fad2 loci. In some embodiments, a *Brassica* plant contains a modified fad3E allele and a modified fad3D allele, and optionally one or more modified alleles at fad3 (e.g., fad3A and/or fad3B), fatA2, fatB, and fad2 loci. For example, a *Brassica* plant can contain a modified fad3E allele, a modified fad3D allele, and one or more other modified fad3 alleles. For example, in addition to a modified fad3E and fad3D allele, *Brassica* plants can contain the mutation from the APOLLO or STELLAR *B. napus* variety that confers low linolenic acid. The STELLAR and APOLLO varieties were developed at the University of Manitoba (Manitoba, Canada). In some embodiments, the disclosed plants contain the fad3A and/or fad3B mutation from IMC02 that confer a low linolenic acid phenotype. IMC02 contains a mutation in both the fad3A and fad3B genes. The fad3A gene contains a C to T mutation at position 2565, numbered from the ATG in genomic DNA, resulting in the substitution of a cysteine for arginine at position 275 of the encoded FAD3A polypeptide. The fad3B gene contains a G to A mutation at position 3053 from ATG in genomic DNA, located in the exon-intron splice site recognition sequence. IMC02 was obtained from a cross of IMC01 x Westar. See Example 3 of U.S. Pat. No. 5,750, 827. IMC01 was deposited with the American Type Culture Collection (ATCC) under Accession No. 40579. IMC02 was deposited with the ATCC under Accession No. PTA-6221. Other examples of fad3 mutations include nonsense mutations in fad3A and fad3B sequences. See, Example 4. For example, the mutant fad3A sequence set forth in SEQ ID NO:9 contains a mutation at position 102, resulting in a codon change from TGG to TGA and production of a truncated FAD3A polypeptide. The mutant fad3B sequence set forth in SEQ ID NO:10 contains a mutation at position 206, resulting in a codon change from TGG to TAG and production of a truncated FAD3B polypeptide.

Two or more different modified fad3 alleles may be combined in a plant by making a genetic cross between modified lines. For example, a plant having a modified allele at a fad3E locus and/or a fad3D locus can be crossed or mated with a second plant having a modified allele at a fad3A or fad3B locus. Seeds produced from the cross are planted and the resulting plants are selfed in order to obtain progeny seeds. These progeny seeds can be screened in order to identify those seeds carrying both modified alleles. In some embodiments, progeny are selected over multiple generations (e.g., 2 to 5 generations) to obtain plants having modified alleles at two different fad3 loci.

Brassica plants having a modified allele at a fad3E locus or fad3D locus also can include modified alleles controlling fatty acyl-ACP thioesterase A2 (fatA2) and/or fatty acyl-ACP thioesterase B (fatB) to tailor the total saturated fatty acid content to the end use of the oil. Fatty acyl-ACP thioesterases hydrolyze acyl-ACPs in the chloroplast to release the newly synthesized fatty acid from ACP, effectively removing it from further chain elongation in the plastid. The free fatty acid can then leave the plastid, become bound to CoenzymeA (CoA) and enter the Kennedy pathway in the endoplasmic reticulum (ER) for triacylglycerol (TAG) biosynthesis. Members of the FATA family prefer oleoyl (C18:1) ACP substrates with minor activity towards 18:0 and 16:0-ACPs, while members of the FATB family hydrolyze primarily saturated acyl-ACPs between 8 and 18 carbons in length. See Jones et al., *Plant Cell* 7:359-371 (1995); Ginalski and Rhchlewski, *Nucleic Acids Res* 31:3291-3292 (2003); and Voelker T in Genetic Engineering (Setlow, J K, ed) Vol 18, 111-133, Plenum Publishing Corp., New York (2003).

Reduced activity of FATA2 and/or FATB, including absence of detectable activity, can be inferred from the decreased level of saturated fatty acids in the seed oil compared with seed oil from a corresponding control plant. Reduced activity also can be assessed in plant extracts using assays for fatty acyl-ACP hydrolysis. See, for example, Bonaventure et al., *Plant Cell* 15:1020-1033 (2003); and Eccleston and Ohlrogge, *Plant Cell* 10:613-622 (1998).

In some embodiments, in addition to a modified allele at a fad3E locus and/or a fad3D locus, and optionally one or more other modified fad3 loci, a *Brassica* plant contains a modified allele at a fatA2 locus, wherein the modified allele results in the production of a FATA2 polypeptide having reduced thioesterase activity relative to a corresponding wild-type FATA2 polypeptide. For example, the modified fatA2 allele can include a nucleic acid that encodes a FATA2 polypeptide having a non-conservative substitution within a helix/4-stranded sheet (4HBT) domain (also referred to as a hot-dog domain) or non-conservative substitution of a residue affecting catalytic activity or substrate specificity. For example, a *Brassica* plant can contain a modified allele that includes a nucleic acid encoding a FATA2b polypeptide having a substitution in a region (SEQ ID NO:11) of the polypeptide corresponding to residues 242 to 277 of the FATA2 polypeptide (as numbered based on the alignment to the *Arabidopsis thaliana* FATA2 polypeptide set forth in GenBank Accession No. NP_193041.1, protein (SEQ ID NO:12); GenBank Accession No. NM_117374, mRNA). This region of FATA2 is highly conserved in *Arabidopsis* and *Brassica*. In addition, many residues in this region are conserved between FATA and FATB, including the aspartic acid at position 259, asparagine at position 263, histidine at position 265, valine at position 266, asparagine at position 268, and tyrosine at position 271 (as numbered based on the alignment to SEQ ID NO:12). The asparagine at position 263 and histidine at position 265 are part of the catalytic triad, and the arginine at position 256 is involved in determining substrate specificity. See also Mayer and Shanklin, *BMC Plant Biology* 7:1-11 (2007). SEQ ID NO:13 sets forth the predicted amino acid sequence of the *Brassica* FATA2b polypeptide encoded by exons 2-6, and corresponding to residues 121 to 343 of the *A. thaliana* sequence set forth in SEQ ID NO:12. For example, the FATA2 polypeptide can have a substitution of a leucine residue for proline at the position corresponding to position 255 of the *Arabidopsis* FATA2 polypeptide (i.e., position 14 of SEQ ID NO:11 or position 135 of SEQ ID NO: 13). The proline in the *B. napus* sequence corresponding to position 255 in *Arabidopsis* is conserved among *B. napus, B. rapa, B. juncea, Zea mays*, Sorghum bicolor, *Oryza sativa* Indica (rice), *Triticum aestivum*, Glycine max, *Jatropha* (tree species), *Carthamus tinctorius, Cuphea hookeriana, Iris tectorum, Perilla frutescens, Helianthus annuus, Garcinia mangostana, Picea sitchensis, Physcomitrella patens* subsp. Patens, *Elaeis guineensis, mitis vinifera, Elaeis oleifera, Camellia oleifera, Arachis hypogaea, Capsicum annuum, Cuphea hookeriana, Populus trichocarpa*, and *Diploknema butyracea*. The mutation at position 255 is associated with a low total saturated fatty acid phenotype, low stearic acid phenotype, low arachidic acid phenotype, and an increased eicosenoic acid phenotype. The stearic acid content phenotype is negatively correlated with the eicosenoic acid phenotype. See, U.S. Provisional Application Nos. 61/287,985 and 61/295,049.

In some embodiments, the modified allele at a fatA2 locus includes a nucleotide sequence having at least 90% (e.g., at least 91, 92, 93, 94, 95, 96, 97, 98, or 99%) sequence identity to the nucleotide sequence set forth in SEQ ID NO:14 or SEQ ID NO:15. The nucleotide sequences set forth in SEQ ID NOs:14 and 15 are representative nucleotide sequences from the mutant fatA2b gene from *B. napus* line 15.24. See, U.S. Provisional Application Nos. 61/287,985 and 61/295,049.

In some embodiments, a *Brassica* plant contains a modified allele at a fatB locus, wherein the modified allele results in the production of a FATB polypeptide having reduced thioesterase activity relative to a corresponding wild-type FATB polypeptide. In some embodiments, a *Brassica* plant contains modified alleles at two or more different fatB loci. In some embodiments, a *Brassica* plant contains modified alleles at three different fatB loci or contains modified alleles at four different fatB loci. *Brassica napus* contains 6 different FATB isoforms (i.e., different forms of the FATB polypeptide at different loci), which are called isoforms 1-6 herein. SEQ ID NOs:16-21 set forth the nucleotide sequences encoding FATB isoforms 1-6, respectively, of *Brassica* napus. The nucleotide sequences set forth in SEQ ID NOs:16-21 have 82% to 95% sequence identity as measured by the ClustalW algorithm (version 1.83, default parameters). See Chenna et al., *Nucleic Acids Res.*, 31(13):3497-500 (2003).

For example, in addition to a modified allele at a fad3E locus and a fad3D locus, a *Brassica* plant can have a mutation in a nucleotide sequence encoding FATB isoform 1, isoform 2, isoform 3, isoform 4, isoform 5, or isoform 6. In some embodiments, a plant can have a mutation in a nucleotide sequence encoding FAD3E and can have mutation in a nucleotide sequence encoding 2 or more FATB isoforms, e.g., FATB isoforms 1 and 2; 1 and 3; 1 and 4; 1 and 5; 1 and 6; 2 and 3; 2 and 4; 2 and 5; 2 and 6; 3 and 4; 3 and 5; 3 and 6; 4 and 5; 4 and 6; 5 and 6; 1, 2, and 3; 1, 2, and 4; 1, 2, and 5; 1, 2, and 6; 1, 3, and 4; 1, 3, and 5; 1, 3, and 6; 1, 4, and 5; 1, 4, and 6; 1, 5, and 6; 2, 3, and 4; 2, 3, and 5; 2, 3, and 6; 2, 4, and 5; 2, 4, and 6; 1, 5, and 6; 3, 4, and 5; 3, 4, and 6; 3, 5, and 6; 4, 5, and 6; 1, 2, 3, and 4; 1, 2, 3, and 5; 1, 2, 3, and 6; 1, 2, 4, and 5; 1, 2, 4, and 6; 1, 2, 5, and 6; 1, 3, 4 and 5; 1, 3, 4, and 6; 1, 3, 5, and 6; 1, 4, 5, and 6; 2, 3, 4, and 5; 2, 3, 4 and 6; 2, 3, 5, and 6; 2, 4, 5, and 6; or 3, 4, 5, and 6. In some embodiments, a *Brassica* plant can have a mutation in a nucleotide sequence encoding a FAD3E polypeptide and can have a mutation in nucleotide sequences encoding FATB isoforms 1, 2, and 3; 1, 2, and 4; 1, 3, and 4; 2, 3, and 4; or 1, 2, 3, and 4. In some embodiments, a mutation in a FATB isoform results in deletion of a 4HBT domain or a portion thereof of a FATB polypeptide. FATB polypeptides typically contain a tandem repeat of the 4HBT domain, where the N-terminal 4HBT domain contains residues affecting substrate specificity (e.g., two conserved methionines, a conserved lysine, a conserved valine, and a conserved serine) and the C-terminal 4HBT domain contains residues affecting catalytic activity (e.g., a catalytic triad of a conserved asparagine, a conserved histidine, and a conserved cysteine) and substrate specificity (e.g., a conserved tryptophan). See Mayer and Shanklin, *J. Biol. Chem.* 280:3621-3627 (2005). In some embodiments, the mutation in a nucleotide sequence encoding FATB results in a non-conservative substitution of a residue in a 4HBT domain or a residue affecting substrate specificity. In some embodiments, the mutation in a nucleotide sequence encoding FATB is a splice site mutation. In some embodiment, the mutation in a nucleotide sequence encoding FATB is a nonsense mutation in which a premature stop codon (TGA, TAA, or TAG) is introduced, resulting in the production of a truncated polypeptide.

SEQ ID NOs:22-25 set forth the nucleotide sequences encoding fatB isoforms 1-4, respectively, and containing exemplary nonsense mutations that result in truncated FATB polypeptides. SEQ ID NO:22 is the nucleotide sequence of isoform 1 having a mutation at position 154, which changes the codon from CAG to TAG. SEQ ID NO:23 is the nucleotide sequence of isoform 2 having a mutation at position 695, which changes the codon from CAG to TAG. SEQ ID NO:24 is the nucleotide sequence of isoform 3 having a mutation at position 276, which changes the codon from TGG to TGA. SEQ ID NO:25 is the nucleotide sequence of isoform 4 having a mutation at position 336, which changes the codon from TGG to TGA. See also U.S. Provisional Application Nos. 61/287,985 and 61/295,049.

Two or more different modified FATB alleles may be combined in a plant by making a genetic cross between modified lines. For example, a plant having a modified allele at a FATB locus encoding isoform 1 can be crossed or mated with a second plant having a modified allele at a FATB locus encoding isoform 2. Seeds produced from the cross are planted and the resulting plants are selfed in order to obtain progeny seeds. These progeny seeds can be screened in order to identify those seeds carrying both modified alleles. In some embodiments, progeny are selected over multiple generations (e.g., 2 to 5 generations) to obtain plants having modified alleles at two different FATB loci. Similarly, a plant having modified alleles at two or more different FATB isoforms can be crossed with a second plant having modified alleles at two or more different FATB alleles, and progeny seeds can be screened to identify those seeds carrying modified alleles at four or more different FATB loci. Again, progeny can be selected for multiple generations to obtain the desired plant.

In some embodiments, a modified allele at a fad3E locus, a fad3D locus, a fatA2 locus and modified alleles at two or more (e.g., three or four) different fatB loci can be combined in a plant. For example, a plant having a modified allele at a fad3E locus and a fad3D locus can be crossed or mated with a second plant having a modified allele at a fatA2 locus. Seeds produced from the cross are planted and the resulting plants are selfed in order to obtain progeny seeds. These progeny seeds can be screened in order to identify those seeds carrying modified fad3E, fad3D, and fatA2 alleles. Progeny can be selected over multiple generations (e.g., 2 to 5 generations) to obtain plants having a modified allele at a fad3E locus, a modified allele at a fad3D locus, and a modified allele at a fatA2 locus. Furthermore, progeny identified as having a modified allele at a fad3E locus, a modified allele at a fad3D locus, and a modified allele at a fatA2 locus can be crossed or mated with a second plant having modified alleles at two or more different fatB loci. Seeds produced from the cross are planted and the resulting plants are selfed in order to obtain progeny seeds. These progeny seeds can be screened in order to identify those seeds carrying modified fad3E, fad3D, fatA2, and fatB alleles. Progeny can be selected over multiple generations (e.g., 2 to 5 generations) to obtain plants having a modified allele at a fad3E locus, a modified allele at a fatA2 locus, and two or more different fatB loci. Plants having a modified allele at a fad3E locus, a fad3D locus, a fatA2b locus, and modified alleles at three or four different fatB loci have a low ALA content, high oleic acid content, and a low total saturated fatty acid content.

*Brassica* plants described herein also can have decreased activity of a delta-12 desaturase, which is involved in the enzymatic conversion of oleic acid to linoleic acid, to confer a mid or high oleic acid content in the seed oil. *Brassica* plants can exhibit reduced activity of delta-12 desaturase (also known as FAD2) in combination with reduced activity of FAD3E and optionally one or more of FAD3A, FAD3B, FATA2, and FATB. The sequences for the wild-type fad2 genes from *B. napus* (termed the D form and the F form) are disclosed in WO 98/56239. A reduction in delta-12 desaturase activity, including absence of detectable activity, can be achieved by mutagenesis. Decreased delta-12 desaturase activity can be inferred from the decrease level of linoleic acid (product) and increased level of oleic acid (substrate) in the plant compared with a corresponding control plant. Non-limiting examples of suitable fad2 mutations include the G to A mutation at nucleotide 316 within the fad2-D gene, which results in the substitution of a lysine residue for glutamic acid in a HECGH (SEQ ID NO:26) motif. Such a mutation is found within the line IMC129, which has been deposited with the ATCC under Accession No. 40811. Another suitable fad2 mutation can be the T to A mutation at nucleotide 515 of the fad2-F gene, which results in the substitution of a histidine residue for leucine in a KYLNNP (SEQ ID NO:27) motif (amino acid 172 of the Fad2 F polypeptide). Such a mutation is found within the variety Q508. See U.S. Pat. No. 6,342,658. Another example of a fad2 mutation is the G to A mutation at nucleotide 908 of the fad2-F gene, which results in the substitution of a glutamic acid for glycine in the DRDYGILNKV (SEQ ID NO:28) motif (amino acid 303 of the Fad2 F polypeptide). Such a mutation is found within the line Q4275, which has been deposited with the ATCC under Accession No. 97569. See U.S. Pat. No. 6,342,658. Another example of a suitable fad2 mutation can be the C to T mutation at nucleotide 1001 of the fad2-F gene (as numbered from the ATG), which results in the substitution of an isoleucine for threonine (amino acid 334 of the Fad2 F polypeptide). Such a mutation is found within the high oleic acid line Q7415.

Typically, the presence of one of the fad2-D or fad2-F mutations confers a mid-oleic acid phenotype (e.g., 70-80% oleic acid) to the seed oil, while the presence of both fad2-D and fad2-F mutations confers a higher oleic acid phenotype (e.g., >80% oleic acid). For example, Q4275 contains the fad2-D mutation from IMC129 and a fad2-F mutation at amino acid 303. Q508 contains fad2-D mutation from IMC129 and a fad2-F mutation at amino acid 172. Q7415 contains the fad2-D mutation from IMC129 and a fad2-F mutation at amino acid 334. The presence of both fad2 mutations in Q4275, Q508, and Q7415 confers a high oleic acid phenotype of greater than 80% oleic acid.

Thus, in some embodiments, a *Brassica* plant contains a modified allele at a fad3E locus and a modified allele at a fad2 locus. For example, a *Brassica* plant can contain a modified allele at a fad3E locus and a modified allele at a fad2 locus described above. A *Brassica* plant also can contain a modified allele at a fad3E locus, a modified allele at a fad2 locus, and a modified allele at a fatA2 locus. A *Brassica* plant can contain a modified allele at a fad3E locus, modified alleles at two or more different fatB loci (three or four different loci), and a fad2 locus described above. A *Brassica* plant also can contain a modified allele at a fad3E locus, fatA2 locus, modified alleles at two or more different fatB loci (three or four different loci) and a modified allele at a fad2 locus described above. In some embodiments, a *Brassica* plant contains a modified allele at a fad3E locus, at least one modified allele at a different fad3 locus, a modified allele at a fatA2 locus, a modified allele at one or more different fatB loci (e.g., two or more), and a modified allele at one or more fad2 loci. A *Brassica* plant also can contain modified alleles at a fad3E locus and a fad3D locus, modified alleles at two or more different fatB loci (three or four different loci), modified alleles at fad2 loci, and modified alleles at fad3A and/or fad3B loci described above. A *Brassica* plant also contain a modified allele at a fad3E locus, a modified allele at a fad3D locus, a modified allele at a fatA2 locus, modified alleles at two or more different FATB loci (three or four different loci), modified alleles at fad2 loci, and modified alleles at fad3A and fad3B loci described above.

One commercially important *Brassica* crop is *B. napus*. Commercial *B. napus* lines may be classified as either spring lines or winter lines. Winter lines are commonly planted in the autumn and flower in the spring after a period of vernalization over the winter. Spring lines do not require vernalization to flower and are commonly planted and harvested in the same growing season. Winter lines are common in Europe, but most winter lines fare poorly in the colder winters of Canada and the northern United States. As a consequence, most *B. napus* grown commercially in North America are spring lines. One useful embodiment provides a *Brassica* plant that is a *B. napus* plant. Though the *B. napus* plant may have a winter flowering habit, one preferred implementation has a spring growing habit, i.e., it does not require vernalization to flower.

Production of Hybrid *Brassica* Varieties

Hybrid *Brassica* varieties can be produced by preventing self-pollination of female parent plants (i.e., seed parents), permitting pollen from male parent plants to fertilize such female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be cytoplasmic male sterility (CMS), nuclear male sterility, molecular male sterility wherein a transgene inhibits microsporogenesis and/or pollen formation, or be produced by self-incompatibility. Female parent plants containing CMS are particularly useful. CMS can be, for example of the ogu (Ogura), nap, pol, tour, or mur type. See, for example, Pellan-Delourme and Renard, 1987, *Proc. 7$^{th}$ Int. Rapeseed Conf.*, Poznan, Poland, p. 199-203 and Pellan-Delourme and Renard, 1988, *Genome* 30:234-238, for a description of Ogura type CMS. See, Riungu and McVetty, 2003, *Can. J. Plant Sci.*, 83:261-269 for a description of nap, pol, tour, and mur type CMS.

In embodiments in which the female parent plants are CMS, the male parent plants typically contain a fertility restorer gene to ensure that the $F_1$ hybrids are fertile. For example, when the female parent contains an Ogura type CMS, a male parent is used that contains a fertility restorer gene that can overcome the Ogura type CMS. Non-limiting examples of such fertility restorer genes include the Kosena type fertility restorer gene (U.S. Pat. No. 5,644,066) and Ogura fertility restorer genes (U.S. Pat. Nos. 6,229,072 and 6,392,127). In other embodiments in which the female parents are CMS, male parents can be used that do not contain a fertility restorer. $F_1$ hybrids produced from such parents are male sterile. Male sterile hybrid seed can be inter-planted with male fertile seed to provide pollen for seed-set on the resulting male sterile plants.

The methods described herein can be used to form single-cross *Brassica* $F_1$ hybrids. In such embodiments, the parent plants can be grown as substantially homogeneous adjoining populations to facilitate natural cross-pollination from the male parent plants to the female parent plants. The $F_1$ seed formed on the female parent plants is selectively harvested by conventional means. One also can grow the two parent plants in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent that satisfies the fatty acid parameters for the female parent of the first cross. Here, assuming a bulk planting, the overall oleic acid content of the vegetable oil may be reduced over that of a single-cross hybrid; however, the seed yield will be further enhanced in view of the good agronomic performance of both parents when making the second cross. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Hybrids described herein have good agronomic properties and exhibit hybrid vigor, which results in seed yields that exceed that of either parent used in the formation of the $F_1$ hybrid. For example, yield can be at least 10% (e.g., 10% to 20%, 10% to 15%, 15% to 20%, or 25% to 35%) above that of either one or both parents. In some embodiments, the yield exceeds that of open-pollinated spring canola varieties such as 46A65 (Pioneer) or Q2 (University of Alberta), when grown under similar growing conditions. For example, yield can be at least 10% (e.g., 10% to 15% or 15% to 20%) above that of an open-pollinated variety.

Hybrids described herein typically produce seeds having very low levels of glucosinolates (<30 μmol/gram of de-fatted meal at a moisture content of 8.5%). In particular, hybrids can produce seeds having <20 μmol of glucosinolates/gram of de-fatted meal. As such, hybrids can incorporate mutations that confer low glucosinolate levels. See, for example, U.S. Pat. No. 5,866,762. Glucosinolate levels can be determined in accordance with known techniques, including high performance liquid chromatography (HPLC), as described in ISO 9167-1:1992(E), for quantification of total, intact glucosinolates, and gas-liquid chromatography for quantification of trimethylsilyl (TMS) derivatives of extracted and purified desulfoglucosinolates. Both the HPLC and TMS methods for determining glucosinolate levels analyze de-fatted or oil-free meal.

Canola Oil

*Brassica* plants disclosed herein are useful for producing canola oils with low ALA content. For example, oil obtained from seeds of *Brassica* plants described herein may have an ALA content of 0.5% to 1.6% (e.g., 0.5 to 1.5%, 0.5 to 1.0%, 0.5 to 0.8%, 0.6 to 1.4%, 0.6 to 1.3%, 0.6 to 1.2%, 0.6 to 1.1%, 0.6 to 1.0%, 0.6 to 0.8%, 0.7 to 1.2%, 0.7 to 1.1%, 0.8 to 1.2%, or 0.8 to 1.0%). In some embodiments, *Brassica* plants described herein produce canola oils with low ALA content (e.g., 0.5 to 1.6%) and low or no total saturated fatty acids. For example, oil obtained from seeds of *Brassica* plants described herein may have an ALA content of 0.5 to 1.5% and a total saturated fatty acid content of 2.5 to 6%, 3 to 5%, 3 to 4.5%, 3.25 to 3.75%, 3.0 to 3.5%, 3.4 to 3.7%, 3.6 to 5%, 4 to 5.5%, 4 to 5%, or 4.25 to 5.25%. The palmitic acid content of such oils can be 2.4 to 3.5% (e.g., 2.5 to 3% or 2.7 to 3.3%). The stearic acid content of such oils can be 0.7 to 2.5% (e.g., 0.8 to 1.7%, 0.9 to 1.5%, or 1.0 to 1.5%).

In some embodiments, an oil has an ALA content of 0.5 to 1.5%, an oleic acid content of 60 to 70% (e.g., 62 to 68%, 63 to 67%, or 65 to 66%), and a total saturated fatty acid content of 5 to 10%. In some embodiments, an oil has an ALA content of 0.6 to 1.5% (e.g., 0.7 to 1.4%, 0.8 to 1.3%, or 0.9 to 1.2%) and an oleic acid content of 71 to 80% (e.g., 72 to 78%, 72 to 76%, 73 to 75%, 74 to 77%, 74 to 78%, or 75 to 80%). The total saturated content of such an oil can be 3 to 8% (e.g., 4 to 6%, 4 to 5.5%, 4 to 5%, 5 to 7%, 6 to 8%, or 7 to 8%). In some embodiments, a canola oil can have an ALA content of 0.5 to 1.5%, an oleic acid content of 85 to 87% (e.g., 86 to 87%), and a total saturated fatty acid content of 5 to 6%. In some embodiments, an oil has an ALA content of 0.5 to 1.5%, an oleic acid content of 81 to 90% (e.g., 82 to 88% or 83 to 87%) oleic acid and a total saturated fatty acid content of 3.5 to 4.5% (e.g., 3.75 to 4.25%, 3.9 to 4.1%, or 4.0%).

Oils described herein can have an eicosenoic acid content of 1.0 to 1.9%. For example, an oil can have an eicosenoic acid content of 1.0 to 1.4%, 1.1 to 1.3%, 1.1 to 1.6%, 1.2 to 1.6%, 1.4 to 1.9%, in addition to a low ALA content.

Oils described herein can have a linoleic acid content of 3.5 to 26%, e.g., 3.7 to 4.5%, 8 to 10%, 9 to 12%, 10 to 13%, 11 to 13%, 12 to 16%, 13 to 16%, 14 to 18%, or 14 to 22%, in addition to a low ALA content.

Oils described herein have an erucic acid content of less than 2% (e.g., less than 1%, 0.5%, 0.2, or 0.1%) in addition to a low ALA content.

The fatty acid composition of seeds can be determined by first crushing and extracting oil from seed samples (e.g., bulk seeds samples of 10 or more seeds). TAGs in the seed are hydrolyzed to produce free fatty acids, which then can be converted to fatty acid methyl esters and analyzed using techniques known to the skilled artisan, e.g., gas-liquid chromatography (GLC) according to AOCS Procedure Ce 1e-91. Near infrared (NIR) analysis can be performed on whole seed according to AOCS Procedure Am-192 (revised 1999)

Seeds harvested from plants described herein can be used to make a crude canola oil or a refined, bleached, and deodorized (RBD) canola oil with a low ALA content. Harvested canola seed can be crushed to extract crude oil and, if desired, refined, bleached and deodorized by techniques known in the art. See, e.g., *Bailey's Industrial Oil and Fat Products*, Volume 5, "Edible Fat and Oil Products: Processing Technologies" (6th Edition, 2005). Briefly, refining refers to removing most if not all free fatty acids and other impurities such as phosphatides or protein substances from a crude oil. One common method of refining involves treating an oil with a strong base, followed by extensive washings with water. Bleaching refers to a process that removes natural pigments (e.g., carotenoids, chlorophylls, and xanthophylls) and other impurities such as metal cations (e.g., Fe, Cu and Zn). Bleaching can be done by absorbing such pigments and/or cations on a natural bleaching earth or clay, which is usually added to an oil under vacuum and high temperature. Deodorizing refers to the removal of relatively volatile trace components (e.g., ketones, aldehydes, alcohols) from an oil that contribute to flavor, odor, and color. Deodorizing is usually done by injecting steam into an oil heated to high temperatures (e.g., about 470° F. to about 510° F.) under high vacuum (e.g., <5 mm Hg).

In one useful example, the seed can be tempered by spraying the seed with water to raise the moisture to, for example, 8.5%. The tempered seed can be flaked using a smooth roller with, for example, a gap setting of 0.23 to 0.27 mm. Heat may be applied to the flakes to deactivate enzymes, facilitate further cell rupturing, coalesce the oil droplets, or agglomerate protein particles in order to ease the extraction process. Typically, oil is removed from the heated canola flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles. Further oil can be extracted from the press cake produced from the screw pressing operation using known solvent extraction techniques, e.g., using commercial n-hexane extraction. The canola oil recovered from the solvent extraction process is combined with the clarified oil from the screw pressing operation, resulting in a blended crude oil.

Free fatty acids and gums typically are removed from the crude oil by heating in a batch refining tank to which food grade phosphoric acid has been added. The acid serves to convert the non-hydratable phosphatides to a hydratable form, and to chelate minor metals that are present in the crude oil. The phosphatides and the metal salts are removed from the oil along with the soapstock. The oil-acid mixture is treated with sodium hydroxide solution to neutralize the free fatty acids and the phosphoric acid in the acid-oil mixture. The neutralized free fatty acids, phosphatides, etc. (soapstock) are drained off from the neutralized oil. A water wash may be done to further reduce the soap content of the oil. The oil may be bleached and deodorized before use, if desired, by techniques known in the art.

Oils obtained from plants described herein can have increased oxidative stability, which can be measured using, for example, an Oxidative Stability Index Instrument (e.g., from Omnion, Inc., Rockland, Mass.) according to AOCS Official Method Cd 12b-92 (revised 1993). Oxidative stability is often expressed in terms of "AOM" hours.

Oils obtained from plants described herein also can have increased flavor stability, which can be measured using, for example, trained test panels in room-odor tests according to Mounts, J. *Am. Oil Chem. Soc.* 56:659-663, 1979 and the AOCS Recommended Practice Cg 2-83 for the Flavor Evaluation of Vegetable Oils (Methods and Standard Practices of the AOCS, 4th Edition (1989)). The technique encompasses standard sample preparation and presentation, as well as reference standards and method for scoring oils.

Food Compositions

This document also features food compositions containing the oils described above. For example, oils having a low ALA content (e.g., 0.5 to 1.5%) can be used for food applications or for frying. Oils having a low ALA content in combination with a low (6% or less) or very low (3.5% or less) total saturated fatty acid content can be used to replace or reduce the amount of saturated fatty acids and hydrogenated oils (e.g., partially hydrogenated oils) in various food products such that the levels of saturated fatty acids and trans fatty acids are reduced in the food products. In particular, canola oils having a low ALA content in combination with a low total saturated fatty acid content and a mid or high oleic acid content can be used to replace or reduce the amount of saturated fats and partially hydrogenated oils in processed or packaged food products, including bakery products such as cookies, muffins, doughnuts, pastries (e.g., toaster pastries), pie fillings, pie crusts, pizza crusts, frostings, breads, biscuits, and cakes, breakfast cereals, breakfast bars, puddings, and crackers.

For example, an oil described herein can be used to produce sandwich cookies that contain no or reduced levels of partially hydrogenated oils in the cookie and/or crème filling. In some embodiments, the cookies also have a reduced total saturated fatty acid content. Such cookie compositions can include, for example, in addition to canola oil, flour, sweetener (e.g., sugar, molasses, honey, high fructose corn syrup, artificial sweetener such as sucralose, saccharine, aspartame, or acesulfame potassium, and combinations thereof), eggs, salt, flavorants (e.g., chocolate, vanilla, or lemon), a leavening agent (e.g., sodium bicarbonate or other baking acid such as monocalcium phosphate monohydrate, sodium aluminum sulfate, sodium acid pyrophosphate, sodium aluminum phosphate, dicalcium phosphate, glucano-deltalactone, or potassium hydrogen tartrate, or combinations thereof), and optionally, an emulsifier (e.g., mono- and diglycerides of fatty acids, propylene glycol mono- and di-esters of fatty acids, glycerol-lactose esters of fatty acids, ethoxylated or succinylated mono- and diglycerides, lecithin, diacetyl tartaric acid esters or mono- and diglycerides, sucrose esters of glycerol, and combinations thereof). A crème filling composition can include, in addition to canola oil, sweetener (e.g., powdered sugar, granulated sugar, honey, high fructose corn syrup, artificial sweetener, or combinations thereof), flavorant (e.g., vanilla, chocolate, or lemon), salt, and, optionally, emulsifier.

Canola oils (e.g., with a low ALA, low total saturated fatty acid and low or high oleic acid content) also are useful for frying applications due to the polyunsaturated content, which is low enough to have improved oxidative stability for frying yet high enough to impart the desired fried flavor to the food being fried. For example, canola oils can be used to produce fried foods such as snack chips (e.g., corn or potato chips), French fries, or other quick serve foods.

Oils described herein also can be used to formulate spray coatings for food products (e.g., cereals or snacks such as crackers). In some embodiments, the spray coating can include other vegetable oils such as sunflower, cottonseed, corn, or soybean oils. A spray coating also can include an antioxidant and/or a seasoning.

Oils described herein also can be use in the manufacturing of dressings, mayonnaises, and sauces to provide a reduction in the total saturated fat content of the product. Oils described herein can be used as a base oil for creating structured fat solutions such as microwave popcorn solid fats or canola butter formulations.

Plant Breeding

The nucleic acids described herein (e.g., fad3D and fad3E nucleic acids) can be used as markers in plant genetic mapping and plant breeding programs. Such markers may include restriction fragment length polymorphism (RFLP), random amplified polymorphic DNA detection (RAPD), amplified fragment length polymorphism (AFLP), simple sequence repeat (SSR) or microsatellite, for example. Marker-assisted breeding techniques may be used to identify and follow a desired fatty acid composition (e.g., low linolenic acid) during the breeding process. For example, a nucleic acid described herein, such as the nucleic acid sequence set forth in SEQ ID NO:1 or SEQ ID NO:32, or the complement thereof, can be used to identify one or more individual plants that possess the polymorphic allele correlated with the desired linolenic acid content. Those plants then can be used in a breeding program to combine the polymorphic allele with a plurality of other alleles at other loci that are correlated with a desired variation (e.g., in fatty acid composition). In some embodiments, a fragment of the nucleic acid sequence set forth in SEQ ID NO:1 or SEQ ID NO:32, or the complement thereof, that is at least 50 nucleotides in length can be used to distinguish a modified fad3 allele from a wild-type Fad3 allele (e.g., by allele-specific hybridization or by PCR).

Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plant is selfed or crossed to a different plant to produce seed, which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for disease resistance. Selection for such other traits can be carried out before, during or after identification of individual plants that possess the desired polymorphic allele.

Marker-assisted breeding techniques may be used in addition to, or as an alternative to, other sorts of identification techniques. An example of marker-assisted breeding is the use of PCR primers that specifically amplify a sequence containing a desired mutation in the fad3D or fad3E sequence.

The invention will be further described in the following examples, which do not limit the scope of the invention described in the claims.

EXAMPLES

In the Tables described herein, the fatty acids are referred to by the length of the carbon chain and number of double bonds within the chain. For example, C14:0 refers to myristic acid; C16:0 refers to palmitic acid; C18:0 refers to stearic acid; C18:1 refers to oleic acid; C18:2 refers to linoleic acid; C18:3 refers to ALA; C20:0 refers to archidic acid; C20:1 refers to eicosenoic acid; C22:0 refers to behenic acid; C22:1 refers to erucic acid; C24:0 refers to lignoceric acid; and C24:1 refers to nervonic acid. "Total Sats" refers to the total of C14:0, C16:0, C18:0, C20:0, C22:0, and C24:0. Representative fatty acid profiles are provided for each of the specified samples.

Unless otherwise indicated, all percentages refer to wt % based on total wt % of fatty acids (i.e., fatty acid moieties) in the oil as determined by measuring the FAME moieties in accordance with the modified version of ROCS Ce 1c-89 set forth in Example 1.

Example 1

Brassica Plant Lines 1904 and 2558

Plants producing an oil with a low ALA content were obtained by subjecting a population of *B. napus* IMC201 seeds to chemical mutagenesis and selecting for low linolenic acid content (<1.5%). The typical fatty acid composition of field grown IMC201 is 3.6% C16:0, 1.8% C18:0, 76% C18:1, 12.5% C18:2, 3% C18:3, 0.7% C20:0, 1.5% C20:1, 0.3% C22:0, 0% C22:1, with total saturates of 6.4%. Prior to mutagenesis, IMC201 seeds were pre-imbibed in 700 gm seed lots by soaking for 15 min then draining for 5 min at room temperature. This was repeated four times to soften the seed coat. The pre-imbibed seed then were treated with 4 mM methyl N-nitrosoguanidine (MNNG) for three hours. Following the treatment with MNNG, seeds were drained of the mutagen and rinsed with water for one hour. After removing the water, the seeds were treated with 52.5 mM ethyl methanesulfonate (EMS) for sixteen hours. Following the treatment with EMS, the seeds were drained of mutagen and rinsed with water for one and one half hours. This dual mutagen treatment produced an $LD_{50}$ with the seed population.

Lines 1904 and 2558 were selected from the mutagenized population of IMC201 seeds as follows. Three thousand bulk M2 generation seeds were planted. Upon maturity, M3 seed (2500 individuals) was harvested from 2500 M2 plants and analyzed via a modified method for gas chromatograph determination of fatty acid profile per the American Oil Chemist's Society protocol (AOCS Ce 1c-89). In accordance with AOCS Ce 1c-89, the oil from the seeds was first treated to convert the acylglycerols to fatty acid methyl esters ("FAMEs") and vials of the FAMEs were placed in a gas chromatograph for analysis in accordance with a modified version of American Oil Chemist's Society Official Method Ce 1-62 that employed an Agilent 6890 gas chromatograph (Agilent Technologies, Santa Clara, Calif.) equipped with a fused silica capillary column (5 m×0.180 mm and 0.20 μm film thickness) packed with a polyethylene glycol based DB-Wax® for liquid phase separation (J&W Scientific, Folsom, Calif.). Hydrogen (H2) was used as the carrier gas at a flow rate of 2.5 mL/min and the column temperature was isothermal at 200° C. Seed from each plant was tested via this method in replicates of two.

Lines 1904 and 2558 were identified as having low linolenic acid content in seed oil. M3 seeds of lines 1904 and 2558 were planted (50 per line) and the resulting plants were self pollinated. M4 seeds were harvested from the plants and bulk seed samples (approximately 20 seeds) were analyzed via GC. The results are presented in Table I Lines 1904 and 2558 had ALA contents ranging from approximately 0.70% to 1.95%. Line 1904 was deposited with the American Type Culture Collection (ATCC) under Accession No. PTA-11273 and line 2558 was deposited with the American Type Culture Collection (ATCC) under Accession No. PTA-11274.

TABLE 1

Fatty acid profile of harvested M4 generation mutant seed.

| RESCHID | C14:0 | C16:0 | C16:1 | C18:0 | C18:1 | C18:2 | C18:3 | C20:0 |
|---|---|---|---|---|---|---|---|---|
| M3B-1904-01 | 0.065 | 4.675 | 0.323 | 2.307 | 72.509 | 16.181 | 0.912 | 0.818 |
| M3B-1904-02 | 0.052 | 4.183 | 0.256 | 2.507 | 74.995 | 13.520 | 1.431 | 0.911 |
| M3B-1904-03 | 0.055 | 3.938 | 0.216 | 2.272 | 75.548 | 13.762 | 1.239 | 0.834 |
| M3B-1904-04 | 0.058 | 4.089 | 0.218 | 2.313 | 74.369 | 14.354 | 1.507 | 0.862 |
| M3B-1904-05 | 0.056 | 3.930 | 0.202 | 2.571 | 75.823 | 13.172 | 1.377 | 0.889 |
| M3B-1904-06 | 0.062 | 4.286 | 0.256 | 2.170 | 74.700 | 14.110 | 1.195 | 0.829 |
| M3B-1904-07 | 0.053 | 4.147 | 0.247 | 2.386 | 75.233 | 13.305 | 1.306 | 0.866 |
| M3B-1904-08 | 0.058 | 4.198 | 0.237 | 2.530 | 74.591 | 13.613 | 1.217 | 0.965 |
| M3B-1904-09 | 0.063 | 4.133 | 0.210 | 2.246 | 75.223 | 13.916 | 1.147 | 0.845 |
| M3B-1904-10 | 0.068 | 4.367 | 0.300 | 2.708 | 71.414 | 16.504 | 1.386 | 0.891 |
| M3B-1904-11 | 0.057 | 4.022 | 0.246 | 2.343 | 75.222 | 13.434 | 1.450 | 0.835 |
| M3B-1904-12 | 0.058 | 4.157 | 0.247 | 2.315 | 74.670 | 14.226 | 1.160 | 0.816 |
| M3B-1904-13 | 0.055 | 4.179 | 0.251 | 2.473 | 73.852 | 15.023 | 0.839 | 0.853 |
| M3B-1904-14 | 0.059 | 4.151 | 0.251 | 2.268 | 75.153 | 13.876 | 1.107 | 0.819 |
| M3B-1904-15 | 0.073 | 4.095 | 0.272 | 2.390 | 75.613 | 13.511 | 1.214 | 0.829 |
| M3B-1904-16 | 0.054 | 3.947 | 0.210 | 2.653 | 75.732 | 13.173 | 1.516 | 0.869 |
| M3B-1904-17 | 0.051 | 3.877 | 0.236 | 2.634 | 75.262 | 13.495 | 0.809 | 0.942 |
| M3B-1904-18 | 0.057 | 3.901 | 0.240 | 2.598 | 75.561 | 13.259 | 1.268 | 0.908 |
| M3B-1904-19 | 0.058 | 3.942 | 0.215 | 2.270 | 76.923 | 12.821 | 0.779 | 0.786 |
| M3B-1904-20 | 0.066 | 4.044 | 0.263 | 2.105 | 74.938 | 14.222 | 1.436 | 0.758 |
| M3B-1904-21 | 0.071 | 4.264 | 0.275 | 2.275 | 74.864 | 14.105 | 1.123 | 0.852 |
| M3B-1904-22 | 0.060 | 4.242 | 0.257 | 2.308 | 75.173 | 13.872 | 1.137 | 0.817 |
| M3B-1904-23 | 0.060 | 4.095 | 0.240 | 2.122 | 73.657 | 15.742 | 0.780 | 0.814 |
| M3B-1904-24 | 0.068 | 4.046 | 0.272 | 2.294 | 74.481 | 14.038 | 1.251 | 0.848 |
| M3B-1904-25 | 0.063 | 4.162 | 0.265 | 2.364 | 75.169 | 14.022 | 1.126 | 0.825 |
| M3B-1904-26 | 0.054 | 3.981 | 0.246 | 2.228 | 76.741 | 13.190 | 0.741 | 0.795 |
| M3B-1904-27 | 0.057 | 4.058 | 0.240 | 2.112 | 75.577 | 14.077 | 0.844 | 0.824 |
| M3B-1904-28 | 0.058 | 4.221 | 0.274 | 2.259 | 74.558 | 13.776 | 1.219 | 0.837 |
| M3B-1904-29 | 0.058 | 4.364 | 0.223 | 2.550 | 74.320 | 14.035 | 1.298 | 0.941 |
| M3B-1904-30 | 0.054 | 4.133 | 0.225 | 2.419 | 74.744 | 13.928 | 1.317 | 0.926 |
| M3B-1904-31 | 0.070 | 4.209 | 0.259 | 2.225 | 76.060 | 13.424 | 1.118 | 0.755 |
| M3B-1904-32 | 0.079 | 4.867 | 0.385 | 3.113 | 69.744 | 16.279 | 1.951 | 1.048 |
| M3B-1904-33 | 0.066 | 4.346 | 0.261 | 2.741 | 74.104 | 13.778 | 1.582 | 0.882 |
| M3B-1904-34 | 0.079 | 4.571 | 0.269 | 2.605 | 73.843 | 14.412 | 1.272 | 0.889 |
| M3B-1904-35 | 0.067 | 4.168 | 0.259 | 2.460 | 75.821 | 13.653 | 0.744 | 0.808 |
| M3B-1904-36 | 0.051 | 4.128 | 0.209 | 2.338 | 76.117 | 12.715 | 1.416 | 0.894 |
| M3B-1904-37 | 0.054 | 4.238 | 0.201 | 2.295 | 74.756 | 13.803 | 1.531 | 0.891 |
| M3B-1904-38 | 0.057 | 4.325 | 0.237 | 2.472 | 75.481 | 13.396 | 1.460 | 0.825 |
| M3B-1904-39 | 0.059 | 4.178 | 0.249 | 2.392 | 74.176 | 14.528 | 1.360 | 0.890 |
| M3B-1904-40 | 0.056 | 4.176 | 0.245 | 3.409 | 72.309 | 13.105 | 1.378 | 1.171 |

TABLE 1-continued

Fatty acid profile of harvested M4 generation mutant seed.

| | | | | | | | | |
|---|---|---|---|---|---|---|---|---|
| M3B-1904-41 | 0.057 | 4.141 | 0.239 | 2.392 | 75.487 | 13.894 | 1.077 | 0.841 |
| M3B-1904-42 | 0.054 | 3.947 | 0.225 | 2.488 | 74.792 | 14.490 | 1.131 | 0.831 |
| M3B-1904-43 | 0.051 | 3.985 | 0.226 | 2.263 | 75.686 | 13.277 | 1.570 | 0.823 |
| M3B-1904-44 | 0.052 | 4.137 | 0.202 | 2.677 | 75.733 | 12.649 | 1.506 | 0.950 |
| M3B-1904-45 | 0.052 | 3.929 | 0.195 | 2.280 | 75.101 | 14.334 | 1.117 | 0.836 |
| M3B-1904-46 | 0.060 | 4.354 | 0.283 | 2.577 | 73.385 | 13.857 | 1.635 | 0.975 |
| M3B-1904-47 | 0.062 | 4.373 | 0.291 | 2.473 | 74.242 | 13.602 | 1.288 | 0.870 |
| M3B-1904-48 | 0.054 | 4.074 | 0.233 | 2.174 | 75.247 | 13.779 | 1.143 | 0.830 |
| M3B-1904-49 | 0.059 | 4.125 | 0.253 | 2.093 | 74.920 | 14.379 | 0.909 | 0.804 |
| M3B-1904-50 | 0.060 | 4.157 | 0.235 | 2.037 | 74.522 | 14.402 | 1.539 | 0.786 |
| M3B-2558-01 | 0.067 | 3.772 | 0.244 | 3.251 | 78.153 | 10.081 | 0.785 | 1.208 |
| M3B-2558-02 | 0.058 | 3.674 | 0.218 | 2.989 | 78.233 | 10.027 | 1.181 | 1.095 |
| M3B-2558-03 | 0.062 | 4.123 | 0.308 | 3.329 | 76.058 | 11.181 | 1.293 | 1.209 |
| M3B-2558-04 | 0.065 | 4.134 | 0.295 | 2.915 | 75.964 | 12.077 | 0.974 | 1.029 |
| M3B-2558-05 | 0.058 | 4.108 | 0.283 | 3.267 | 77.220 | 10.413 | 1.176 | 1.160 |
| M3B-2558-06 | 0.064 | 3.801 | 0.254 | 3.057 | 78.311 | 9.731 | 1.076 | 1.094 |
| M3B-2558-07 | 0.048 | 3.660 | 0.231 | 2.788 | 76.319 | 12.244 | 1.262 | 1.023 |
| M3B-2558-08 | 0.069 | 3.845 | 0.275 | 3.494 | 76.433 | 10.690 | 1.309 | 1.271 |
| M3B-2558-09 | 0.055 | 3.852 | 0.281 | 2.987 | 77.339 | 10.931 | 1.184 | 0.988 |
| M3B-2558-10 | 0.055 | 3.864 | 0.267 | 3.079 | 77.765 | 9.847 | 1.509 | 1.103 |
| M3B-2558-11 | 0.056 | 3.833 | 0.261 | 3.043 | 78.849 | 9.032 | 0.933 | 1.164 |
| M3B-2558-12 | 0.049 | 3.996 | 0.218 | 2.955 | 77.218 | 11.409 | 0.814 | 1.056 |
| M3B-2558-13 | 0.057 | 3.899 | 0.246 | 3.409 | 76.902 | 10.934 | 1.205 | 1.135 |
| M3B-2558-14 | 0.056 | 3.984 | 0.223 | 3.775 | 78.095 | 8.899 | 1.184 | 1.323 |
| M3B-2558-15 | 0.052 | 3.762 | 0.231 | 3.088 | 77.908 | 10.410 | 1.186 | 1.078 |
| M3B-2558-16 | 0.053 | 3.865 | 0.245 | 3.360 | 77.868 | 9.754 | 1.223 | 1.176 |
| M3B-2558-17 | 0.056 | 4.070 | 0.244 | 3.064 | 78.090 | 10.426 | 1.190 | 1.061 |
| M3B-2558-18 | 0.073 | 4.064 | 0.259 | 2.869 | 76.821 | 11.402 | 0.878 | 1.053 |
| M3B-2558-19 | 0.062 | 3.835 | 0.250 | 3.165 | 76.790 | 11.196 | 1.159 | 1.143 |
| M3B-2558-20 | 0.071 | 3.987 | 0.289 | 3.482 | 76.133 | 10.992 | 1.238 | 1.240 |
| M3B-2558-21 | 0.072 | 4.100 | 0.341 | 3.147 | 76.942 | 10.636 | 1.212 | 1.111 |
| M3B-2558-22 | 0.055 | 3.875 | 0.279 | 2.700 | 76.780 | 11.604 | 1.486 | 0.930 |
| M3B-2558-23 | 0.063 | 4.113 | 0.266 | 3.179 | 76.201 | 11.527 | 0.962 | 1.128 |
| M3B-2558-24 | 0.058 | 3.779 | 0.252 | 2.895 | 77.381 | 10.867 | 1.161 | 1.035 |
| M3B-2558-25 | 0.054 | 4.008 | 0.266 | 3.123 | 76.541 | 11.413 | 1.142 | 1.115 |
| M3B-2558-26 | 0.063 | 3.956 | 0.283 | 3.197 | 76.084 | 11.172 | 1.262 | 1.166 |
| M3B-2558-27 | 0.057 | 4.003 | 0.297 | 2.820 | 74.978 | 13.117 | 1.192 | 0.989 |
| M3B-2558-28 | 0.061 | 3.837 | 0.277 | 3.584 | 75.859 | 11.272 | 1.217 | 1.235 |
| M3B-2558-29 | 0.056 | 3.879 | 0.275 | 2.685 | 75.620 | 12.874 | 1.307 | 0.977 |
| M3B-2558-31 | 0.059 | 3.933 | 0.266 | 2.919 | 76.965 | 11.336 | 0.918 | 1.097 |
| M3B-2558-32 | 0.059 | 3.876 | 0.287 | 3.005 | 76.378 | 11.972 | 0.854 | 1.017 |
| M3B-2558-33 | 0.060 | 4.204 | 0.271 | 3.251 | 74.489 | 12.869 | 1.378 | 1.132 |
| M3B-2558-34 | 0.089 | 4.307 | 0.314 | 3.290 | 73.974 | 13.250 | 1.204 | 1.106 |
| M3B-2558-35 | 0.053 | 3.747 | 0.208 | 3.144 | 77.721 | 10.975 | 0.722 | 1.128 |
| M3B-2558-36 | 0.056 | 4.071 | 0.281 | 2.911 | 76.432 | 11.760 | 1.244 | 1.027 |
| M3B-2558-37 | 0.053 | 3.931 | 0.265 | 3.287 | 76.237 | 11.366 | 1.446 | 1.141 |
| M3B-2558-39 | 0.067 | 3.998 | 0.303 | 3.160 | 75.020 | 12.561 | 1.320 | 1.066 |
| M3B-2558-40 | 0.051 | 3.895 | 0.251 | 3.493 | 76.324 | 10.978 | 1.476 | 1.190 |
| M3B-2558-41 | 0.068 | 3.709 | 0.257 | 3.452 | 76.017 | 11.107 | 1.491 | 1.183 |
| M3B-2558-42 | 0.062 | 3.932 | 0.258 | 3.214 | 76.168 | 11.541 | 1.138 | 1.094 |
| M3B-2558-43 | 0.054 | 3.846 | 0.248 | 3.215 | 75.801 | 12.266 | 1.135 | 1.090 |
| M3B-2558-44 | 0.051 | 3.782 | 0.279 | 3.271 | 76.059 | 11.827 | 1.487 | 1.082 |
| M3B-2558-45 | 0.060 | 3.787 | 0.252 | 3.053 | 76.253 | 11.901 | 1.163 | 1.007 |
| M3B-2558-46 | 0.054 | 3.758 | 0.255 | 3.377 | 78.569 | 9.676 | 0.844 | 1.183 |
| M3B-2558-47 | 0.060 | 3.981 | 0.277 | 3.142 | 76.833 | 11.297 | 0.823 | 1.082 |
| M3B-2558-48 | 0.052 | 3.816 | 0.264 | 3.204 | 76.778 | 11.235 | 1.305 | 1.112 |
| M3B-2558-49 | 0.053 | 4.068 | 0.277 | 3.172 | 75.712 | 11.904 | 1.645 | 1.054 |
| M3B-2558-50 | 0.059 | 4.063 | 0.282 | 3.440 | 75.763 | 11.199 | 1.607 | 1.126 |

| RESCHID | C20:1 | C20:2 | C22:0 | C22:1 | C24:0 | C24:1 | TOT SATS |
|---|---|---|---|---|---|---|---|
| M3B-1904-01 | 1.068 | 0.046 | 0.410 | 0.000 | 0.210 | 0.475 | 8.486 |
| M3B-1904-02 | 1.180 | 0.046 | 0.453 | 0.000 | 0.267 | 0.201 | 8.372 |
| M3B-1904-03 | 1.284 | 0.048 | 0.421 | 0.000 | 0.250 | 0.133 | 7.771 |
| M3B-1904-04 | 1.234 | 0.052 | 0.437 | 0.017 | 0.243 | 0.247 | 8.003 |
| M3B-1904-05 | 1.133 | 0.044 | 0.407 | 0.000 | 0.210 | 0.186 | 8.063 |
| M3B-1904-06 | 1.206 | 0.050 | 0.463 | 0.000 | 0.258 | 0.415 | 8.068 |
| M3B-1904-07 | 1.259 | 0.047 | 0.443 | 0.000 | 0.219 | 0.491 | 8.113 |
| M3B-1904-08 | 1.315 | 0.052 | 0.526 | 0.031 | 0.307 | 0.359 | 8.584 |
| M3B-1904-09 | 1.215 | 0.048 | 0.436 | 0.021 | 0.237 | 0.260 | 7.959 |
| M3B-1904-10 | 1.190 | 0.060 | 0.443 | 0.000 | 0.304 | 0.364 | 8.780 |
| M3B-1904-11 | 1.228 | 0.045 | 0.418 | 0.000 | 0.220 | 0.481 | 7.895 |
| M3B-1904-12 | 1.215 | 0.045 | 0.395 | 0.000 | 0.198 | 0.498 | 7.939 |
| M3B-1904-13 | 1.227 | 0.051 | 0.418 | 0.000 | 0.238 | 0.540 | 8.217 |
| M3B-1904-14 | 1.190 | 0.049 | 0.433 | 0.000 | 0.249 | 0.394 | 7.979 |
| M3B-1904-15 | 1.144 | 0.042 | 0.389 | 0.000 | 0.207 | 0.222 | 7.983 |
| M3B-1904-16 | 1.146 | 0.043 | 0.374 | 0.000 | 0.181 | 0.104 | 8.077 |

TABLE 1-continued

Fatty acid profile of harvested M4 generation mutant seed.

| | | | | | | | |
|---|---|---|---|---|---|---|---|
| M3B-1904-17 | 1.277 | 0.051 | 0.480 | 0.000 | 0.266 | 0.621 | 8.250 |
| M3B-1904-18 | 1.190 | 0.046 | 0.434 | 0.000 | 0.228 | 0.311 | 8.126 |
| M3B-1904-19 | 1.153 | 0.046 | 0.389 | 0.000 | 0.198 | 0.423 | 7.642 |
| M3B-1904-20 | 1.215 | 0.044 | 0.373 | 0.000 | 0.217 | 0.320 | 7.561 |
| M3B-1904-21 | 1.193 | 0.044 | 0.424 | 0.000 | 0.245 | 0.265 | 8.131 |
| M3B-1904-22 | 1.130 | 0.045 | 0.392 | 0.000 | 0.208 | 0.361 | 8.025 |
| M3B-1904-23 | 1.360 | 0.059 | 0.451 | 0.000 | 0.284 | 0.336 | 7.825 |
| M3B-1904-24 | 1.372 | 0.048 | 0.468 | 0.036 | 0.238 | 0.541 | 7.962 |
| M3B-1904-25 | 1.134 | 0.042 | 0.384 | 0.000 | 0.208 | 0.235 | 8.007 |
| M3B-1904-26 | 1.133 | 0.042 | 0.398 | 0.000 | 0.193 | 0.259 | 7.648 |
| M3B-1904-27 | 1.311 | 0.050 | 0.466 | 0.024 | 0.233 | 0.127 | 7.750 |
| M3B-1904-28 | 1.348 | 0.049 | 0.458 | 0.000 | 0.230 | 0.713 | 8.063 |
| M3B-1904-29 | 1.236 | 0.051 | 0.484 | 0.000 | 0.289 | 0.150 | 8.687 |
| M3B-1904-30 | 1.296 | 0.054 | 0.501 | 0.000 | 0.264 | 0.140 | 8.297 |
| M3B-1904-31 | 1.010 | 0.043 | 0.348 | 0.000 | 0.165 | 0.316 | 7.771 |
| M3B-1904-32 | 1.272 | 0.066 | 0.548 | 0.000 | 0.350 | 0.300 | 10.005 |
| M3B-1904-33 | 1.079 | 0.049 | 0.405 | 0.000 | 0.253 | 0.455 | 8.693 |
| M3B-1904-34 | 1.063 | 0.050 | 0.430 | 0.000 | 0.197 | 0.319 | 8.771 |
| M3B-1904-35 | 1.069 | 0.040 | 0.356 | 0.000 | 0.171 | 0.386 | 8.029 |
| M3B-1904-36 | 1.240 | 0.048 | 0.467 | 0.000 | 0.245 | 0.132 | 8.122 |
| M3B-1904-37 | 1.301 | 0.049 | 0.471 | 0.000 | 0.266 | 0.145 | 8.215 |
| M3B-1904-38 | 1.062 | 0.045 | 0.357 | 0.000 | 0.181 | 0.103 | 8.216 |
| M3B-1904-39 | 1.257 | 0.047 | 0.456 | 0.000 | 0.288 | 0.121 | 8.262 |
| M3B-1904-40 | 1.309 | 0.054 | 0.610 | 0.000 | 0.400 | 1.777 | 9.823 |
| M3B-1904-41 | 1.121 | 0.044 | 0.410 | 0.000 | 0.195 | 0.103 | 8.036 |
| M3B-1904-42 | 1.242 | 0.046 | 0.388 | 0.000 | 0.220 | 0.145 | 7.928 |
| M3B-1904-43 | 1.298 | 0.046 | 0.425 | 0.000 | 0.203 | 0.146 | 7.751 |
| M3B-1904-44 | 1.217 | 0.046 | 0.456 | 0.000 | 0.221 | 0.155 | 8.493 |
| M3B-1904-45 | 1.307 | 0.047 | 0.445 | 0.000 | 0.225 | 0.133 | 7.767 |
| M3B-1904-46 | 1.233 | 0.053 | 0.550 | 0.000 | 0.317 | 0.721 | 8.833 |
| M3B-1904-47 | 1.232 | 0.047 | 0.451 | 0.000 | 0.246 | 0.824 | 8.475 |
| M3B-1904-48 | 1.333 | 0.051 | 0.454 | 0.020 | 0.266 | 0.343 | 7.851 |
| M3B-1904-49 | 1.281 | 0.057 | 0.457 | 0.000 | 0.248 | 0.416 | 7.786 |
| M3B-1904-50 | 1.209 | 0.053 | 0.425 | 0.015 | 0.233 | 0.329 | 7.698 |
| M3B-2558-01 | 1.313 | 0.037 | 0.583 | 0.016 | 0.354 | 0.137 | 9.234 |
| M3B-2558-02 | 1.326 | 0.045 | 0.547 | 0.016 | 0.305 | 0.288 | 8.668 |
| M3B-2558-03 | 1.278 | 0.045 | 0.604 | 0.000 | 0.362 | 0.150 | 9.689 |
| M3B-2558-04 | 1.325 | 0.046 | 0.509 | 0.000 | 0.304 | 0.364 | 8.956 |
| M3B-2558-05 | 1.259 | 0.044 | 0.545 | 0.000 | 0.332 | 0.136 | 9.469 |
| M3B-2558-06 | 1.302 | 0.039 | 0.523 | 0.000 | 0.292 | 0.456 | 8.831 |
| M3B-2558-07 | 1.394 | 0.059 | 0.511 | 0.000 | 0.254 | 0.208 | 8.283 |
| M3B-2558-08 | 1.372 | 0.044 | 0.643 | 0.000 | 0.374 | 0.181 | 9.696 |
| M3B-2558-09 | 1.206 | 0.038 | 0.442 | 0.000 | 0.232 | 0.464 | 8.556 |
| M3B-2558-10 | 1.261 | 0.041 | 0.539 | 0.000 | 0.303 | 0.369 | 8.942 |
| M3B-2558-11 | 1.377 | 0.040 | 0.618 | 0.000 | 0.388 | 0.408 | 9.102 |
| M3B-2558-12 | 1.282 | 0.047 | 0.516 | 0.000 | 0.300 | 0.140 | 8.872 |
| M3B-2558-13 | 1.254 | 0.044 | 0.523 | 0.000 | 0.297 | 0.094 | 9.321 |
| M3B-2558-14 | 1.297 | 0.040 | 0.637 | 0.000 | 0.350 | 0.137 | 10.125 |
| M3B-2558-15 | 1.305 | 0.045 | 0.521 | 0.000 | 0.297 | 0.117 | 8.797 |
| M3B-2558-16 | 1.231 | 0.038 | 0.545 | 0.000 | 0.329 | 0.313 | 9.328 |
| M3B-2558-17 | 1.284 | 0.000 | 0.516 | 0.000 | 0.000 | 0.000 | 8.767 |
| M3B-2558-18 | 1.301 | 0.041 | 0.530 | 0.000 | 0.276 | 0.433 | 8.866 |
| M3B-2558-19 | 1.325 | 0.043 | 0.546 | 0.000 | 0.314 | 0.172 | 9.065 |
| M3B-2558-20 | 1.328 | 0.042 | 0.593 | 0.000 | 0.384 | 0.220 | 9.758 |
| M3B-2558-21 | 1.247 | 0.040 | 0.537 | 0.000 | 0.340 | 0.276 | 9.306 |
| M3B-2558-22 | 1.214 | 0.039 | 0.427 | 0.000 | 0.215 | 0.396 | 8.201 |
| M3B-2558-23 | 1.313 | 0.045 | 0.576 | 0.000 | 0.340 | 0.287 | 9.399 |
| M3B-2558-24 | 1.302 | 0.045 | 0.514 | 0.023 | 0.307 | 0.381 | 8.588 |
| M3B-2558-25 | 1.302 | 0.046 | 0.535 | 0.017 | 0.304 | 0.134 | 9.140 |
| M3B-2558-26 | 1.310 | 0.047 | 0.607 | 0.017 | 0.363 | 0.474 | 9.351 |
| M3B-2558-27 | 1.321 | 0.049 | 0.506 | 0.027 | 0.288 | 0.356 | 8.663 |
| M3B-2558-28 | 1.294 | 0.044 | 0.596 | 0.025 | 0.353 | 0.348 | 9.666 |
| M3B-2558-29 | 1.327 | 0.056 | 0.510 | 0.000 | 0.288 | 0.147 | 8.394 |
| M3B-2558-31 | 1.354 | 0.048 | 0.583 | 0.000 | 0.367 | 0.155 | 8.958 |
| M3B-2558-32 | 1.250 | 0.042 | 0.490 | 0.000 | 0.273 | 0.499 | 8.719 |
| M3B-2558-33 | 1.289 | 0.054 | 0.564 | 0.000 | 0.301 | 0.138 | 9.513 |
| M3B-2558-34 | 1.239 | 0.047 | 0.518 | 0.000 | 0.284 | 0.379 | 9.593 |
| M3B-2558-35 | 1.312 | 0.042 | 0.532 | 0.000 | 0.296 | 0.121 | 8.899 |
| M3B-2558-36 | 1.287 | 0.050 | 0.523 | 0.000 | 0.243 | 0.115 | 8.831 |
| M3B-2558-37 | 1.281 | 0.045 | 0.519 | 0.000 | 0.306 | 0.124 | 9.237 |
| M3B-2558-39 | 1.283 | 0.048 | 0.515 | 0.000 | 0.303 | 0.356 | 9.110 |
| M3B-2558-40 | 1.281 | 0.046 | 0.557 | 0.000 | 0.335 | 0.125 | 9.520 |
| M3B-2558-41 | 1.251 | 0.044 | 0.577 | 0.000 | 0.344 | 0.502 | 9.332 |

TABLE 1-continued

Fatty acid profile of harvested M4 generation mutant seed.

| | | | | | | | |
|---|---|---|---|---|---|---|---|
| M3B-2558-42 | 1.247 | 0.044 | 0.525 | 0.000 | 0.284 | 0.493 | 9.111 |
| M3B-2558-43 | 1.339 | 0.049 | 0.521 | 0.000 | 0.309 | 0.128 | 9.034 |
| M3B-2558-44 | 1.226 | 0.049 | 0.492 | 0.000 | 0.277 | 0.120 | 8.954 |
| M3B-2558-45 | 1.259 | 0.047 | 0.473 | 0.015 | 0.259 | 0.472 | 8.638 |
| M3B-2558-46 | 1.269 | 0.036 | 0.551 | 0.000 | 0.318 | 0.110 | 9.241 |
| M3B-2558-47 | 1.261 | 0.038 | 0.510 | 0.000 | 0.291 | 0.405 | 9.065 |
| M3B-2558-48 | 1.282 | 0.045 | 0.531 | 0.000 | 0.265 | 0.111 | 8.980 |
| M3B-2558-49 | 1.188 | 0.047 | 0.493 | 0.000 | 0.273 | 0.114 | 9.114 |
| M3B-2558-50 | 1.215 | 0.042 | 0.503 | 0.000 | 0.272 | 0.431 | 9.462 |

Selected M4 individuals were self pollinated to generate M5 seeds and further evaluated in an environmentally controlled plant growth chamber. Seeds from M3B-2558-35 and M3-B1904-35 were planted in Premier Pro-Mix BX potting soil (Premier Horticulture, Quebec, Canada) in four inch plastic pots. Planted seeds were watered and stratified at 5° C. for 5 days and germinated at 20° C. day temperature and 17° C. night temperature (20/17) in Conviron ATC60 controlled-environment growth chambers (Controlled Environments Limited, Winnipeg, MB). Each genotype combination was randomized and replicated 10 times in each of two separate growth chambers. At flowering, one chamber was reduced to a diurnal temperature cycle of 15° C. day temperature and 12° C. night temperature (15/12) while the other remained at 20/17. The temperature treatments were imposed to identify the effects of temperature on fatty acid composition. Plants were watered five times per week and fertilized bi-weekly using a 20:20:20 (NPK) liquid fertilizer at a rate of 150 ppm. Plants were bagged individually to ensure self pollination and genetic purity of the seed. Seeds from each plant were harvested individually at physiological seed maturity. The fatty acid profile of the seeds was determined using the modified GC method described above (replicates of two).

Fatty acid data from plants grown under the different temperature regimes was analyzed in two ways. First, data was analyzed separately as different environments and then it was pooled and analyzed across environments. Data was analyzed in SAS (SAS Institute, 2003) using proc glm to estimate differences in mean fatty acid values. Table 2 contains the population size, mean value and standard deviation of oleic, linoleic and linolenic fatty acid of seeds produced by plants carrying mutant fad3 alleles and grown in two environmental growth chambers set at different diurnal temperature regimes (20° C. day/17° C. night; 15° C. day/12° C. night) as discussed above. Genotypes 1904-35 and 2558-35 are mutant allele combinations and v1030 hybrid and IMC02 are controls. The 1904-35, 2558-35, and IMC02 lines each contain mutant fad3A and fad3B alleles, while line 1904-35 also contains a mutant fad3E allele and a mutant fad3D allele (see below). Means with different letters are significantly different as determined by a Student-Newman-Keuls mean separation test. In conclusion, lines 1904-35 and 2558-35 can reach an alpha-linolenic content less than v1030 and IMC02.

Seeds of lines 1904 and 2558 were deposited with the American Type Culture Collection (ATCC) (Manassas, Va.) on Sep. 1, 2010, under conditions of the Budapest Treaty and assigned Accession Nos. PTA-11273 and PTA-11274, respectively. All restrictions upon public access to the deposits will be irrevocably removed upon grant of the patent. The deposits will be replaced if the depository cannot dispense viable samples.

TABLE 2

Mean oleic, linoleic and linolenic acid content in two environments

| RESCHID | Mean C18:1 | s.d. | Mean C18:2 | s.d. | Mean C18:3 | s.d. | N |
|---|---|---|---|---|---|---|---|
| | | | 15/12 Environment | | | | |
| v1030 | 65.877 | 0.564 | 22.031 | 0.523 | 3.430 a | 0.116 | 9 |
| IMC02 | 69.728 | 1.528 | 20.484 | 1.434 | 1.815 b | 0.109 | 9 |
| 1904-35 | 73.986 | 1.437 | 16.956 | 1.369 | 1.071 c | 0.082 | 10 |
| 2558-35 | 77.276 | 1.191 | 13.051 | 1.505 | 0.976 d | 0.081 | 10 |
| | | | 17/20 Environment | | | | |
| v1030 | 65.053 | 1.397 | 22.906 | 1.570 | 2.952 a | 0.133 | 10 |
| IMC02 | 72.211 | 1.604 | 17.543 | 1.986 | 1.378 b | 0.098 | 10 |
| 1904-35 | 77.009 | 0.475 | 13.477 | 0.489 | 1.052 c | 0.040 | 9 |
| 2558-35 | 78.470 | 0.924 | 11.238 | 1.129 | 0.993 c | 0.080 | 10 |
| | | | Across Environments | | | | |
| V1030 | 65.443 | 1.138 | 22.491 | 1.247 | 3.179 a | 0.274 | 19 |
| IMC02 | 71.035 | 1.987 | 18.936 | 2.272 | 1.585 b | 0.246 | 19 |
| 1904-35 | 75.418 | 1.881 | 15.308 | 2.056 | 1.062 c | 0.065 | 19 |
| 2558-35 | 77.873 | 1.205 | 12.145 | 1.595 | 0.984 c | 0.079 | 20 |

Example 2

Identification of a Fad3E Mutation in 1904-35 Plants

Genome mapping, map-based gene cloning, and direct-sequencing strategies were used to identify loci associated with the <1.5% linolenic fatty acid content in the 1904-35 line described in Example 1. A DH (doubled haploid) population was developed from a cross between 1904-35 and 95CB504, a B line (maintainer). The two parental lines were screened with 1066 SNP (single nucleotide polymorphism) markers using the MassARRAY platform (Sequenom Inc., San Diego, Calif.) to identify polymorphic SNP markers between the two parents; 174 polymorphic SNP markers were identified.

Single marker correlations and multiple regression analysis between fatty acid composition and SNP markers were carried out using the SAS program (SAS Institute 1988). A Brassica napus genetic linkage map was constructed using the Kosambi function in JoinMap 3.0 (Kyazma). Interval mapping for quantitative trait loci (QTL) was done with MapQTL 4.0 (Kyazma). A LOD score >3.0 was considered as the significance threshold to declare the association intervals.

Comparative genome mapping was performed to locate the identified QTL in Brassica napus chromosomes and further identify the Brassica rapa BAC (Bacterial Artificial Chromosome) clones encompassing the identified SNP markers and the candidate genes in the identified QTL interval for the <1.5% linolenic acid content using publicly available Brassica and Arabidopsis genome sequences, genes, genetic linkage maps, and other information from the world wide web at brassica.bbsrc.ac.uk/, and ncbi.nlm.nih.gov/.

A total of 217 DH lines were genotyped with 174 polymorphic SNP markers. QTL mapping identified two QTLs for low linolenic acid content (<1.5% C18:3). Comparative genome mapping located one QTL on the N3 chromosome in *Brassica napus* (A3 in *Brassica rapa*) and further identified a Fad3E candidate gene which is located at 1cM from the SNP marker that showed significant association with C18:3 content. The 1cM interval between the SNP marker and Fad3E gene is 248 kb according to co-linearity with the *Arabidopsis* genome. Example 3 describes the second QTL on the N5 chromosome in *Brassica napus* (A5 in *Brassica rapa*).

Figure 2:
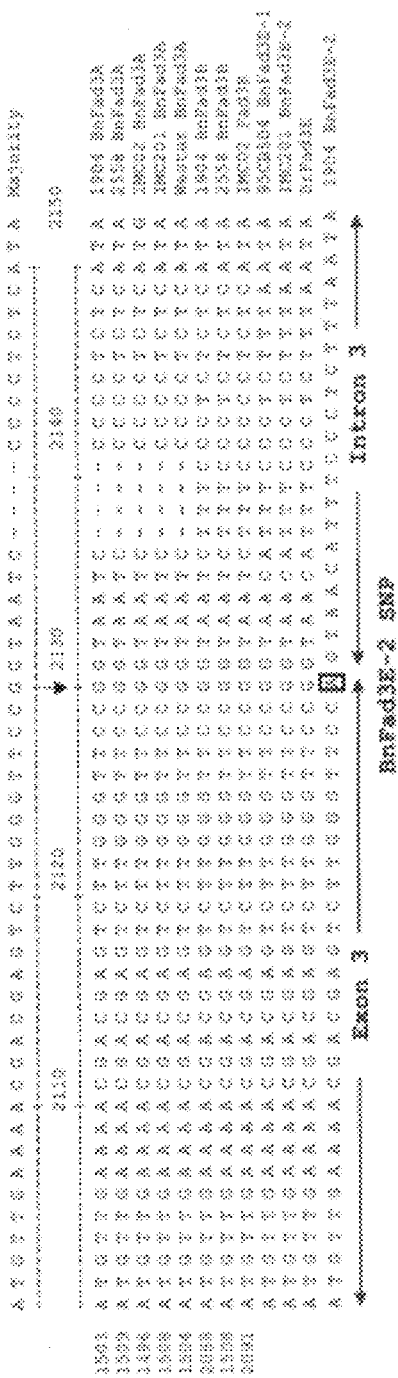
FIG. 2 is an alignment of the nucleotide sequence of the exon 3, intron 3 border of the BnFad3A, BnFad3B, BnFad3E genes from IMC201, IMC02, Westar, 1904, 2558, and 95CB504, and the BrFad3E gene from *Brassica rapa* (world wide web at brassica-rapa.org) showing the single nucleotide mutation (G to A) in BnFad3E-2 from the 1904 line. See SEQ ID NOs:4-8. This mutation (G to A) is located in the last nucleotide of exon 3 of BnFad3E. Intron 3 of the BnFad3E starts from the sequence GT (see SEQ ID NO:8).
Figure 3:
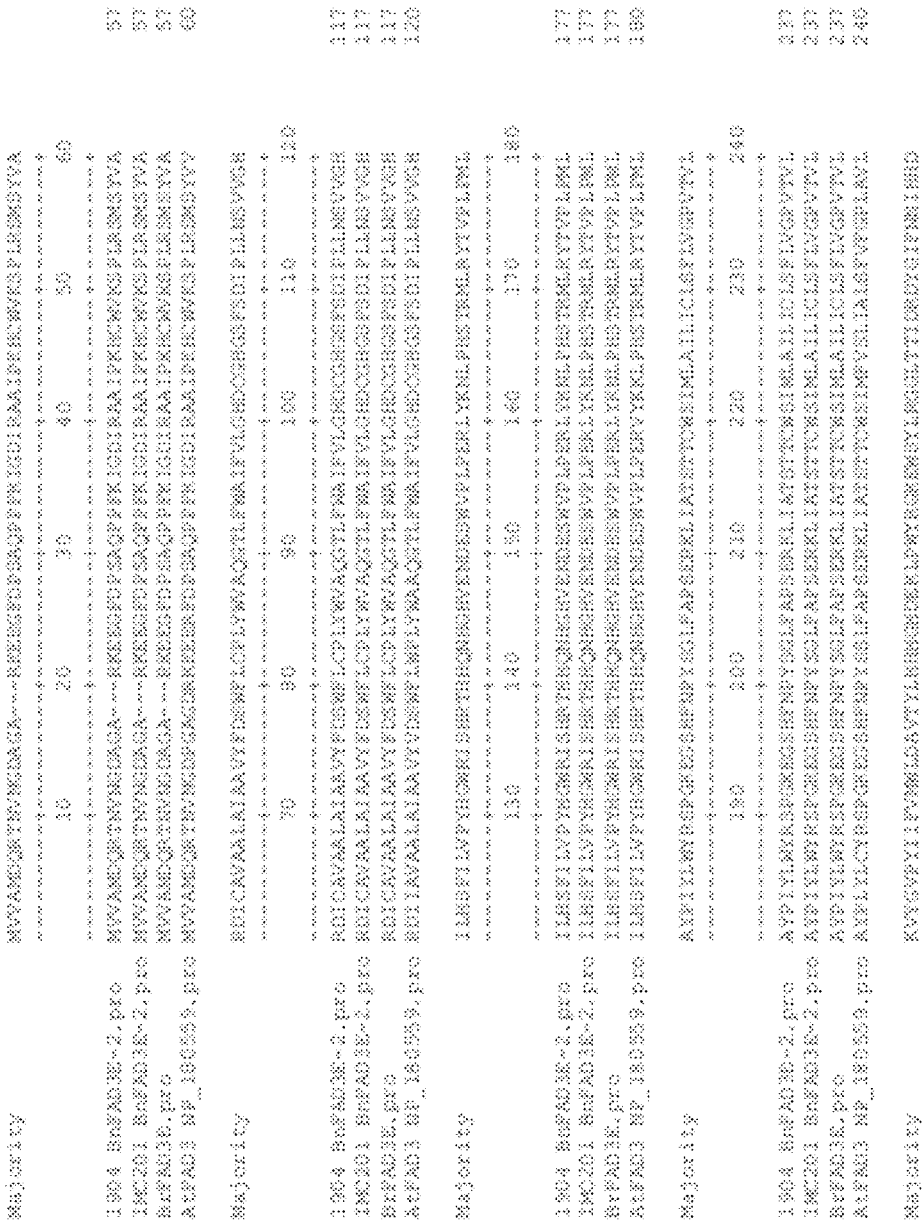
FIG. 3 is an alignment of the amino acid sequences of FAD3E polypeptides from *B. napus* and *B. rapa*, and FAD3 from *Arabidopsis thaliana*. See SEQ ID NOs:29, 30, and 31.

The Fad3E genes from chromosome N3 of the *Brassica napus* genome were sequenced from 1904-35, 95CB504 and IMC201. The sequences were analyzed using BLAST (the Basic Local Alignment Search Tool) and DNASTAR/Lasergene 8.0 (DNASTAR, Inc). A single nucleotide substitution was identified in one of the two Fad3E isoforms from the 1904-35 mutant line that was not present in 95CB504 and IMC201. FIG. 1 shows the sequence alignment of the BnFad3E gene from 1904-35 and IMC201, and the BrFad3E located in *Brassica rapa* BAC, KBrH013B15 from the world wide web at brassica-rapa.org. The nucleotide substitution of a "A" in 1904-35 for "G" in IMC201 and 95CB504 at position 1851 of this alignment (position 1756 in SEQ ID:NO:1). As shown in FIG. 2, this transition mutation of Fad3E is at the exon 3, intron 3 border. FIG. 3 shows the alignment of FAD3E amino acid sequences from 1904 BnFAD3E-2 and IMC201 BnFAD3E-2 (SEQ ID NO:29), BrFAD3E deduced from BrFad3E (world wide web at brassica-rapa.org) (SEQ ID NO:30), and AtFAD3 (GenBank accession number: NP_180559; SEQ ID NO:31). The fad3E-2 SNP allele results in an altered consensus sequence at the "splice donor site" for RNA splicing. Therefore, the RNA splicing of fad3E-2 primary transcript (pre-mRNA) cannot be processed to create a mature RNA (mRNA).

Large scale screening of the parental lines (1904-35 and 95CB504) as well as other *Brassica napus* cultivars including 2558, indicated the fad3E-2 SNP allele was 1904-35-specific and was significantly associated with the low ALA phenotype (R-square=0.275 for C18:3 content) using 217 DH lines developed from the cross between 1904-35 and 95CB504. This 1904-35 fad3E-2 SNP allele also was present in selections having <1.5% C18:3 content from a backcross population developed from the cross between 1904-35 and 1035R, an R line (restorer).

Example 3

Identification of a Fad3D Mutation in 1904-35 Plants

Figure 4:
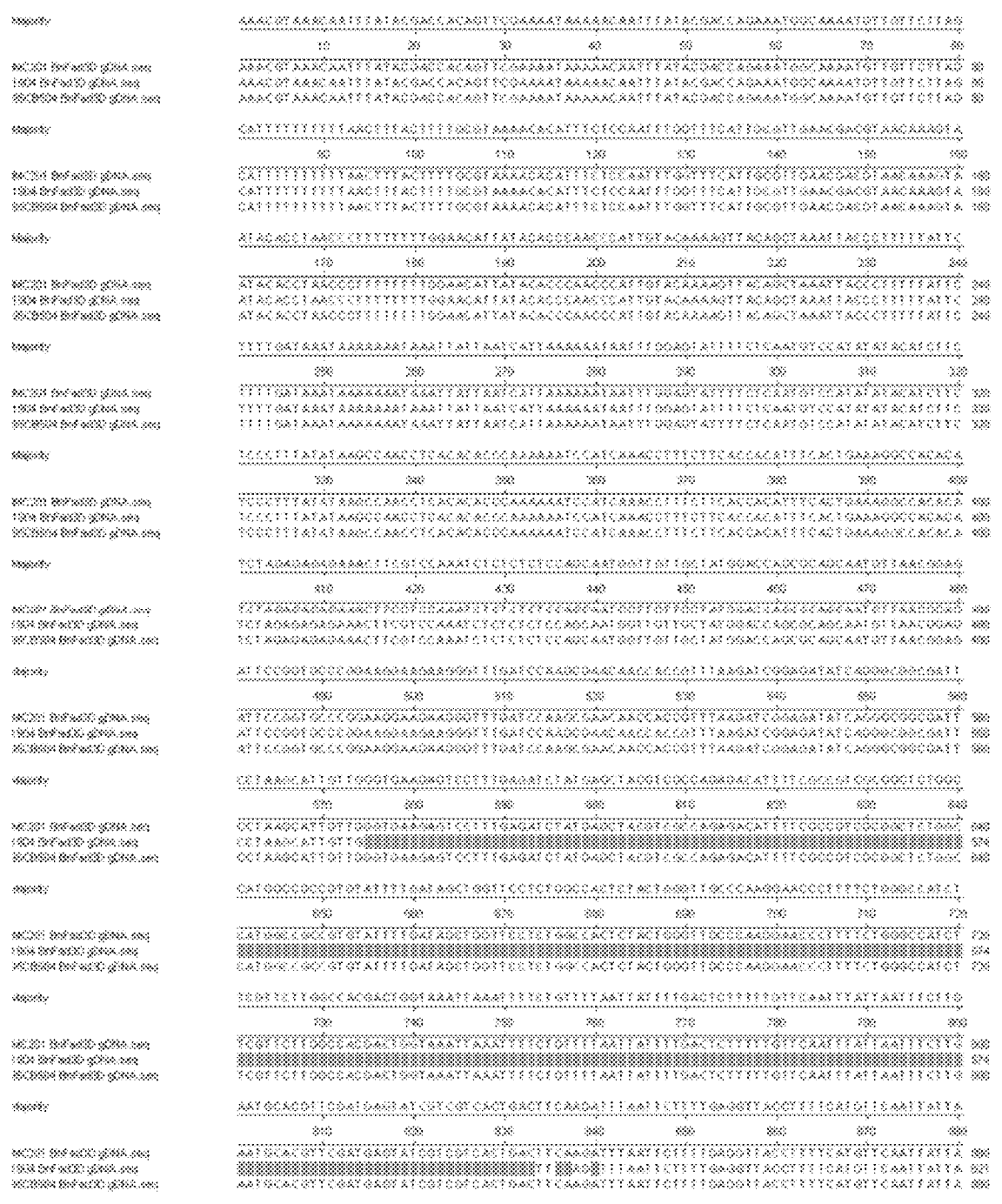
Figure 4:
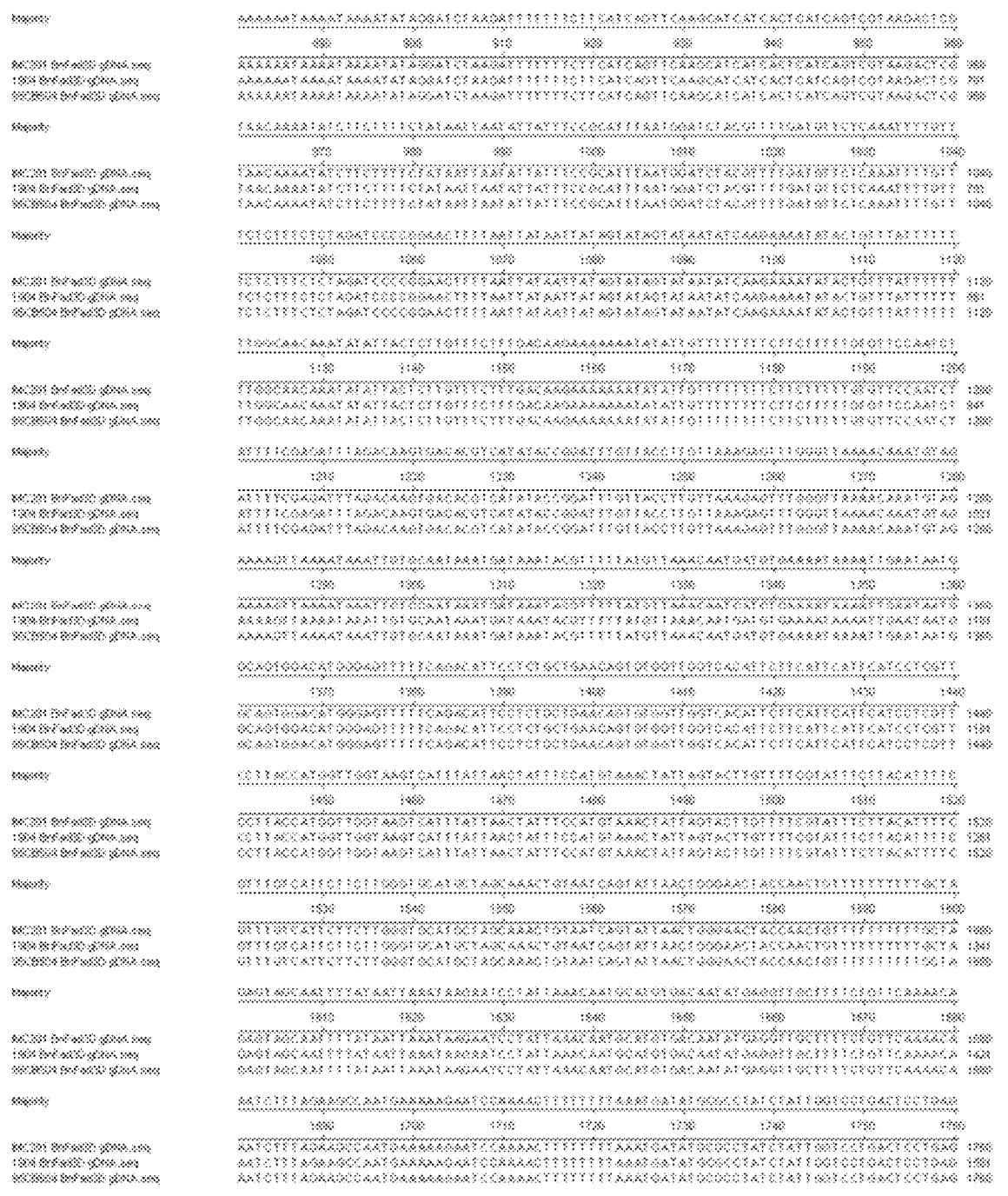
Figure 4:
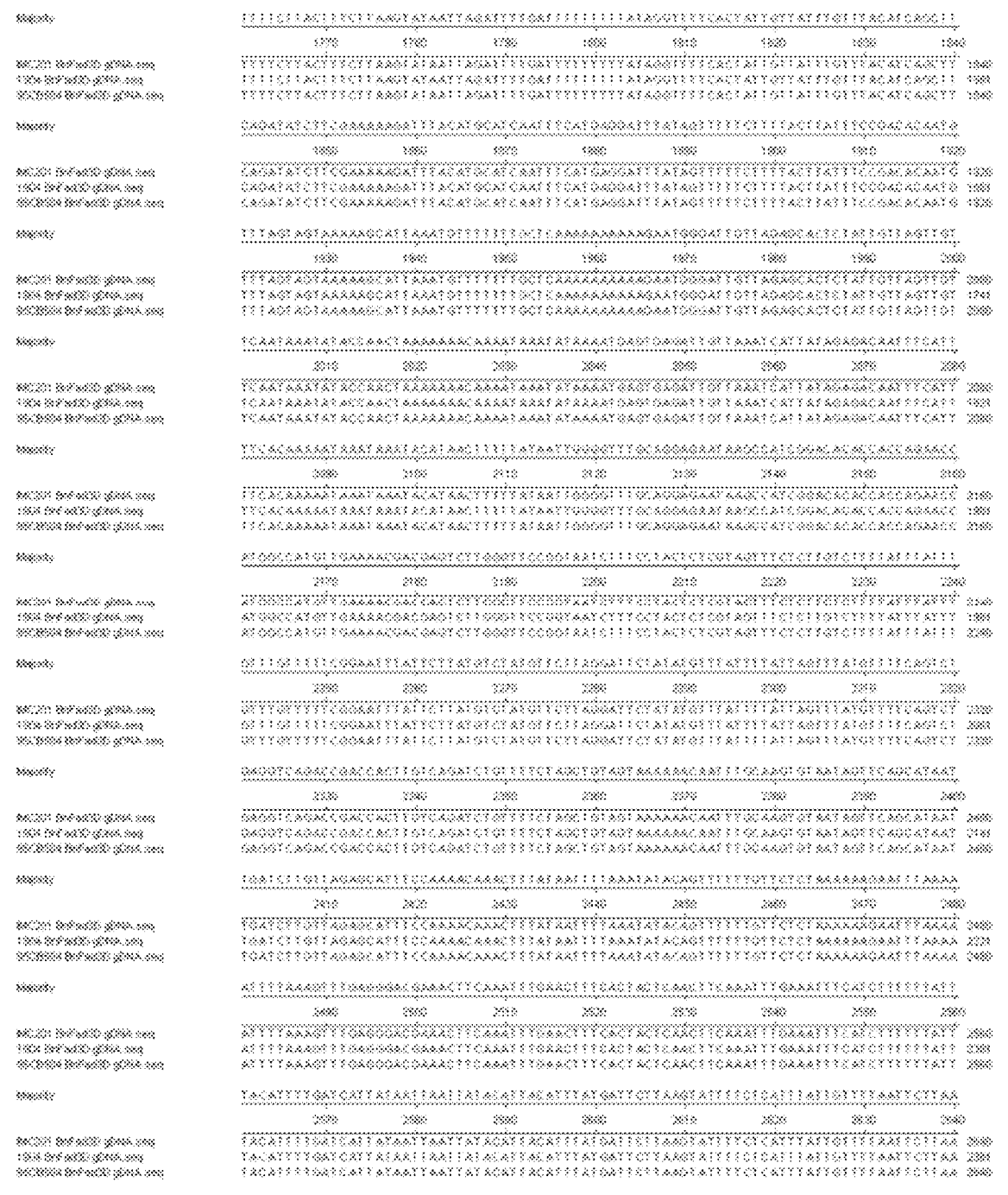
Figure 4:
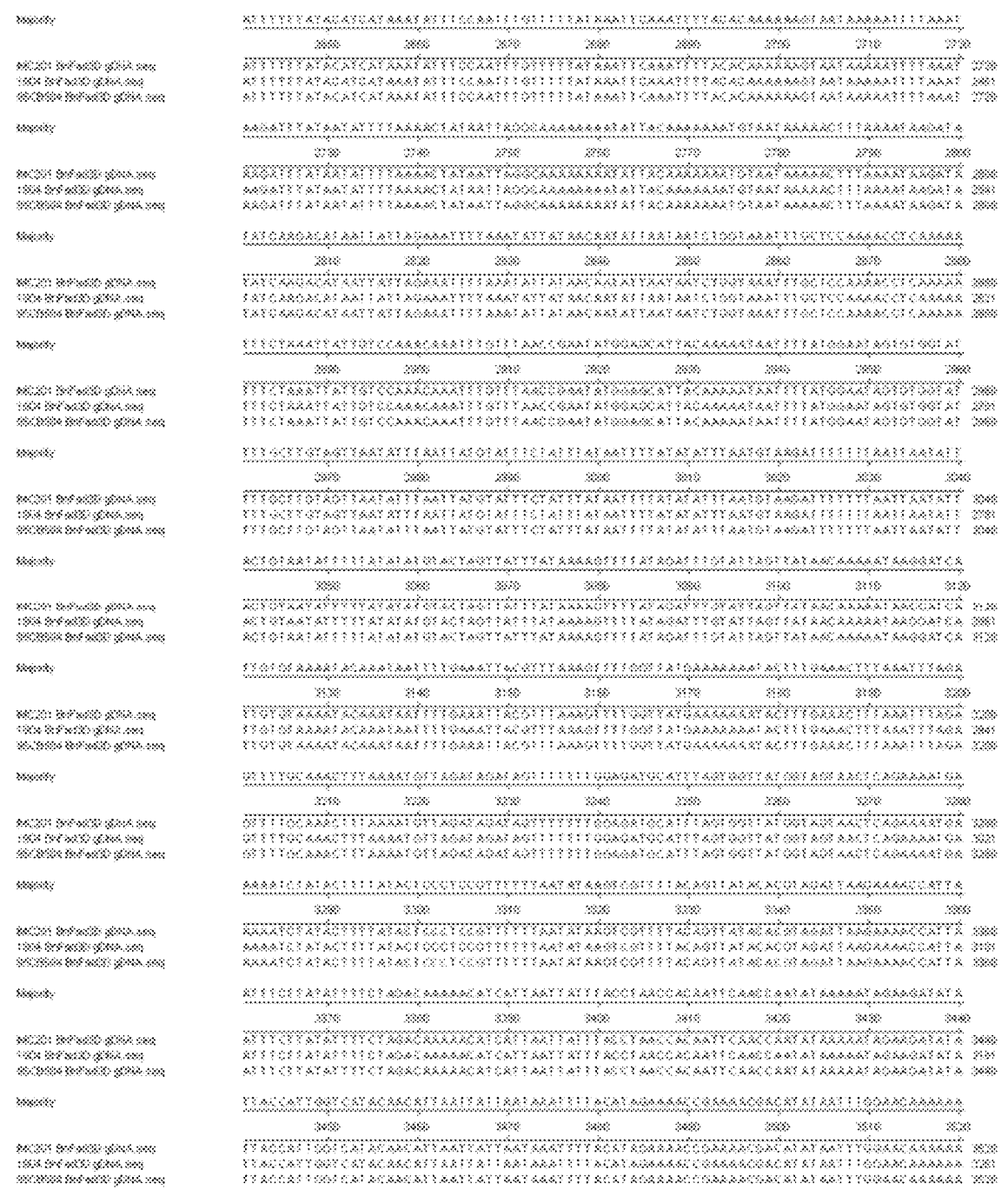
Figure 4:
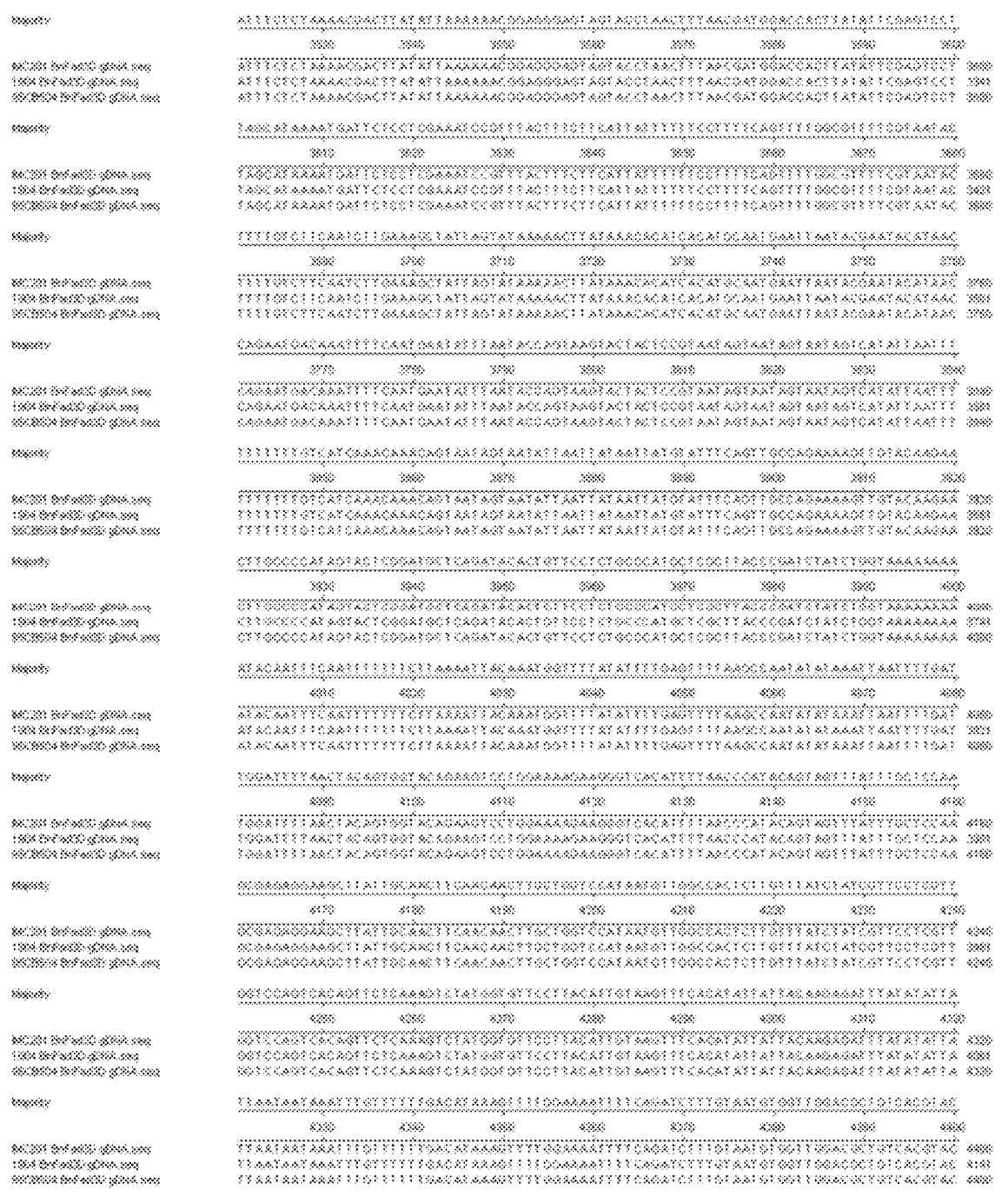
Figure 4:
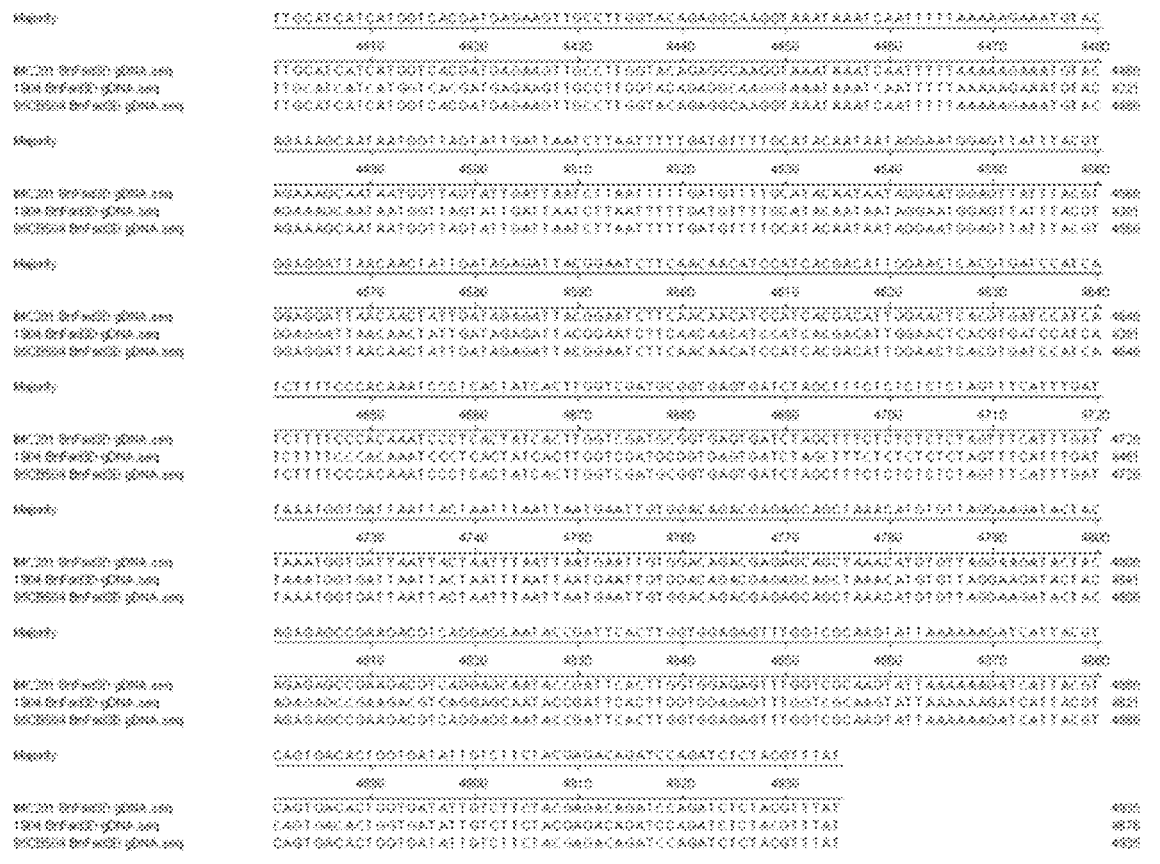

As indicated in Example 2, a $2^{nd}$ QTL was also identified for low linolenic acid content. Comparative genomics located this 2nd QTL on the N5 chromosome of *Brassica napus* and further identified a Fad3D candidate gene on chromosome N5. The Fad3D genes from chromosome N5 of the *Brassica napus* genome were sequenced from 1904-35, 95CB504, and IMC201. The sequences were analyzed using BLAST and DNASTAR/Lasergene 8.0 (DNASTAR, Inc). FIG. 4 shows the sequence alignment of a portion of the BnFad3D gene from 1904-35, 95CB504 and IMC201.

A deletion was identified in one of the two Fad3D isoforms from the 1904-35 mutant line that was not present in 95CB504 and IMC201. The mutant type BnFad3D from 1904-35 has a deletion including a portion of exon 1 (from position 575 to position 739). In IMC201 and 95CB504, exon 1 starts at position 441 and ends at position 739. As a result of the deletion in 1904-35, exon 1 is only 134 bp long. Therefore, it is believed the deletion mutation in 1904 BnFad3D induced a non-functional truncated protein/enzyme due to either lack of RNA splicing (truncated protein with 64 amino acids) or incorrect RNA splicing (truncated protein).

Large scale screening of the parental lines (1904-35 and 95CB504) as well as other *Brassica napus* cultivars, indicated the Fad3D deletion was 1904-35-specific. In addition, the Fad3D deletion was significantly associated with the low ALA phenotype (R-square=0.61, equal to 61% phenotypic variation on C18:3) using the parental lines and 77 DH lines developed from the cross between 1904-35 and 95CB504 compared with 22% explained by BnFad3E-2 mutation in 1904-35. In order to determine the relative effect of individual Fad3 isoform on C18:3 content, 215 lines were used from multiple populations, which carry all Fad3 isoforms, for the multiple regression analysis. Results demonstrated that BnFad3B explains the largest proportion of phenotypic variation on C18:3 content with 26%, followed by 16% by BnFad3D, 8% by BnFad3A, and 7% by BnFad3E.

Example 4

Mutant Fad3A and Fad3B Genes

A population of *B. napus* IMC201 seeds was subjected to chemical mutagenesis as set forth in Example 1. Approximately 200,000 treated seeds were planted in standard greenhouse potting soil and placed into environmentally controlled greenhouse. The plants were grown under sixteen hours of day light. At maturity, M2 seed was harvested from the plants and bulked together. The M2 generation was planted and leaf samples from the early, post-cotyledon stage of development from 8 plants were pooled and DNA was extracted from leaves of these plants. The leaf harvest, pooling and DNA extraction was repeated for approximately 32,000 plants, and resulted in approximately forty 96-well blocks containing mutagenized *B. napus* IMC201 DNA. This grouping of mutagenized DNA is referred to below as the original DNA mutagenesis library.

Additionally, approximately 200,000 treated seeds from the dual mutagen treatment described in Example 1 were planted in standard greenhouse potting soil and placed into environmentally controlled greenhouse. The plants were grown under sixteen hours of day light. At maturity, M2 seed was harvested from the plants and bulked together. This M2 generation was planted in greenhouses and, at flowering, plants were bagged in groups of four to facilitate cross-pollination that would occur in parallel with the majority self pollination events, and seed from this generation was harvested. Genomic DNA from three seeds per plant of this M3 generation was isolated in 96-well blocks; a collection of mutagenized DNA from this process is referred to below as the new Tilling DNA mutagenesis library.

The original DNA mutagenesis library and the new Tilling DNA mutagenesis library were screened to identify stop-codon containing fad3A and fad3B mutant alleles. PCR reactions were performed using *B. napus* IMC201 genomic DNA original mutagenesis library or new Tilling DNA mutagenesis library. PCR products from the original mutagenesis library were analyzed using temperature gradient capillary electrophoresis on a REVEAL® instrument (Transgenomics Inc.), which allows PCR reactions containing heterogeneous PCR products to be distinguished from reactions containing only homogeneous products, as would be the case if a SNP existed in genomic DNA from chemical mutagenesis and subsequent PCR amplification. The PCR products from the new Tilling DNA mutagenesis library were sequenced directly using an Applied Biosystems (Life Technologies) 3730 DNA sequencer using the manufacturer's recommendations.

Individual seeds representing the primary hit of each M2 plant that was the source genomic DNA mix for this primary mutagenesis screen were sampled and genomic DNA was isolated in order to perform the Fad3A PCR on these individuals. PCR products were sequenced and the sequences were compared to the wild-type sequence to screen for the presence of an induced stop codon.

The sequence comparisons indicated that a mutation had been generated and mutant plants obtained for each of the Fad3A and Fad3B genes. The mutant Fad3A sequence is shown in SEQ ID NO: 9 and contains a mutation at position 102, changing the codon from TGG to TGA. The mutant Fad3B sequence is shown in SEQ ID NO:10 and contains a mutation at position 206, resulting in a codon change from TGG to TAG.

Example 5

DH Line Husker

A cross was made between 1904-35 (Example 1) and 95CB504, a B line (maintainer). A double haploid population was generated by collecting $F_1$ microspores from the cross, treating the microspores with colchicine, and propagating them in vitro. Plantlets formed in vitro from the microspores were moved to a greenhouse and inflorescences that formed were self pollinated. Seed was harvested from the $DH_1$ plants at maturity and analyzed for fatty acid profile. Seeds from those plants exhibiting low and high linolenic acid content were grown in the greenhouse. Table 3 contains the fatty acid profile of a bulk sample of seeds produced by each of 5-10 greenhouse-grown plants of a $DH_1$ population designated Husker.

TABLE 3

Fatty acid profile of $DH_1$ population designated Husker

| RESCHID | Pedigree | n | C14:0 | C16:0 | C16:1 | C18:0 | C18:1 | C18:2 | C18:3 | C20:0 |
|---|---|---|---|---|---|---|---|---|---|---|
| Husker-100 | 95CB504xM3B-1904-35 | 5 | 0.00 | 2.308 | 0.078 | 1.728 | 80.758 | 11.130 | 0.766 | 0.774 |
| Husker-141 | 95CB504xM3B-1904-35 | 3 | 0.00 | 3.353 | 0.140 | 2.310 | 78.293 | 11.920 | 0.923 | 0.887 |
| Husker-147 | 95CB504xM3B-1904-35 | 5 | 0.03 | 3.336 | 0.160 | 2.048 | 78.186 | 11.984 | 0.858 | 0.938 |
| Husker-161 | 95CB504xM3B-1904-35 | 5 | 0.03 | 3.688 | 0.242 | 2.246 | 78.816 | 10.864 | 0.814 | 0.920 |
| Husker-107 | 95CB504xM3B-1904-35 | 5 | 0.04 | 4.130 | 0.256 | 2.070 | 75.004 | 12.408 | 2.444 | 0.934 |
| Husker-125 | 95CB504xM3B-1904-35 | 5 | 0.02 | 3.363 | 0.175 | 2.080 | 78.211 | 11.661 | 1.161 | 0.891 |
| Husker-138 | 95CB504xM3B-1904-35 | 5 | 0.02 | 3.574 | 0.195 | 2.151 | 77.702 | 11.767 | 1.240 | 0.914 |
| Husker-170 | 95CB504xM3B-1904-35 | 4 | 0.04 | 4.768 | 0.268 | 1.808 | 75.962 | 11.738 | 2.336 | 0.780 |
| Husker-314 | 95CB504xM3B-1904-35 | 5 | 0.01 | 2.765 | 0.153 | 1.900 | 79.270 | 12.533 | 0.738 | 0.718 |
| Husker-323 | 95CB504xM3B-1904-35 | 5 | 0.03 | 4.526 | 0.168 | 2.370 | 75.004 | 11.948 | 2.338 | 0.934 |
| 95CB504 | | 9 | 0.05 | 3.723 | 0.231 | 2.518 | 78.586 | 9.073 | 2.256 | 1.030 |

| RESCHID | Pedigree | n | C20:1 | C20:2 | C22:0 | C22:1 | C24:0 | C24:1 | TOT SATS |
|---|---|---|---|---|---|---|---|---|---|
| Husker-100 | 95CB504xM3B-1904-35 | 5 | 1.468 | 0.030 | 0.442 | 0.008 | 0.266 | 0.248 | 5.516 |
| Husker-141 | 95CB504xM3B-1904-35 | 3 | 1.227 | 0.000 | 0.447 | 0.000 | 0.233 | 0.273 | 7.227 |
| Husker-147 | 95CB504xM3B-1904-35 | 5 | 1.346 | 0.040 | 0.550 | 0.000 | 0.310 | 0.224 | 7.210 |
| Husker-161 | 95CB504xM3B-1904-35 | 5 | 1.330 | 0.016 | 0.484 | 0.004 | 0.304 | 0.244 | 7.670 |
| Husker-107 | 95CB504xM3B-1904-35 | 5 | 1.474 | 0.030 | 0.598 | 0.006 | 0.364 | 0.242 | 8.140 |
| Husker-125 | 95CB504xM3B-1904-35 | 5 | 1.369 | 0.023 | 0.504 | 0.004 | 0.295 | 0.246 | 7.153 |
| Husker-138 | 95CB504xM3B-1904-35 | 5 | 1.349 | 0.022 | 0.517 | 0.003 | 0.301 | 0.246 | 7.480 |
| Husker-170 | 95CB504xM3B-1904-35 | 4 | 1.344 | 0.018 | 0.478 | 0.000 | 0.232 | 0.224 | 8.108 |
| Husker-314 | 95CB504xM3B-1904-35 | 5 | 1.150 | 0.038 | 0.338 | 0.000 | 0.170 | 0.220 | 5.903 |
| Husker-323 | 95CB504xM3B-1904-35 | 5 | 1.568 | 0.034 | 0.538 | 0.010 | 0.324 | 0.208 | 8.722 |
| 95CB504 | | 9 | 1.446 | 0.040 | 0.533 | 0.017 | 0.321 | 0.189 | 8.163 |

Example 6

DH Line Vest

A cross was made between 2558-35 (Example 1) and Dumpling-314, a double haploid B-line (maintainer) developed from a cross between IMC106RR and Jetton, a known winter rapeseed variety. A double haploid population was generated as described in Example 5. Seed was harvested from the $DH_1$ plants at maturity and analyzed for fatty acid profile. Seeds from those plants exhibiting low linolenic acid content were grown in the greenhouse. Table 4 contains the fatty acid profile of a bulk sample of seeds produced by each of 10 greenhouse-grown plants of a $DH_1$ population designated Vest.

Example 7

Development of Hybrid Canola Producing Reduced ALA in the Seed Oil

A hybrid canola line yielding seeds with an ALA content of less than 1.5% was produced by introducing genes from line 1904-35 (Example 1) into a commercially grown hybrid variety, Victory® v1035. Hybrid v1035 has an average oleic acid content of 65% and an ALA content of 2.8%. Plants of the line 1904-35, and the inbreds 1035R and 95CB504, were planted in a greenhouse. Inbred 1035R is the male parent of v1035. Inbred 95CB504 is the B line female parent of v1035. Plants of 1035R and 1904-35 were cross pollinated in the greenhouse, as were 95CB504 and 1904-35, as shown in Table 5.

TABLE 4

Mean fatty acid profile of Vest DH lines from tails of C18:3 distribution (Vest Population N = 51)

| Research ID | Pedigree | C14:0 | C16:0 | C16:1 | C18:0 | C18:1 | C18:2 | C18:3 | C20:0 |
|---|---|---|---|---|---|---|---|---|---|
| Vest-70 | Dump314-05xM3B-2558-35-2 | 0.069 | 4.507 | 0.223 | 1.983 | 67.152 | 22.456 | 0.653 | 0.778 |
| Vest-52 | Dump314-05xM3B-2558-35-2 | 0.060 | 4.001 | 0.308 | 1.844 | 77.279 | 12.080 | 0.680 | 0.876 |
| Vest-86 | Dump314-05xM3B-2558-35-2 | 0.065 | 4.406 | 0.264 | 2.266 | 79.352 | 9.008 | 0.745 | 1.009 |
| Vest-60 | Dump314-05xM3B-2558-35-2 | 0.072 | 4.685 | 0.273 | 3.143 | 77.323 | 10.143 | 0.787 | 1.217 |
| Vest-87 | Dump314-05xM3B-2558-35-2 | 0.082 | 5.083 | 0.346 | 2.317 | 68.253 | 18.677 | 0.790 | 1.001 |
| Vest-75 | Dump314-05xM3B-2558-35-2 | 0.101 | 5.060 | 0.442 | 2.760 | 70.842 | 14.678 | 1.830 | 1.142 |
| Vest-69 | Dump314-05xM3B-2558-35-2 | 0.143 | 5.840 | 0.653 | 3.079 | 65.526 | 18.353 | 1.952 | 1.359 |
| Vest-71 | Dump314-05xM3B-2558-35-2 | 0.103 | 5.719 | 0.515 | 4.595 | 57.872 | 23.001 | 2.039 | 1.673 |
| Vest-92 | Dump314-05xM3B-2558-35-2 | 0.137 | 6.678 | 0.606 | 3.026 | 54.170 | 28.786 | 2.423 | 1.300 |
| Vest-97 | Dump314-05xM3B-2558-35-2 | 0.126 | 6.439 | 0.643 | 3.483 | 54.626 | 27.270 | 2.528 | 1.315 |
| | Dumpling-314 avg (n = 4) | 0.051 | 4.405 | 0.255 | 2.259 | 67.459 | 20.564 | 1.396 | 0.969 |

| Research ID | Pedigree | C20:1 | C20:2 | C22:0 | C22:1 | C24:0 | C24:1 | TOT SATS |
|---|---|---|---|---|---|---|---|---|
| Vest-70 | Dump314-05xM3B-2558-35-2 | 1.191 | 0.066 | 0.431 | 0.048 | 0.249 | 0.193 | 8.017 |
| Vest-52 | Dump314-05xM3B-2558-35-2 | 1.562 | 0.053 | 0.571 | 0.043 | 0.411 | 0.233 | 7.762 |
| Vest-86 | Dump314-05xM3B-2558-35-2 | 1.486 | 0.044 | 0.623 | 0.044 | 0.468 | 0.220 | 8.838 |
| Vest-60 | Dump314-05xM3B-2558-35-2 | 1.287 | 0.042 | 0.597 | 0.000 | 0.430 | 0.000 | 10.145 |
| Vest-87 | Dump314-05xM3B-2558-35-2 | 1.284 | 0.064 | 0.624 | 0.000 | 0.505 | 0.976 | 9.612 |
| Vest-75 | Dump314-05xM3B-2558-35-2 | 1.415 | 0.067 | 0.657 | 0.000 | 0.516 | 0.491 | 10.235 |
| Vest-69 | Dump314-05xM3B-2558-35-2 | 1.324 | 0.111 | 0.842 | 0.000 | 0.626 | 0.192 | 11.889 |
| Vest-71 | Dump314-05xM3B-2558-35-2 | 1.125 | 0.085 | 1.005 | 0.000 | 0.660 | 1.608 | 13.755 |
| Vest-92 | Dump314-05xM3B-2558-35-2 | 1.191 | 0.000 | 0.695 | 0.000 | 0.628 | 0.359 | 12.464 |
| Vest-97 | Dump314-05xM3B-2558-35-2 | 1.088 | 0.000 | 0.712 | 0.441 | 0.616 | 0.715 | 12.690 |
| | Dumpling-314 avg (n = 4) | 1.380 | 0.062 | 0.571 | 0.016 | 0.454 | 0.160 | 8.708 |

TABLE 5

| Female | x | Male |
|---|---|---|
| 1035R (R-line) | | 1904-35 |
| 95CB504 (B-line) | | 1904-35 |

$F_1$ progeny from the cross of 95CB504 and 1904-35 were backcrossed to 95CB504 to produce $BC_1$-B progeny, which were selfed ($BC_1S$). Plants with low total saturates were selected from the $BC_1$-B selfed progeny, and backcrossed to 95CB504 to produce $BC_2$-B progeny. $F_1$ progeny from the cross of 1035R and 1904-35 were backcrossed to 1035R to produce $BC_1$-R progeny, which were selfed. Plants with low linolenic were selected from the $BC_1$-R selfed progeny, and backcrossed to 1035R to produce $BC_2$-R progeny. Backcrossing, selection, and self-pollination of the BC-B and BC-R progeny were continued for multiple generations. The 95CB504 male sterile A line, 000A05 was converted to a low linolenic phenotype in parallel with the conversion of the 95CB504 B line. Table 6 shows the mean C18:3 content of selected lines of converted $BC_3S_5$ generation parent lines compared unconverted 95CB504 and 1035R.

Hybrid seed was generated by hand, using $BC_1S_3$ generation plants of the 95CB504 B line as the female parent and $BC_1S_3$ generation plants of the 1035R R line as the male parent. The hybrid seed was grown at 5 locations×4 replications in Western Canada. In the trial plot locations, some individual plants were bagged for self pollination (5 locations×2 reps) and seeds harvested at maturity. The remaining plants were not bagged (5 locations×4 reps) and seeds were harvested in bulk. As such, the bulk samples had some level of out crossing with non-low linolenic fatty acid lines in adjacent plots. Seeds from the individual and bulk samples were analyzed for fatty acid content. Seeds from control plants of line Q2, hybrid v1035 and commercial variety 46A65 were also harvested individually and in bulk.

Table 7 shows the fatty acid profile of the individually bagged samples and bulked samples for hybrid 1904-35 and controls. The results indicate that seed produced by Hybrid 1904-35 has a statistically significant decrease in 18:3 content relative to the controls.

TABLE 6

Mean linolenic acid content of parental controls and converted parents.

ANOVA BC3S5 Populations

| Greenhouse ID | Pedigree | Mean C18:3 | N |
|---|---|---|---|
| 09AP:Waring42 a | 1035R | 1.914 | 8 |
| 09AP:Waring43 a | 95CB504 | 1.892 | 6 |
| 09AP:Waring30 b | 95CB504xM3B-1904 | 1.231 | 20 |
| 09AP:Waring25 b | 95CB504xM3B-1904 | 1.226 | 20 |
| 09AP:Waring27 b | 95CB504xM3B-1904 | 1.206 | 20 |
| 09AP:Waring28 b | 95CB504xM3B-1904 | 1.198 | 20 |
| 09AP:Waring29 b | 95CB504xM3B-1904 | 1.174 | 20 |
| 09AP:Waring32 b | 95CB504xM3B-1904 | 1.165 | 20 |
| 09AP:Waring26 b | 95CB504xM3B-1904 | 1.163 | 20 |
| 09AP:Waring33 b | 95CB504xM3B-1904 | 1.146 | 20 |
| 09AP:Waring31 c | 95CB504xM3B-1904 | 1.081 | 20 |
| 09AP:Waring7 d | 1035R BxM3B-1904 | 0.797 | 20 |
| 09AP:Waring18 de | 1035R BxM3B-1904 | 0.780 | 20 |
| 09AP:Waring14 def | 1035R BxM3B-1904 | 0.773 | 20 |
| 09AP:Waring11 def | 1035R BxM3B-1904 | 0.760 | 20 |
| 09AP:Waring13 def | 1035R BxM3B-1904 | 0.755 | 18 |
| 09AP:Waring8 def | 1035R BxM3B-1904 | 0.755 | 20 |
| 09AP:Waring16 def | 1035R BxM3B-1904 | 0.752 | 20 |
| 09AP:Waring21 def | 1035R BxM3B-1904 | 0.751 | 19 |
| 09AP:Waring17 def | 1035R BxM3B-1904 | 0.751 | 20 |
| 09AP:Waring12 def | 1035R BxM3B-1904 | 0.737 | 20 |
| 09AP:Waring19 def | 1035R BxM3B-1904 | 0.728 | 20 |
| 09AP:Waring10 efg | 1035R BxM3B-1904 | 0.692 | 20 |
| 09AP:Waring9 efg | 1035R BxM3B-1904 | 0.691 | 20 |
| 09AP:Waring20 efg | 1035R BxM3B-1904 | 0.681 | 20 |
| 09AP:Waring15 fg | 1035R BxM3B-1904 | 0.668 | 20 |
| 09AP:Waring23 g | 1035R BxM3B-1904 | 0.634 | 20 |
| 09AP:Waring22 g | 1035R BxM3B-1904 | 0.632 | 19 |
| 09AP:Waring24 g | 1035R BxM3B-1904 | 0.598 | 20 |

* Demonstrates significant difference between recurrent parent and backcross selections

TABLE 7

Mean linolenic fatty acid content of converted hybrid, v1035 and controls.

| reschid | mean | s.e. | N |
|---|---|---|---|
| Student-Newman-Keuls Tests for C18_3 Data Pooled for Bulked and Selfed Seed | | | |
| Q2 | 8.142 a | 0.218 | 30 |
| 46A65 | 7.528 b | 0.098 | 29 |
| V1035 | 2.874 c | 0.170 | 31 |
| 1904 Conversion | 1.504 d | 0.118 | 30 |
| Data Separated for Bulked and Selfed Seed | | | |
| Q2 | 8.206 a | 0.536 | 11 |
| Q2 Bulk | 8.105 a | 0.166 | 19 |
| 46A65 | 7.823 a | 0.168 | 10 |
| 46A65 Bulk | 7.372 a | 0.107 | 19 |
| V1035 | 3.156 b | 0.481 | 10 |
| V1035 Bulk | 2.739 b | 0.108 | 21 |
| 1904 Conversion Bulk | 1.546 c | 0.123 | 19 |
| 1904 Conversion | 1.431 c | 0.250 | 11 |

Example 8

Crosses were made between selections from lines of double haploid population Vest (Example 6) and reduced saturated fatty acid lines F6 (1764-43-06×1975-90-14) and 06JAXB (01OB054R×15.36). The reduced saturated fatty acid lines are described in U.S. Provisional Application No. 61/287,985, filed Dec. 18, 2009, and U.S. Provisional Application No. 61/295,049, filed Jan. 14, 2010. Double haploid populations were generated from these crosses as described in Example 4. Seed was harvested from the DH1 plants at maturity and analyzed for fatty acid profile. Table 8 contains the fatty acid profile of seeds produced by each of 1 greenhouse-grown plant from DH1 populations designated GP#1, GP#4 and GP#5 as well as 3 parental lines grown as reduced linolenic and total saturated fatty acid controls.

TABLE 8

| Research ID | Pedigree | C14:0 | C16:0 | C16:1 | C18:0 | C18:1 | C18:2 | C18:3 | C20:0 |
|---|---|---|---|---|---|---|---|---|---|
| GP #1-396 | Vest-57x(1764-43-6x1975-90-14) | 0.03 | 2.62 | 0.16 | 1.06 | 77.82 | 14.26 | 1.03 | 0.46 |

TABLE 8-continued

| Research ID | Pedigree | | | | | | | |
|---|---|---|---|---|---|---|---|---|
| GP #1-24 | Vest-57x(1764-43-6x1975-90-14) | 0.05 | 3.11 | 0.29 | 0.95 | 74.63 | 16.92 | 1.06 | 0.47 |
| GP #1-181 | Vest-57x(1764-43-6x1975-90-14) | 0.04 | 3.11 | 0.26 | 1.02 | 75.24 | 16.41 | 1.06 | 0.46 |
| GP #1-444 | Vest-57x(1764-43-6x1975-90-14) | 0.03 | 2.78 | 0.23 | 1.15 | 76.61 | 14.89 | 0.99 | 0.53 |
| GP #1-449 | Vest-57x(1764-43-6x1975-90-14) | 0.03 | 3.02 | 0.25 | 1.11 | 77.22 | 14.22 | 1.08 | 0.51 |
| GP #1-240 | Vest-57x(1764-43-6x1975-90-14) | 0.00 | 2.80 | 0.20 | 1.35 | 74.47 | 16.93 | 1.04 | 0.55 |
| GP #1-150 | Vest-57x(1764-43-6x1975-90-14) | 0.04 | 2.59 | 0.19 | 1.54 | 79.41 | 12.02 | 0.97 | 0.63 |
| GP #4-20 | Vest-70x(1764-43-6x1975-90-14) | 0.02 | 2.74 | 0.17 | 1.28 | 75.26 | 16.19 | 1.04 | 0.55 |
| GP #4-17 | Vest-70x(1764-43-6x1975-90-14) | 0.03 | 3.48 | 0.16 | 1.22 | 65.47 | 25.83 | 0.82 | 0.51 |
| GP #5-434 | (01OB054RxLSAt15.36)xVest-57-05 | 0.03 | 2.83 | 0.13 | 1.56 | 77.51 | 13.35 | 1.09 | 0.66 |
| GP #5-* | (01OB054RxLSAt15.36)xVest-57-05 | 0.03 | 2.99 | 0.23 | 1.31 | 86.21 | 4.37 | 1.11 | 0.67 |
| GP #5-351 | (01OB054RxLSAt15.36)xVest-57-05 | 0.02 | 3.47 | 0.00 | 1.43 | 76.99 | 14.12 | 0.86 | 0.60 |
| GP #5-334 | (01OB054RxLSAt15.36)xVest-57-05 | 0.03 | 3.16 | 0.18 | 1.52 | 73.74 | 16.87 | 1.05 | 0.62 |
| GP #5-404 | (01OB054RxLSAt15.36)xVest-57-05 | 0.03 | 2.96 | 0.15 | 1.61 | 79.04 | 11.59 | 1.08 | 0.70 |
| GP #5-332 | (01OB054RxLSAt15.36)xVest-57-05 | 0.04 | 3.16 | 0.22 | 1.61 | 86.99 | 3.90 | 1.02 | 0.66 |
| GP #5-344 | (01OB054RxLSAt15.36)xVest-57-05 | 0.04 | 2.92 | 0.23 | 1.71 | 86.45 | 4.10 | 0.97 | 0.79 |
| | (1764-43-6x1975-90-14) avg (n = 12) | 0.03 | 2.89 | 0.21 | 1.17 | 70.30 | 18.55 | 2.84 | 0.61 |
| | Vest-57 avg (n = 10) | 0.04 | 4.17 | 0.23 | 1.67 | 77.79 | 11.35 | 0.91 | 0.83 |
| | Vest-70 avg (n = 12) | 0.06 | 4.76 | 0.21 | 1.60 | 65.52 | 23.50 | 0.95 | 0.74 |

| Research ID | Pedigree | C20:1 | C20:2 | C22:0 | C22:1 | C24:0 | C24:1 | TOT SATS |
|---|---|---|---|---|---|---|---|---|
| GP #1-396 | Vest-57x(1764-43-6x1975-90-14) | 1.67 | 0.10 | 0.34 | 0.05 | 0.21 | 0.20 | 4.72 |
| GP #1-24 | Vest-57x(1764-43-6x1975-90-14) | 1.60 | 0.07 | 0.33 | 0.04 | 0.17 | 0.30 | 5.08 |
| GP #1-181 | Vest-57x(1764-43-6x1975-90-14) | 1.55 | 0.07 | 0.32 | 0.04 | 0.19 | 0.22 | 5.15 |
| GP #1-444 | Vest-57x(1764-43-6x1975-90-14) | 1.72 | 0.07 | 0.40 | 0.04 | 0.27 | 0.27 | 5.16 |
| GP #1-449 | Vest-57x(1764-43-6x1975-90-14) | 1.68 | 0.08 | 0.34 | 0.03 | 0.18 | 0.25 | 5.20 |
| GP #1-240 | Vest-57x(1764-43-6x1975-90-14) | 1.64 | 0.10 | 0.38 | 0.06 | 0.25 | 0.24 | 5.32 |
| GP #1-150 | Vest-57x(1764-43-6x1975-90-14) | 1.67 | 0.09 | 0.38 | 0.03 | 0.22 | 0.23 | 5.39 |
| GP #4-20 | Vest-70x(1764-43-6x1975-90-14) | 1.76 | 0.10 | 0.35 | 0.06 | 0.26 | 0.23 | 5.21 |
| GP #4-17 | Vest-70x(1764-43-6x1975-90-14) | 1.58 | 0.11 | 0.34 | 0.05 | 0.16 | 0.25 | 5.74 |
| GP #5-434 | (01OB054RxLSAt15.36)xVest-57-05 | 1.76 | 0.10 | 0.44 | 0.05 | 0.24 | 0.25 | 5.76 |
| GP #5-* | (01OB054RxLSAt15.36)xVest-57-05 | 1.92 | 0.05 | 0.52 | 0.05 | 0.29 | 0.26 | 5.80 |
| GP #5-351 | (01OB054RxLSAt15.36)xVest-57-05 | 1.71 | 0.06 | 0.34 | 0.04 | 0.19 | 0.18 | 6.04 |
| GP #5-334 | (01OB054RxLSAt15.36)xVest-57-05 | 1.69 | 0.10 | 0.41 | 0.05 | 0.31 | 0.26 | 6.05 |
| GP #5-404 | (01OB054RxLSAt15.36)xVest-57-05 | 1.74 | 0.08 | 0.49 | 0.05 | 0.29 | 0.18 | 6.08 |
| GP #5-332 | (01OB054RxLSAt15.36)xVest-57-05 | 1.44 | 0.05 | 0.44 | 0.05 | 0.27 | 0.15 | 6.18 |
| GP #5-344 | (01OB054RxLSAt15.36)xVest-57-05 | 1.76 | 0.07 | 0.48 | 0.04 | 0.24 | 0.20 | 6.19 |
| | (1764-43-6x1975-90-14) avg (n = 12) | 1.92 | 0.15 | 0.50 | 0.12 | 0.35 | 0.37 | 5.54 |
| | Vest-57 avg (n = 10) | 1.57 | 0.06 | 0.63 | 0.06 | 0.42 | 0.28 | 7.75 |
| | Vest-70 avg (n = 12) | 1.40 | 0.09 | 0.52 | 0.06 | 0.33 | 0.28 | 8.01 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A *Brassica napus* seed designated 1904 and represented by American Type Culture Collection (ATCC) Accession No. PTA-11273.

2. A plant grown from the seed of claim 1, wherein said seed comprises a modified allele at a fatty acid desaturase 3E fad3E locus.

3. A *Brassica napus* seed designated 2558 and represented by American Type Culture Collection (ATCC) Accession No. PTA-11274.

4. A plant grown from the seed of claim 3, wherein said seed comprises a modified allele at a fad3E locus.

5. The seed of the plant of claim 2, wherein said seed comprises a modified allele at a fad3E locus.

6. The seed of the plant of claim 4, wherein said seed comprises a modified allele at a fad3E locus.

* * * * *